United States Patent
Agrawal et al.

(10) Patent No.: US 10,946,082 B2
(45) Date of Patent: *Mar. 16, 2021

(54) IMMUNOMODULATORY COMPOSITIONS AND METHODS OF USE THEREOF

(71) Applicants: Babita Agrawal, Edmonton (CA); Rakesh Kumar, Edmonton (CA)

(72) Inventors: Babita Agrawal, Edmonton (CA); Rakesh Kumar, Edmonton (CA)

(73) Assignees: Agrawal Babita, Edmonton (CA); Kumar Rakesh, Edmonton (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/511,847

(22) Filed: Jul. 15, 2019

(65) Prior Publication Data

US 2020/0054731 A1  Feb. 20, 2020

Related U.S. Application Data

(63) Continuation of application No. 15/108,744, filed as application No. PCT/IB2015/050108 on Jan. 7, 2015, now Pat. No. 10,369,205.

(60) Provisional application No. 61/924,607, filed on Jan. 7, 2014.

(51) Int. Cl.

| | |
|---|---|
| *A61K 39/39* | (2006.01) |
| *A61K 39/02* | (2006.01) |
| *A61K 39/00* | (2006.01) |
| *A61K 39/015* | (2006.01) |
| *A61K 39/04* | (2006.01) |
| *A61K 39/12* | (2006.01) |
| *A61K 39/35* | (2006.01) |
| *A61K 39/395* | (2006.01) |

(52) U.S. Cl.
CPC .......... *A61K 39/02* (2013.01); *A61K 39/0011* (2013.01); *A61K 39/015* (2013.01); *A61K 39/04* (2013.01); *A61K 39/12* (2013.01); *A61K 39/35* (2013.01); *A61K 39/39* (2013.01); *A61K 39/395* (2013.01); *A61K 2039/505* (2013.01); *A61K 2039/521* (2013.01); *A61K 2039/55516* (2013.01); *A61K 2039/55572* (2013.01); *A61K 2039/58* (2013.01); *C12N 2710/10343* (2013.01); *C12N 2730/10134* (2013.01); *C12N 2760/16134* (2013.01); *C12N 2760/16234* (2013.01); *C12N 2770/24234* (2013.01); *Y02A 50/30* (2018.01)

(58) Field of Classification Search
None
See application file for complete search history.

(56) References Cited

PUBLICATIONS

Bhatnagar et al. 2006 (Anti-tumor effects of the Bacterium Caulobacter crescentus in Murine Tumor Models; Cancer Biology & Therapy 5(5):485-491) (Year: 2006).*
List of references on Jan. 2, 2018 in parent U.S. Pat. No. 10,369,205.
List of references on Jun. 22, 2017 in parent U.S. Pat. No. 10,369,205.
List of references on Nov. 4, 2016 in parent U.S. Pat. No. 10,369,205.
Information Disclosure Statement by applicant submitted on Dec. 22, 2016 in paretn U.S. Pat. No. 10,369,205.

* cited by examiner

*Primary Examiner* — Mary Maille Lyons
(74) *Attorney, Agent, or Firm* — BCF LLP

(57) ABSTRACT

The present disclosure provides immunomodulatory compositions comprising heat-killed *Caulobacter crescentus* (HKCC). Immunomodulatory compositions of the present disclosure are useful for modulating an immune response in an individual. The present disclosure thus provides methods of modulating an immune response in an individual, involving administering an immunomodulatory composition comprising HKCC to the individual.

10 Claims, 31 Drawing Sheets
Specification includes a Sequence Listing.

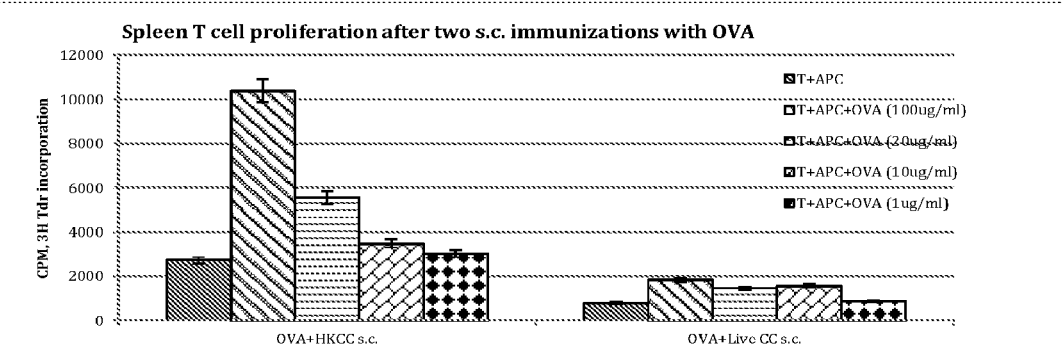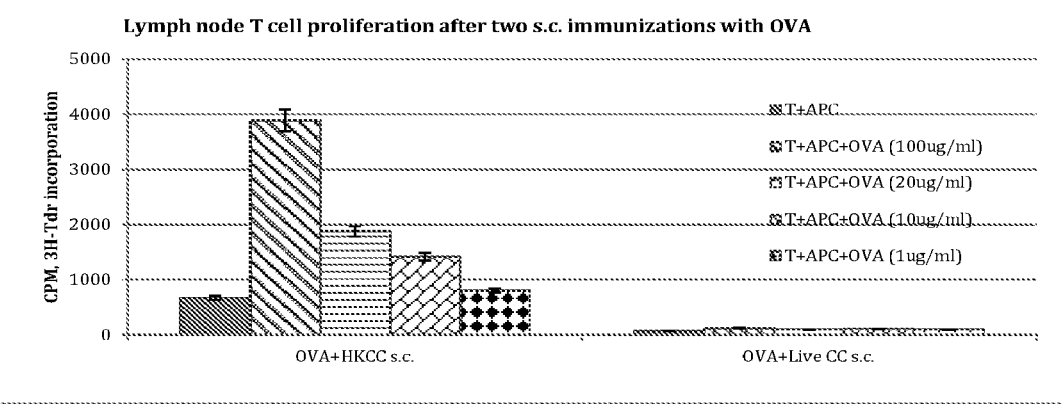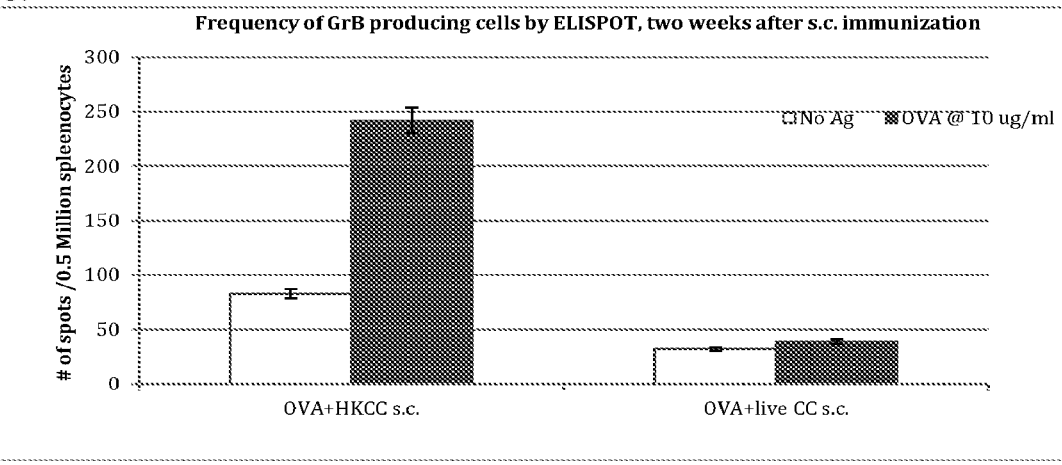
Figure 2A-C

2D.
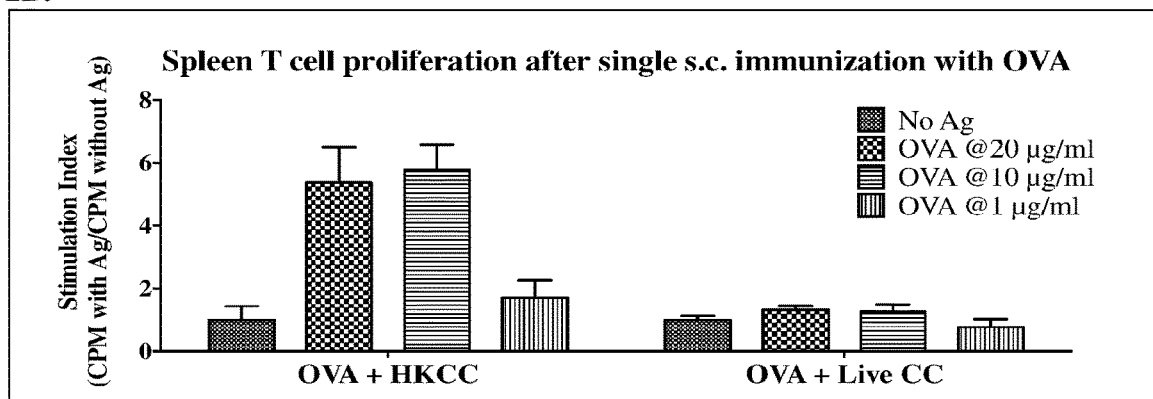
2E.
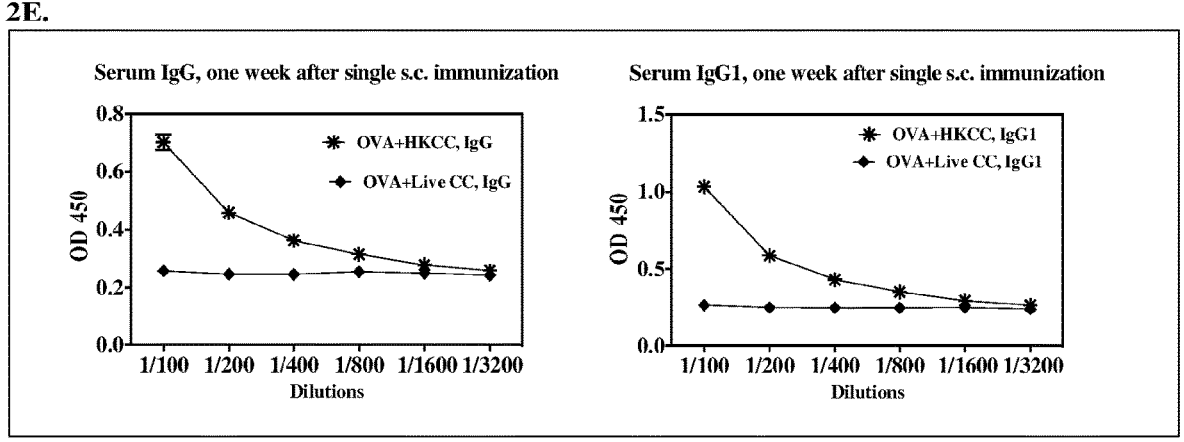
Figure 2D, E

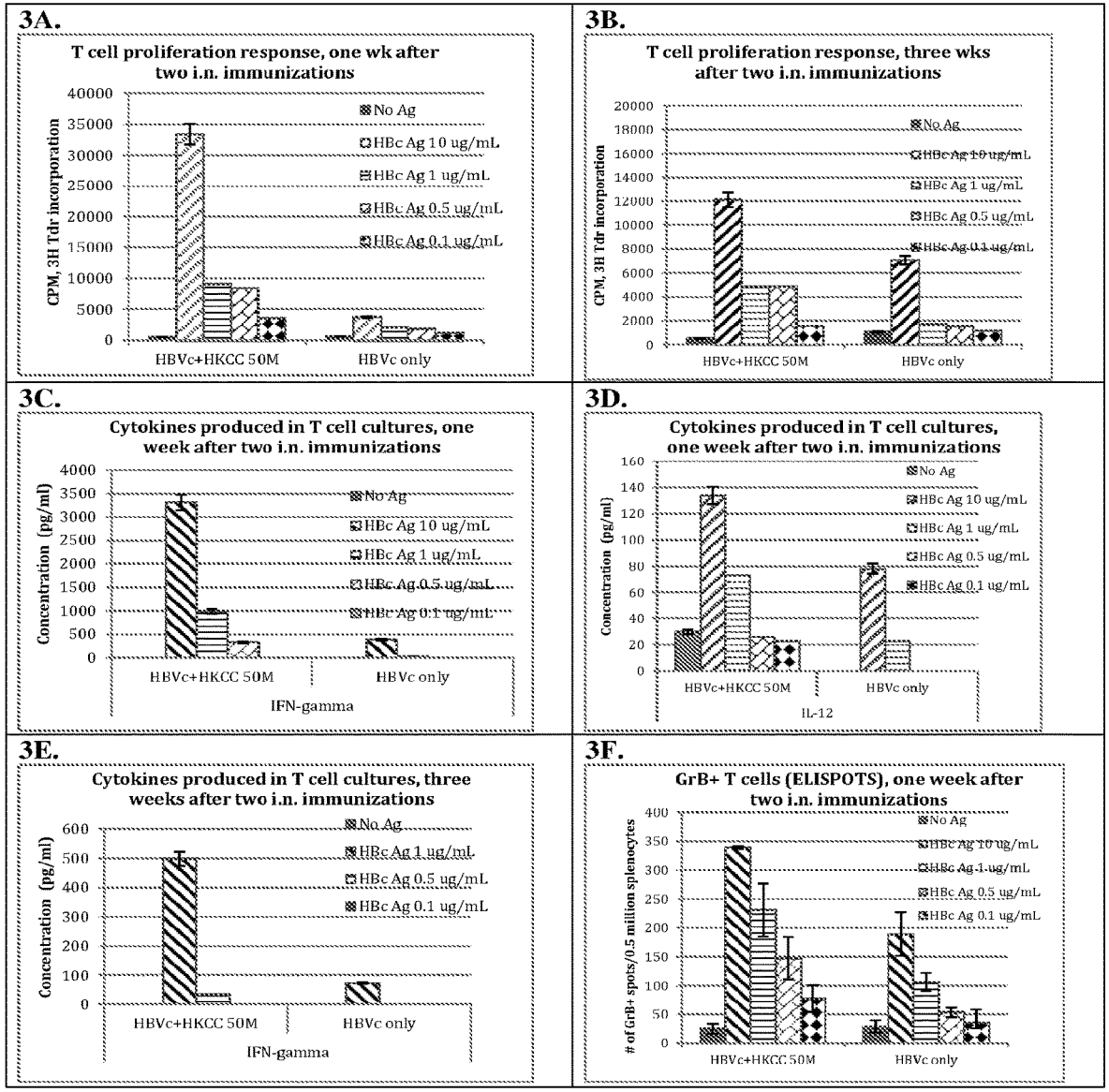
Figure 3 A-F

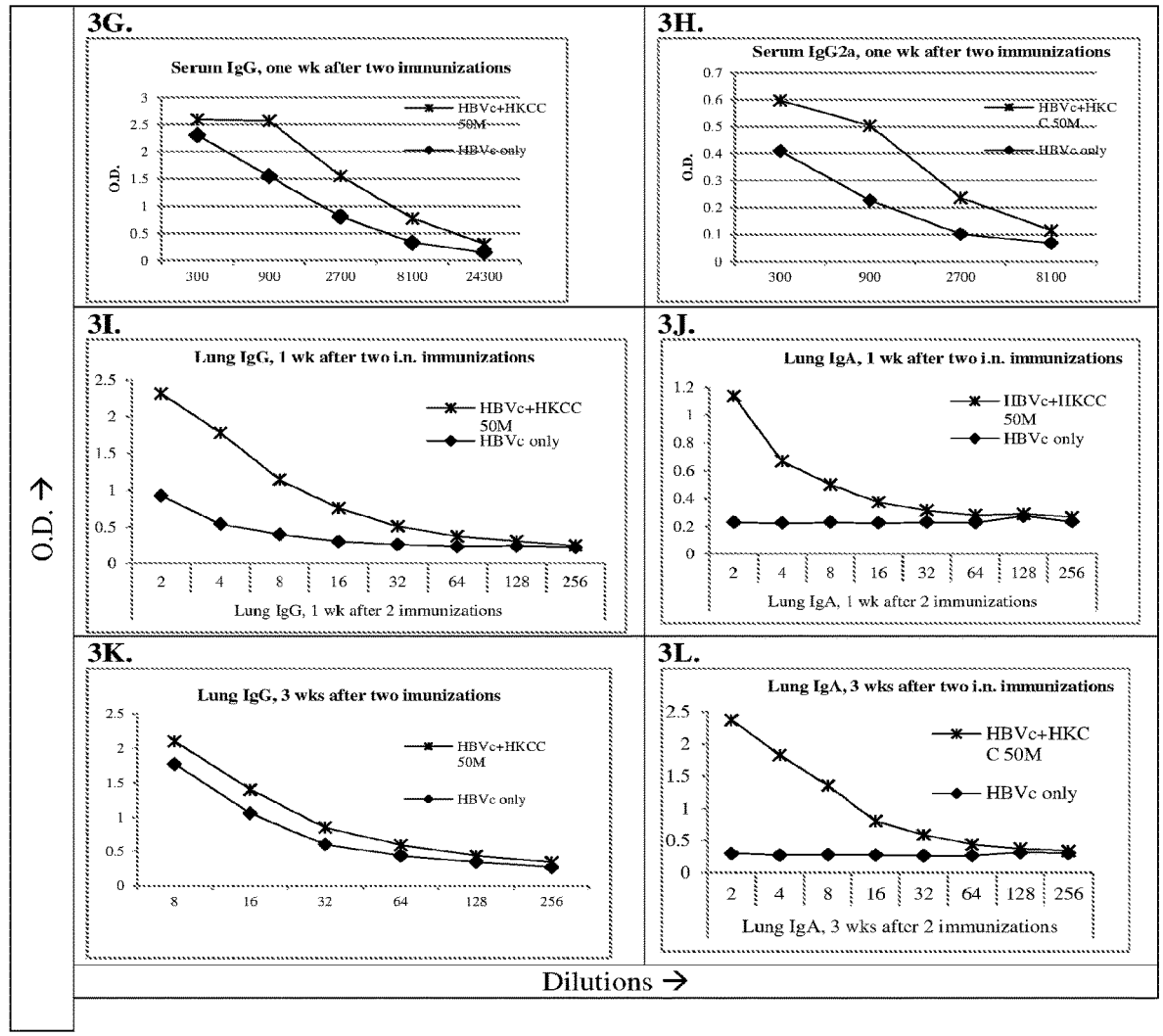
Figure 3G-L

5A.
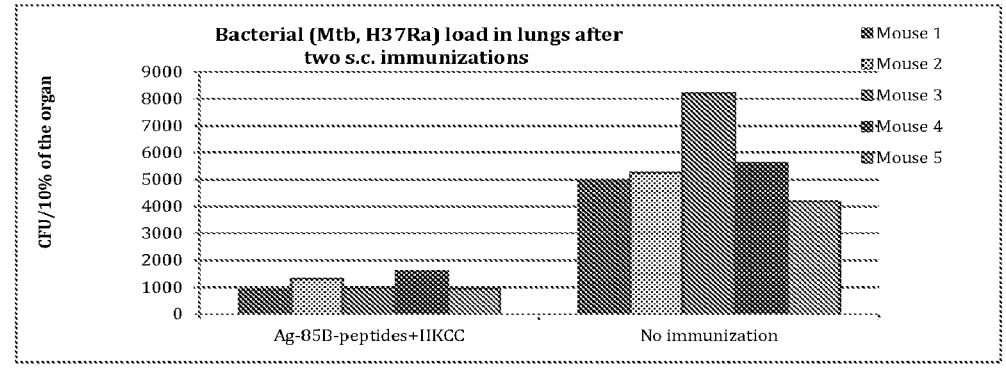
5B.
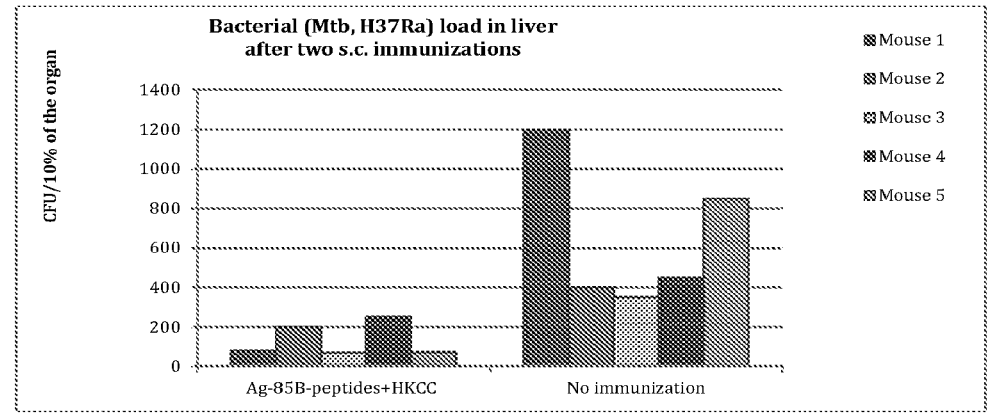
5C.
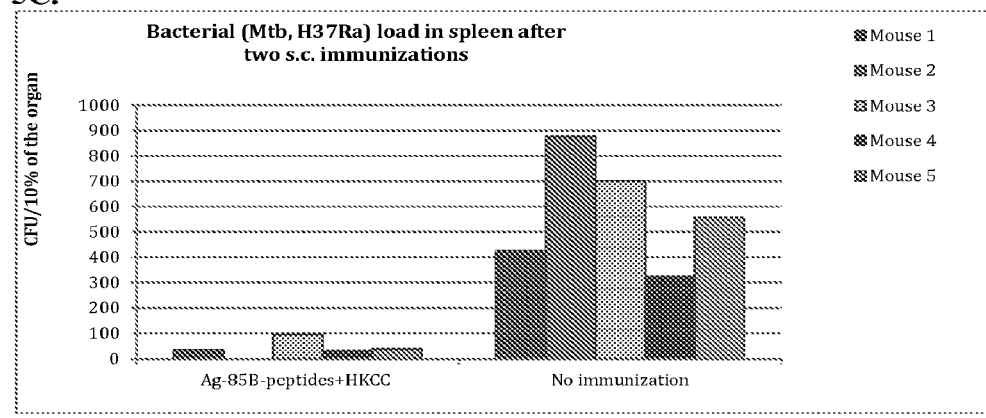
Figure 5A-C

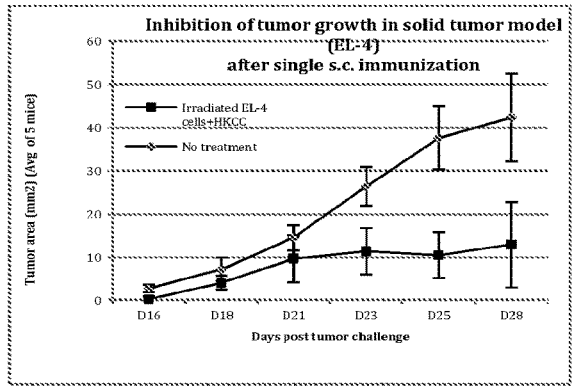
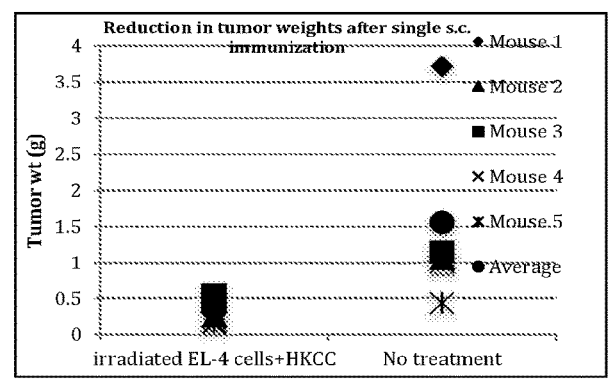
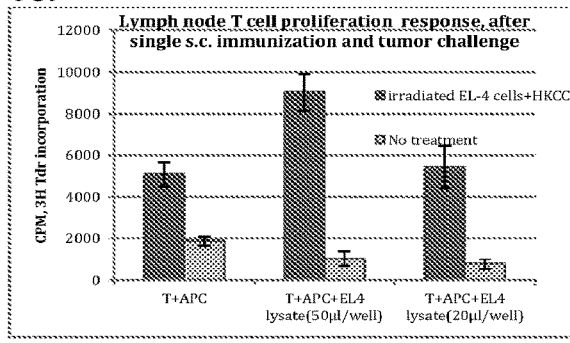
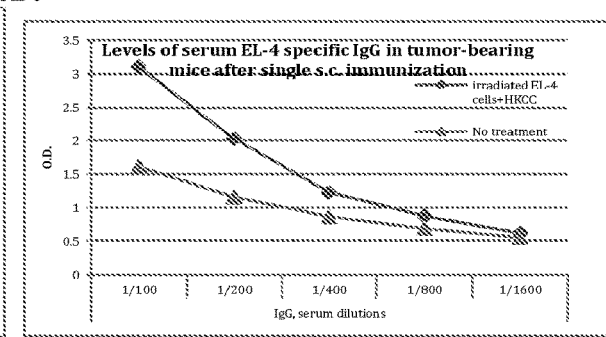
Figure 6A-D

7A.
Irradiated B16 cells+HKCC, single s.c. immunization    No treatment
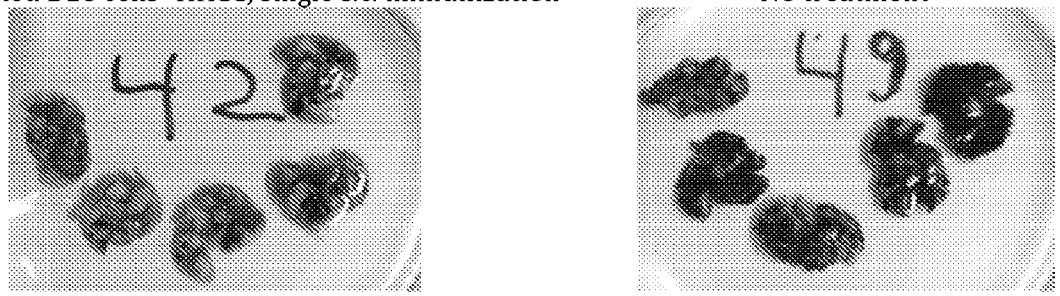
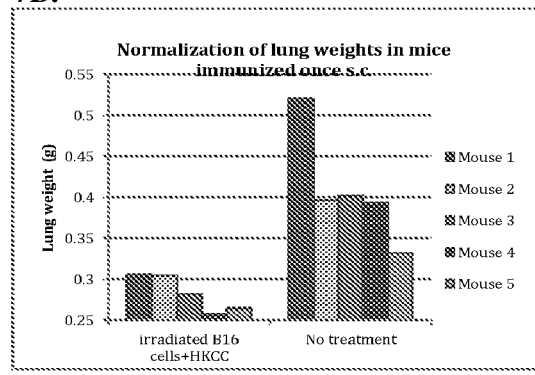
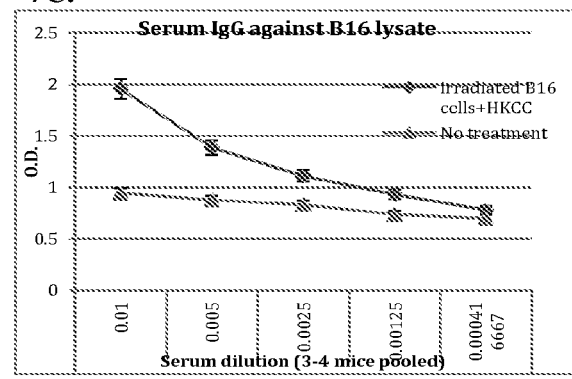
Figure 7A-C 8A.
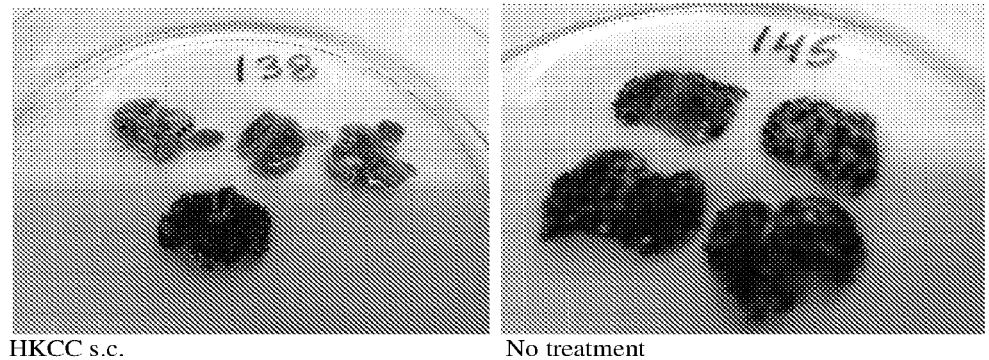
HKCC s.c.　　　　　　　　　　　　　　　No treatment
8B.
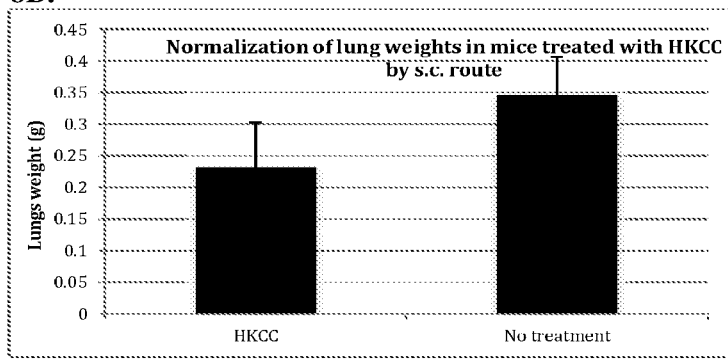
8C.
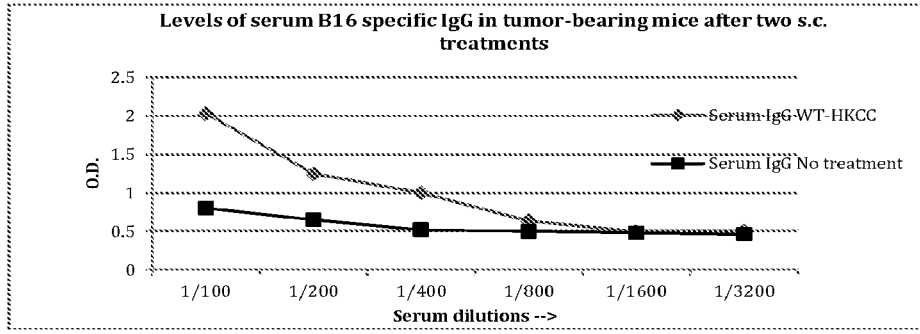
Figure 8A-C

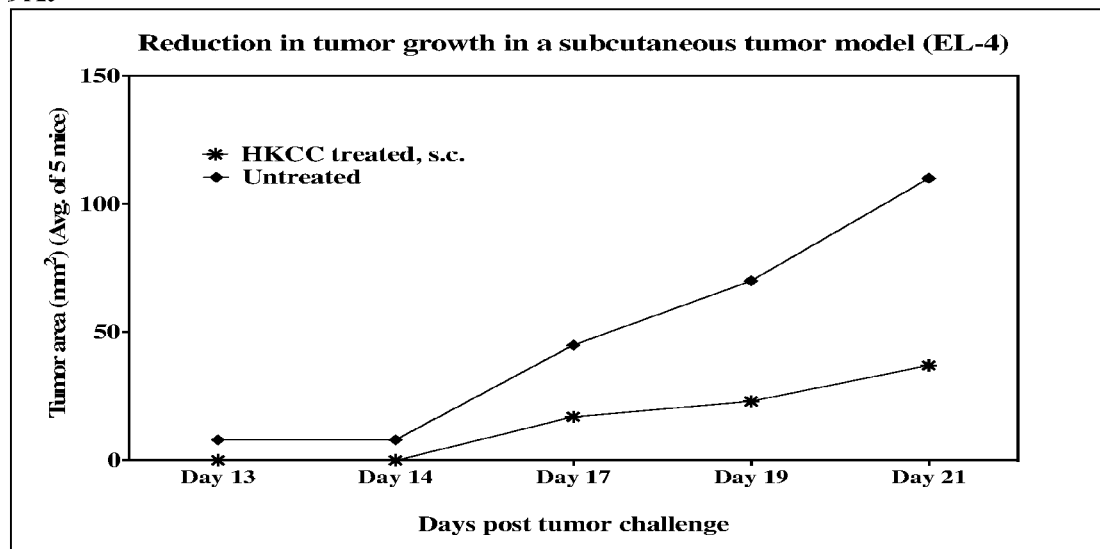
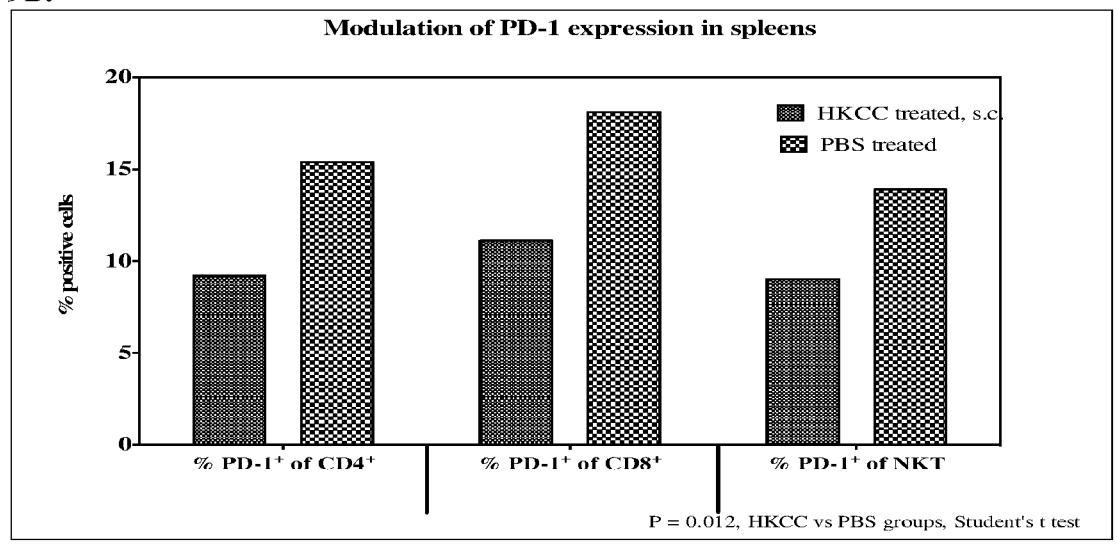
Figure 9A, B

10A.
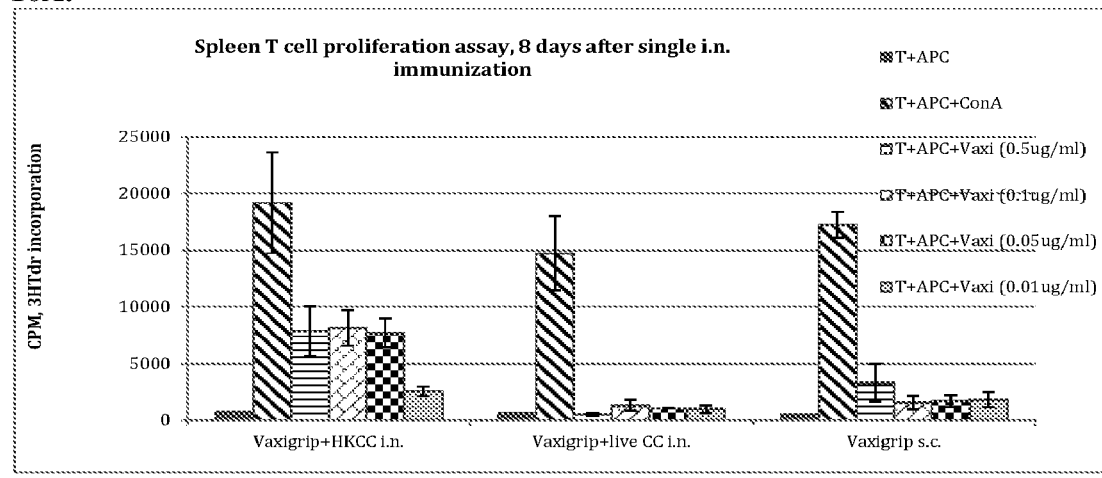
10B.
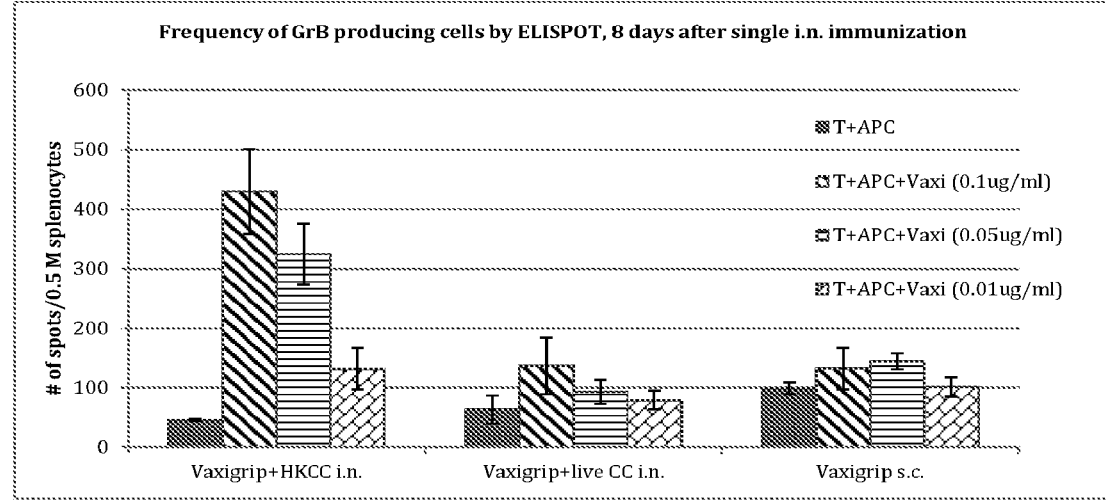
Figure 10 A,B

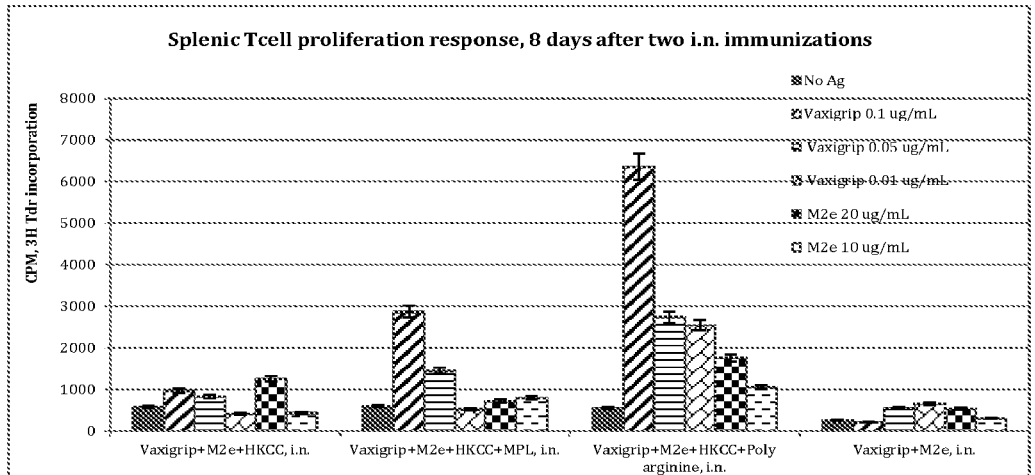
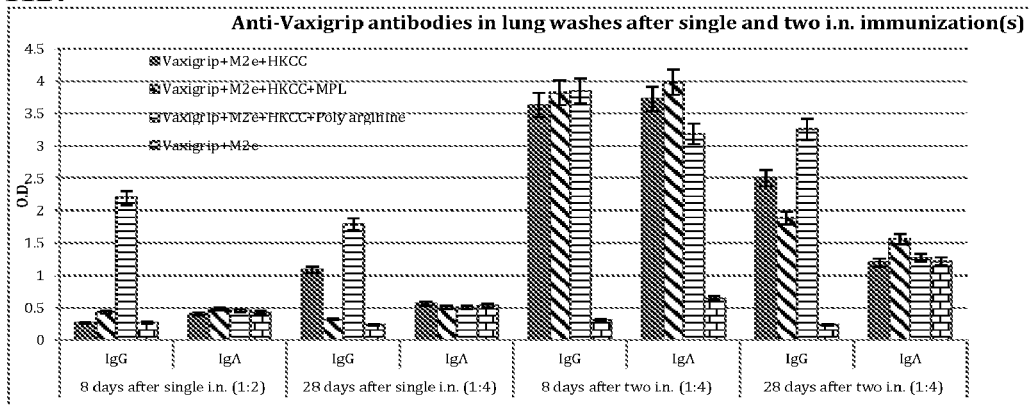
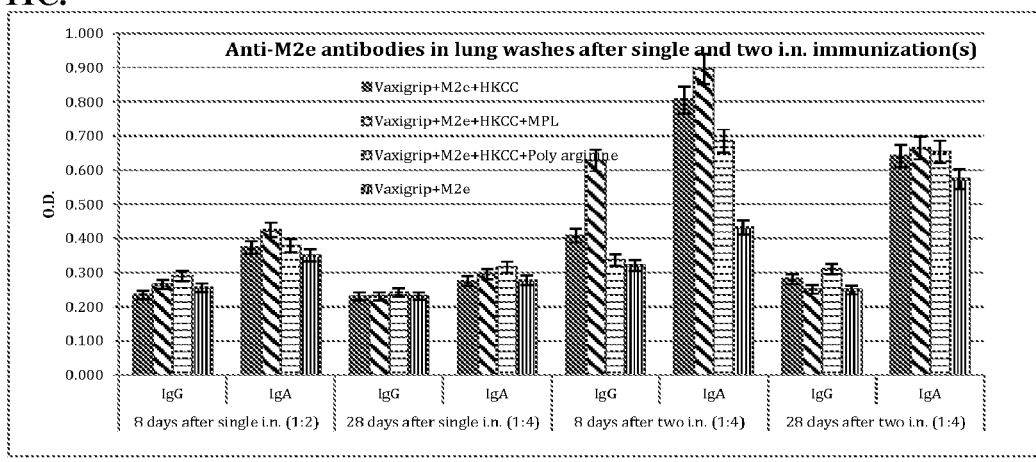
Figure 11A-C

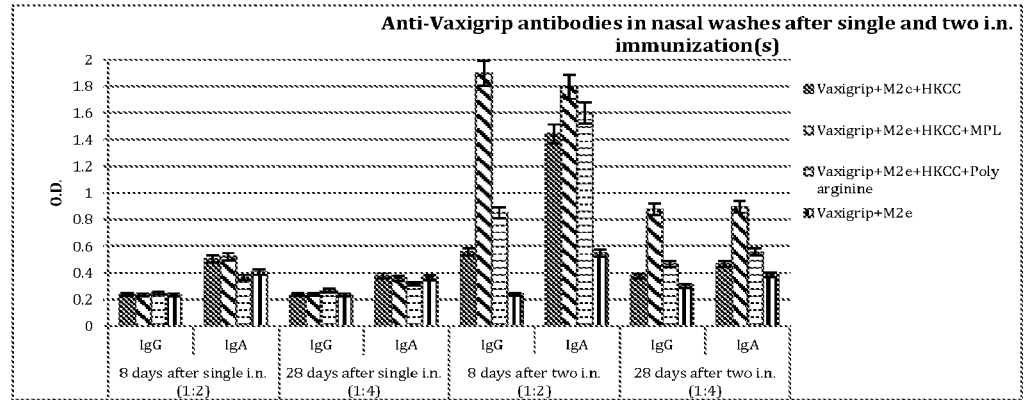
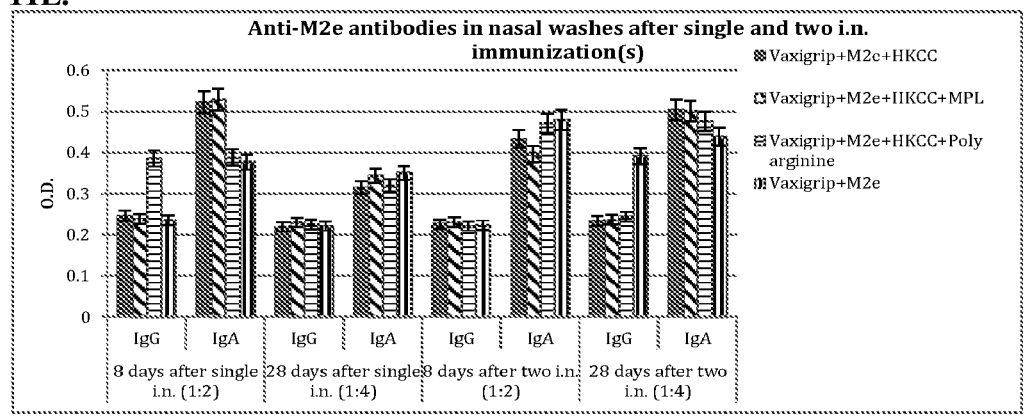
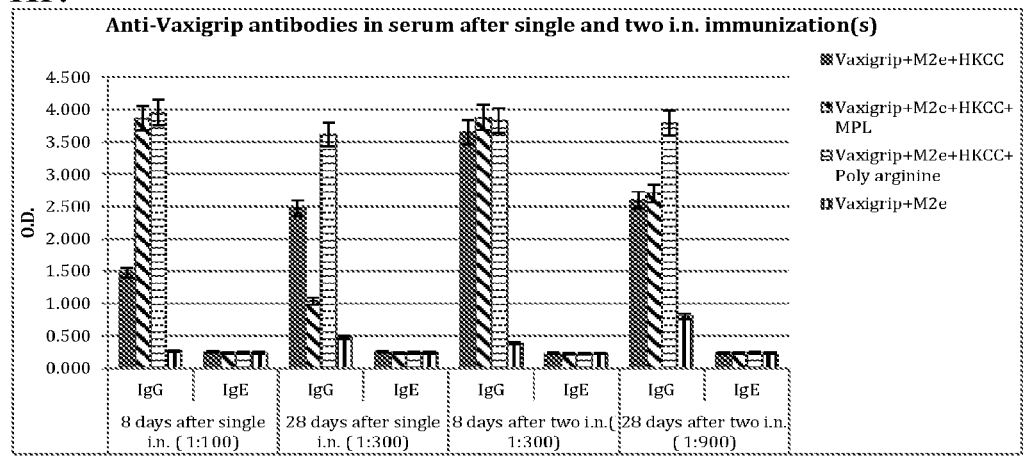
Figure 11D-F

Figure 13

14A.
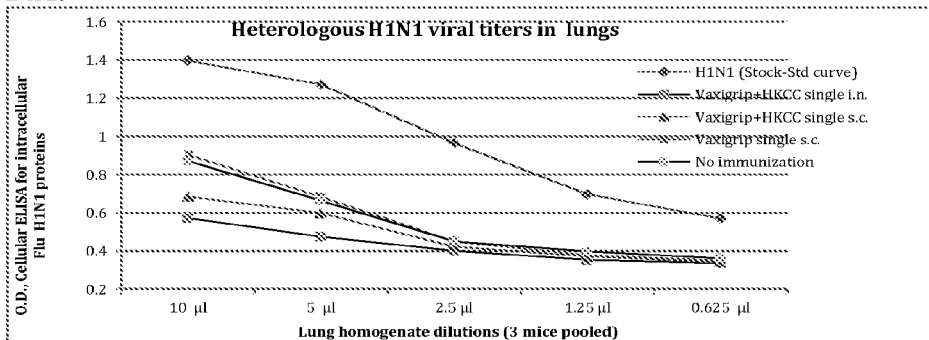
14B.
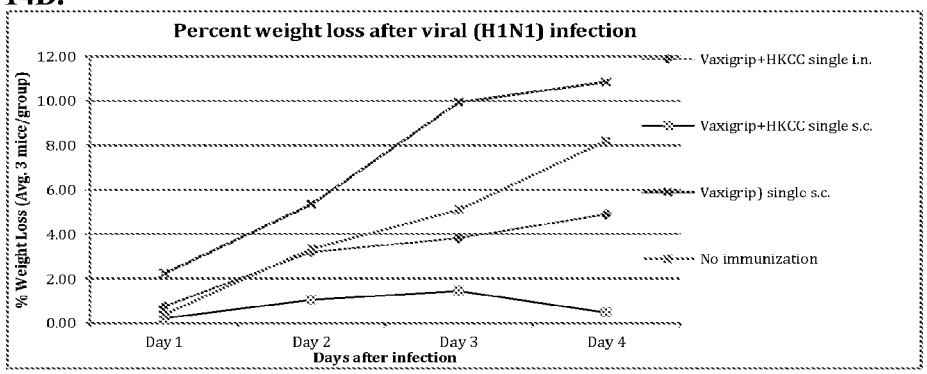
14C.
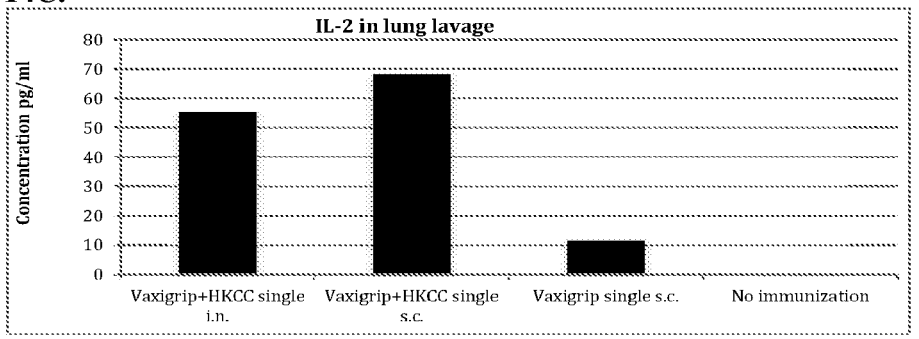
14D.
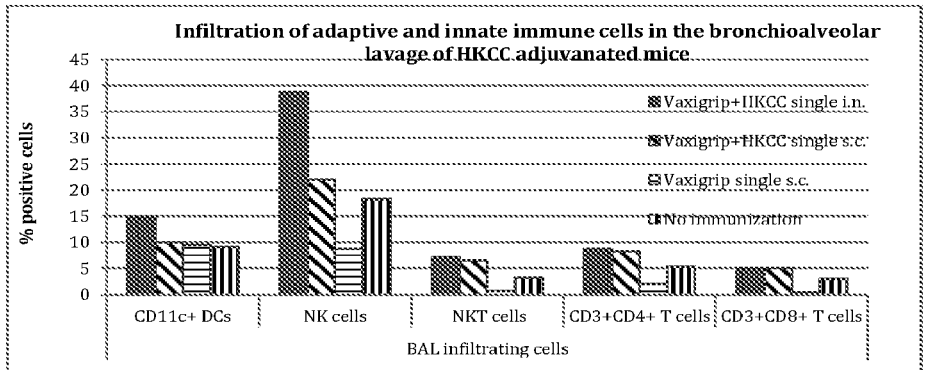
Figure 14A-D

15A.
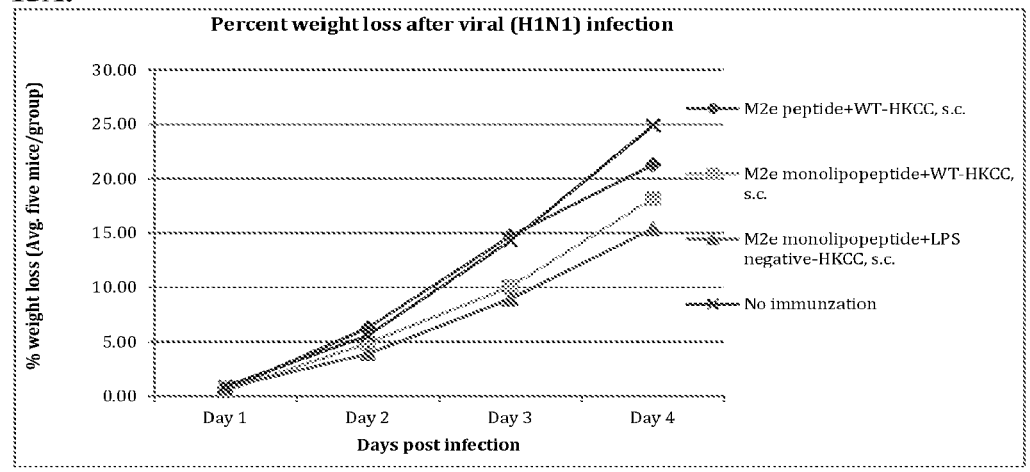
15B.
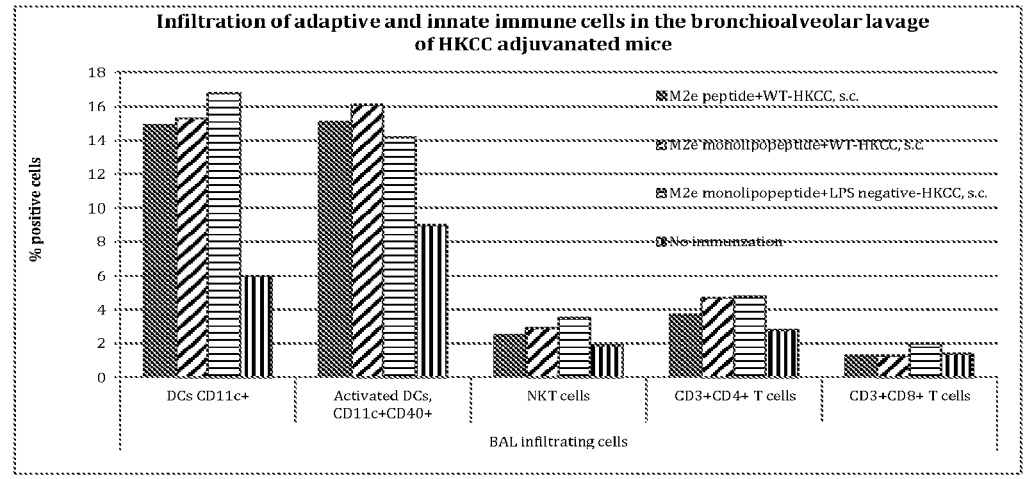
Figure 15A,B

16A.
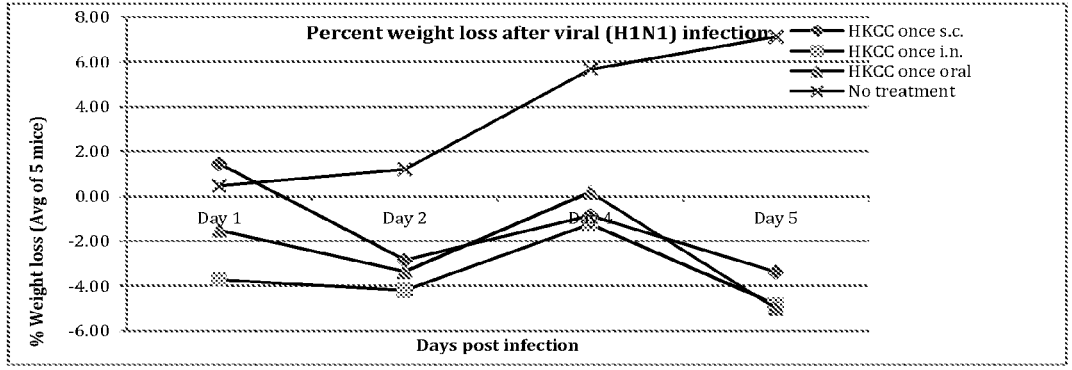
16B.
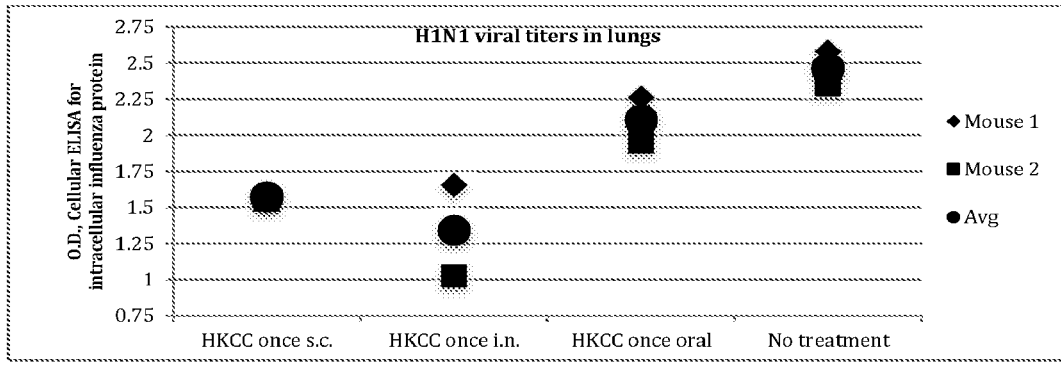
16C.
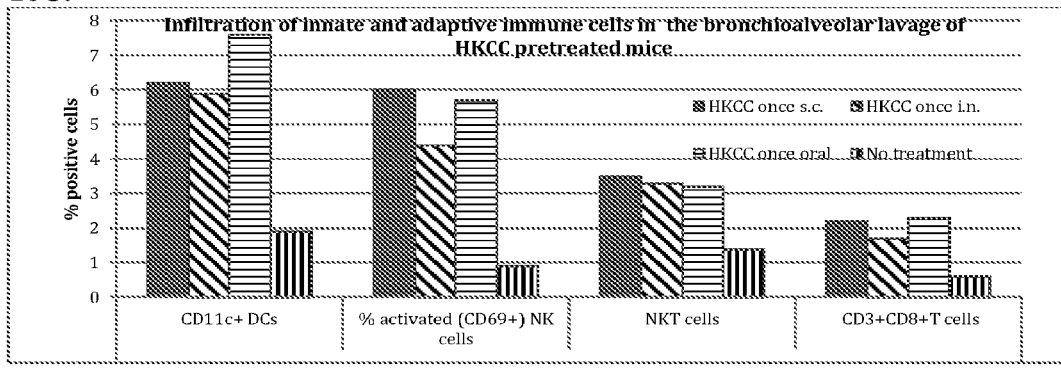
16D.
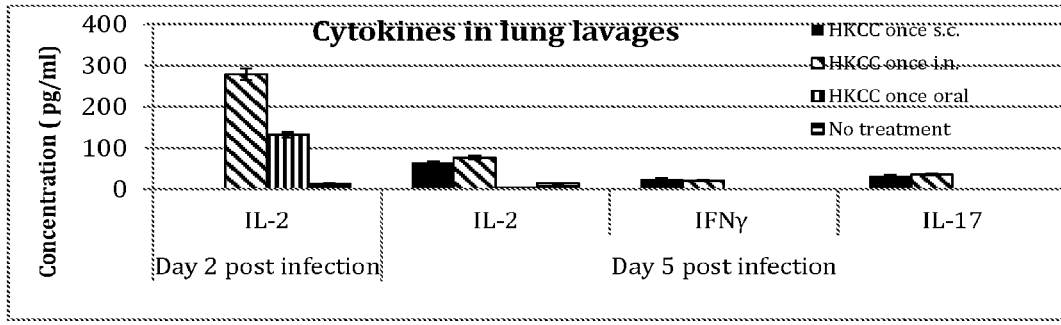
Figure 16A-D

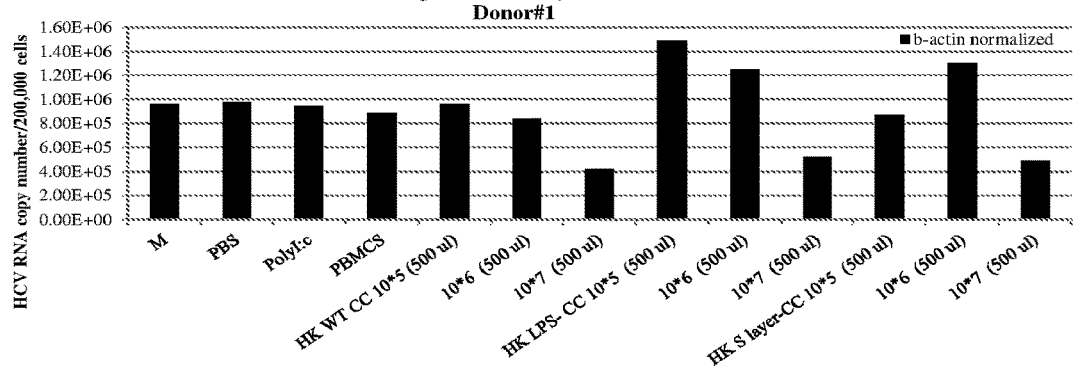
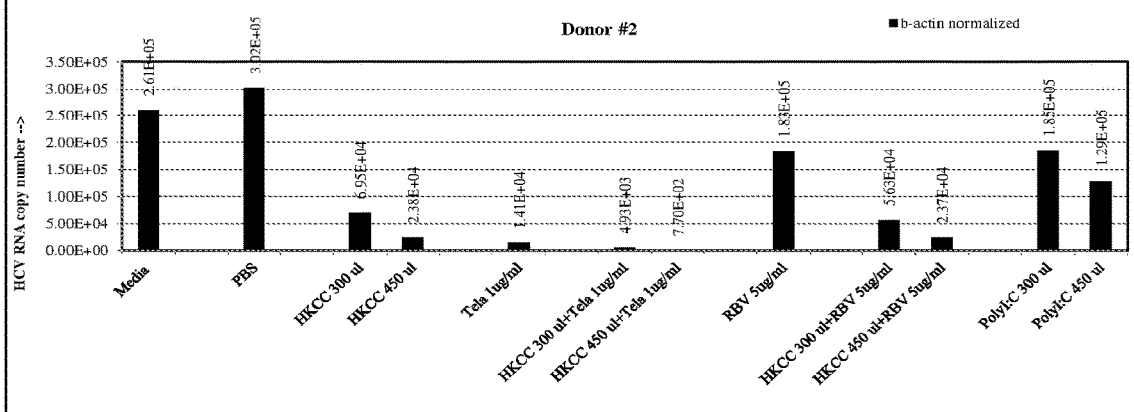
Figure 18A, B

22A.
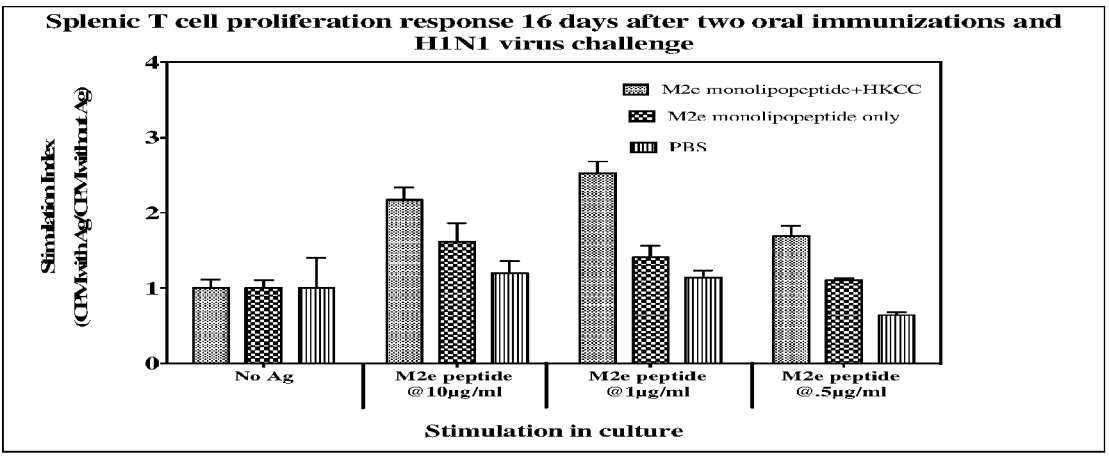
22B.
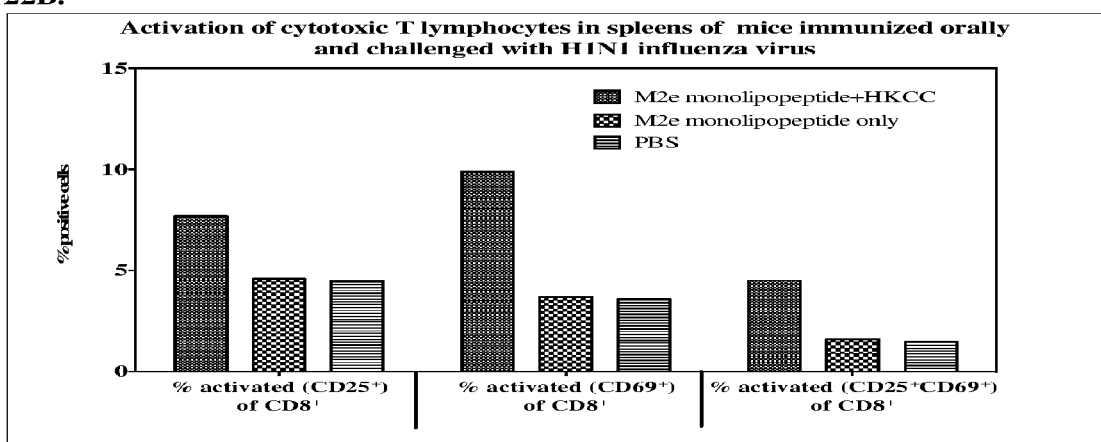
22C.
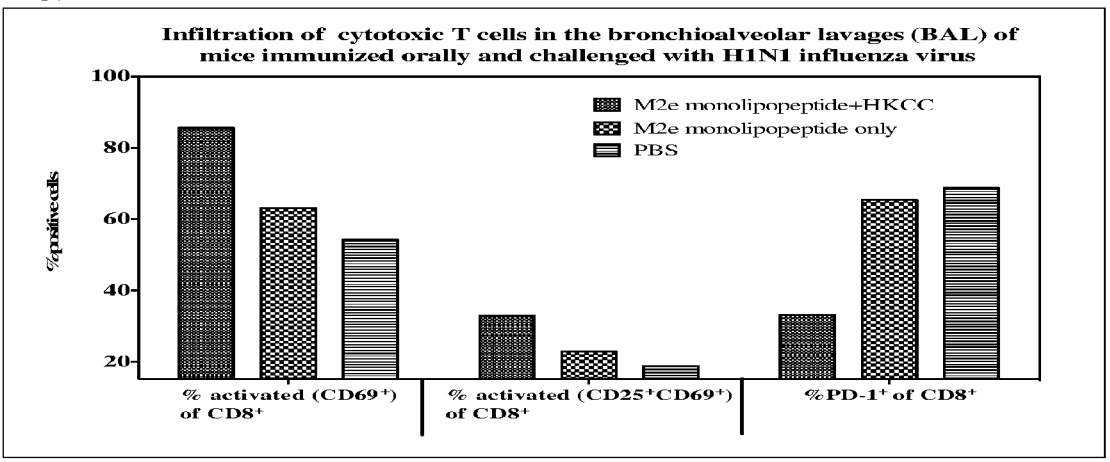
Figure 22 A-C

24.
Spleen and lymph nodes T cell proliferation, after single s.c. immunization and challenge with heterologous H1N1 influenza virus

26 A.
Anti-Vaxigrip antibodies in serum after single subcutaneous immunization and challenge with H1N1 influenza infection

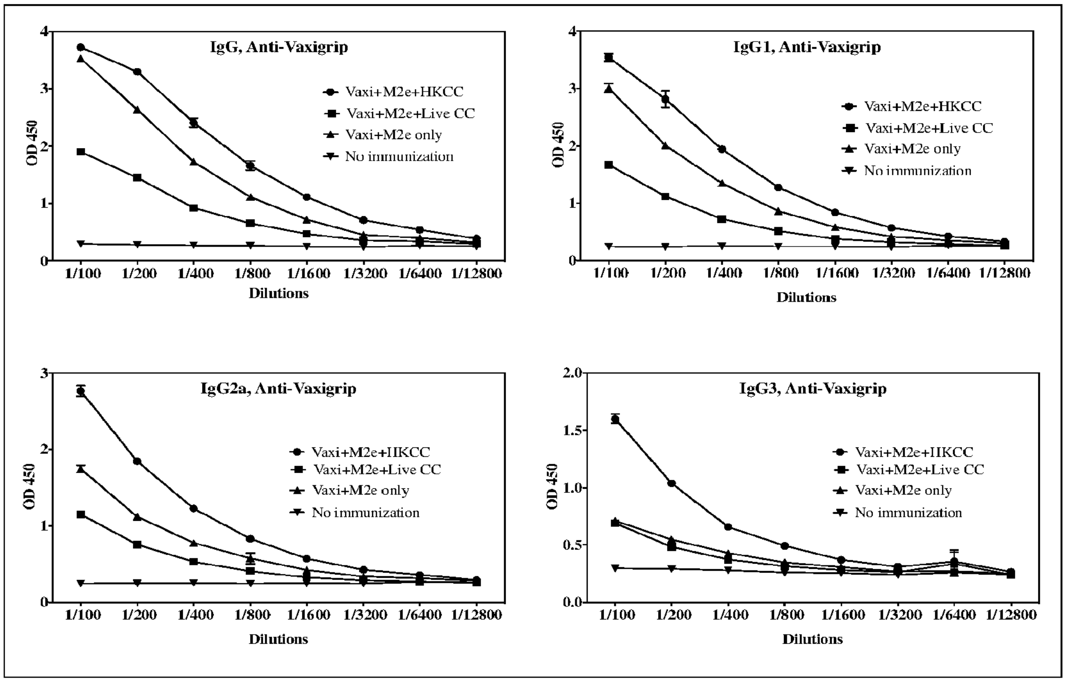

26B. Anti-M2e antibodies in serum after single subcutaneous immunization and challenge with H1N1 influenza infection

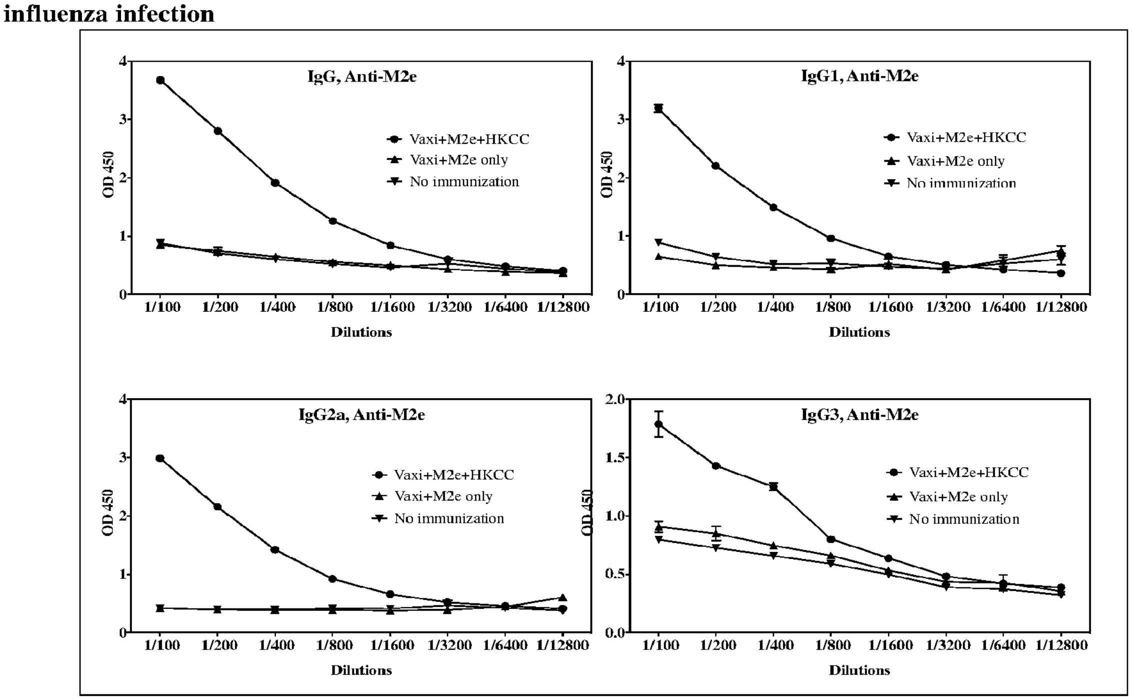

Figure 26 A,B

IMMUNOMODULATORY COMPOSITIONS AND METHODS OF USE THEREOF

CROSS-REFERENCE

This application is a continuation of U.S. patent application Ser. No. 15/108,744 filed Jun. 28, 2016, which is a national phase filing under 35 U.S.C. § 371 of International Application No. PCT/IB2015/050108 filed Jan. 7, 2015, which claims the benefit of U.S. Provisional Patent Application No. 61/924,607, filed Jan. 7, 2014, each of which is incorporated herein by reference in its entirety.

INTRODUCTION

*Caulobacter crescentus* is non-pathogenic, harmless, aquatic, gram-negative bacterium that grows at ~23° C. in many soil and freshwater environments *Caulobacter* has been studied for nearly 50 years. The main laboratory strain (*C. crescentus* CB15) is well characterized genetically and biochemically, and the genome of *C. crescentus* has been sequenced. Caulobacters are readily grown using standard laboratory equipment. They can also be easily grown in commercial fermenters to at least 30 ODs in animal protein free, defined minimal media.

There is a need in the art for safe and effective vaccines that induce both cellular and humoral immune responses. There is a need in the art for immunomodulatory compositions and adjuvants that can be used to treat infections, cancers, and autoimmune diseases.

SUMMARY

The present disclosure provides immunomodulatory compositions comprising heat-killed *Caulobacter crescentus* (HKCC). Immunomodulatory compositions of the present disclosure are useful for modulating an immune response in an individual. The present disclosure thus provides methods of modulating an immune response in an individual, involving administering an immunomodulatory composition comprising HKCC to the individual.

BRIEF DESCRIPTION OF THE DRAWINGS

FIGS. 2A-E illustrate the effect of live *Caulobacter crescentus* (CC) and HKCC on antigen-specific cellular immune responses against OVA. Groups of five C57/b16 mice were immunized with live CC or HKCC at $50 \times 10^6$ CFU/mouse with OVA (20 μg/mouse) in 100 μl total volume/mouse by the subcutaneous (s.c.) route at the base of the tail on days 0 and 14. Mice were euthanized 2 wks after immunization. Values are the mean of triplicates with ±SD. HKCC stimulates robust cell mediated (CD4, CD8) immunity against chicken ovalbumin (OVA) antigen as compared to live CC. 2A. T cell proliferative response from spleen; 2B. T cell proliferative response from lymph nodes and 2C. GrB producing antigen specific CTLs. 2C: Frequency of GrB-producing cells, by ELISPOT, two weeks after s.c. immunization with OVA. 2D: spleen T cell proliferation after a single s.c. injection of OVA. 2E: Serum IgG (left panel) and serum IgGa) right panel, one week after a single s.c. immunization.

FIGS. 3A-L depicts the effect of HKCC as an adjuvant for therapeutic HBV vaccine to induce cellular and humoral immune responses. Antigen specific T cell (CD4+, CD8+) and antibody responses following two intranasal immunizations (at 14 day intervals) of C57/b16 male mice with a mixture of recombinant HBV core antigen (5 μg/mouse) and HKCC ($50 \times 10^6$ CFU/mouse). Values are the mean of triplicates with ±SD. 3A. HBV core antigen specific T cell proliferation one week after two immunizations; 3B. HBV core antigen specific T cell proliferation three weeks after two immunizations; 3C. IFN-gamma production; 3D. IL-12 production; 3E. IFN-gamma production; 3F. Number of GrB producing T cell spots; 3G. HBV core antigen specific serum IgG responses; 3H. HBV core antigen specific serum IgG2a responses; 3I. HBV core antigen specific lung IgG responses one wk after two immunizations; 3J. HBV core antigen specific lung IgA responses one wk after two immunizations; 3K. HBV core antigen specific lung IgG responses three wk after two immunizations; 3L. HBV core antigen specific lung IgA responses three wk after two immunizations.

FIGS. 5A-C depict the effect of HKCC as an adjuvant for tuberculosis vaccine and leads to reduction of mycobacterial load in lungs, liver and spleen. Mice were immunized twice subcutaneously (at 12 days intervals) with a mixture of 7 monolipopeptides (Ag85B 68-88, 93-112, 126-142, 143-167, 199-218, 240-251, 257-273, 5 μg each peptide/mouse) and HKCC ($50 \times 10^6$ CFU/mouse). The immunized mice were challenged with $0.5 \times 10^6$ cfu/mouse *Mycobacterium tuberculosis* (Mtb) H37Ra six weeks after second immunization. Infected mice were euthanized three weeks after Mtb challenge. Lungs, liver and spleen were collected from individual mice and used for CFU assay. The CFU data are shown for five individual mice in each experimental group in 5A. lungs, 5B. liver, and 5C. spleen.

FIGS. 6A-D depict the effect of HKCC as an adjuvant for prophylactic vaccine for solid tumor to reduce EL-4 tumors after a single subcutaneous (s.c.) immunization. Groups of five C57Bl6 mice were immunized once subcutaneously with a mixture of irradiated EL-4 cells ($1 \times 10^6$/mouse) and HKCC ($50 \times 10^6$ CFU/mouse). The immunized mice were challenged with $0.25 \times 10^6$ EL-4 cells/mouse in 100 μl PBS s.c. in the lower left flank eight days after immunization. Tumor growth was measured for 28 days after challenge using digital calipers in two perpendicular directions, and mice were humanely euthanized. Tumor area were calculated as length×width (in mm). The data represent 6A. tumor progression; 6B. tumor mass; 6C. EL-4 specific lymph node T cell proliferation response and 6D. EL-4 specific serum IgG response. Tumor data are shown for five individual mice in each experimental group and immune responses are from five pooled mice.

FIGS. 7A-C depict the effect of HKCC as an adjuvant for prophylactic vaccine for lung cancer to reduce in lung metastases after a single s.c. immunization. Groups of five C57Bl6 mice were immunized once subcutaneously with a mixture of irradiated B16 cells ($1\times10^6$/mouse) and HKCC ($50\times10^6$ CFU/mouse). The immunized mice were challenged with $0.4\times10^6$ B16 cells/mouse in 50 μl PBS intravenously in the tail vein eight days after immunization. Mice were humanely euthanized 12 days after tumor challenge. The data represent A. lung tumor nodules in both treated and untreated groups; B. lungs weight; and C. B16 cell lysate specific serum IgG response. Tumor data are shown for five individual mice in each experimental group and immune responses are from five pooled mice.

FIGS. 8A-C illustrate antitumor activity of HKCC against B16 melanoma lung metastasis after two s.c. treatments. Groups of four C57Bl6 mice were challenged with $0.4\times10^6$ B16 cells/mouse in 100 μl PBS intravenously in the tail vein. Starting from day 3 post tumor challenge, HKCC ($50\times10^6$ cfu/mouse) was administered s.c. once weekly for a total of two weeks. Three days after the last treatment, mice were euthanized. The data represent 8A. lung tumor nodules in both treated and untreated groups; 8B. lung weights and 8C. B16 cell lysate specific serum IgG response. Tumor data are shown for four individual mice in each experimental group and lung weights represent Avg±SD from four mice.

FIGS. 9A-B depict efficacy of immunotherapeutic treatment with HKCC in mice challenged with EL-4 tumor cells. Groups of five C57Bl6 mice were challenged with $0.25\times10^6$ EL-4 cells/mouse in 100 μl PBS s.c. in the lower left flank. Six days after tumor challenge, mice were treated once weekly subcutaneously with HKCC ($50\times10^6$ CFU/mouse) or PBS control three times. Tumor growth was measured for 28 days after challenge using digital calipers in two perpendicular directions, and mice were humanely euthanized. Tumor area were calculated as length×width (in mm). The data represent: 9A, tumor progression; 9B, PD-1 expression on immune cells in spleens. Tumor data shown represent mean from five mice in each experimental group and PD-1 data are from five pooled spleens from mice.

FIGS. 10A and 10B illustrate the effect of live CC and HKCC on antigen-specific cellular (CD4+ and CD8+ T cells) immune responses against TIV (seasonal) influenza vaccine upon single mucosal (i.n.) immunization with a low dose of antigen. Groups of five C57/b16 mice were immunized by the intranasal route with live CC or HKCC at $50\times10^6$ CFU/mouse with Vaxigrip (1.6 μg/mouse) in 30 μl total volume/mouse. In the control no adjuvant group, Vaxigrip (1.8 μg/mouse) alone was administered subcutaneously. Mice were euthanized 8 days after immunization. Values are the mean of triplicates with ±SD. The data represent 10A. antigen specific T cell proliferation and 10B. antigen specific GrB producing CTLs.

FIGS. 11A-G depict the effect of HKCC in inducing long-lasting antigen-specific humoral and cellular immune responses against co-administration of multiple antigens of influenza upon mucosal (i.n.) immunizations with low doses of antigens. Antigen specific T cell and antibody responses were determined following one or two intranasal immunization(s) (at 21 days interval) of C57/b16 male mice with a mixture of seasonal TIV influenza vaccine (Vaxigrip 1.8 Kg/mouse), M2e-monolipo peptide (20 μg/mouse) and HKCC ($50\times10^6$ CFU/mouse). HKCC when combined with other adjuvants e.g., MPL (a TLR-4 agonist) (5 μg/mouse) or a polymeric compound e.g., poly-L-arginine hydrochloride (100 μg/mouse), potentiates immune responses. No IgE were developed against antigens at both early and later time points. Values are the mean of triplicates with ±SD. 11A. Vaxigrip and M2e antigens specific T cell proliferation 8 days after two immunizations; 11B. anti-Vaxigrip antibody responses in lung lavage; 11C. anti-M2e antibodies in lung lavage; 11D. anti-Vaxigrip antibody responses in nasal lavage; 11E. anti-M2e antibodies in nasal lavage; 11F. anti-Vaxigrip antibody responses in serum; 11G. anti-M2e antibodies in serum.

FIG. 13 depicts the effect of S-layer negative HKCC on antigen-specific T cell response against multiple antigens of influenza upon mucosal (i.n.) immunizations. Antigen specific T cell responses following intranasal immunizations of C57/b16 male mice with a mixture of seasonal TIV influenza vaccine (Vaxigrip 1.8 μg/mouse), M2e-monolipo peptide (20 pig/mouse) and S-layer negative HKCC ($50\times10^6$ CFU/mouse). Values are the mean of triplicates. Vaxigrip and M2e antigens specific T cell proliferation 8 days after two immunizations (at 21 days interval).

FIGS. 14A-D depict enhancement of spectrum of protection of seasonal flu TIV vaccine (Vaxigrip) upon single mucosal or s.c. immunization from heterologous virus infection. Groups of three BALB/c female mice were immunized by the intranasal (1.8 μg/mouse Vaxigrip) or s.c. (3.6 μg/mouse Vaxigrip) routes with HKCC ($50\times10^6$ CFU/mouse) in 30 and 100 μl total volume/mouse, respectively. In the control no adjuvant group, Vaxigrip (3.6 μg/mouse) alone was administered subcutaneously. Eight days after immunization, mice were challenged intranasally with 30 μl/mouse of stock of H1N1 (PR8) virus and daily weights of individual mouse were recorded. Four days after infection, mice were euthanized and viral titers were determined in lung homogenates. BAL was collected to determine cytokine and infiltrating cells. The data demonstrates 14A. viral titers in the lungs of infected mice; 14B. % weight loss after infection; 14C. production of cytokine IL-2 in BAL after infection; and 14D. infiltration of various innate and adaptive immune cells in BAL of the immunized and unimmunized groups.

FIGS. 15A and 15B depict the effect of a single subcutaneous immunization of a poorly immunogenic antigen (M2e) adjuvanted with WT-HKCC or LPS-negative HKCC on weight-loss after influenza virus infection. Groups of five BALB/c female mice were immunized subcutaneously with M2e peptide or lipopeptide (25 μg/mouse) and HKCC or LPS-negative HKCC ($50\times10^6$ CFU/mouse) in 100 μl total volume/mouse at the base of the tail. Eight days after immunization, mice were challenged intranasally with 30 μl/mouse of stock of H1N1 (PR8) virus and daily weights of individual mouse were recorded. Four days after infection, mice were euthanized and BAL was collected to determine infiltrating cells. The data demonstrates 15A. percent weight loss after infection; and 15B. infiltration of various innate and adaptive immune cells in BAL of the immunized and unimmunized groups.

FIGS. 16A-D depict the effect of prophylactic immunotherapy with HKCC by s.c., i.n., or oral route(s) on protection from viral (H1N1) infection. Groups of five BALB/c female mice were treated with HKCC ($50\times10^6$ cfu/mouse)

by s.c. (100 µl volume/mouse at the base of the tail), i.n. (30 µl total/mouse) or oral route in (100 µl volume/mouse). Twenty four hours after treatment, mice were challenged intranasally with 30 µl/mouse of stock of H1N1 (PR8) virus and daily weights of individual mouse were recorded. Two and five days after infection, mice were euthanized and BAL samples and lungs were collected. The data demonstrates 16A. % weight loss after infection; 16B. viral titers in lungs; 16C. infiltration of various innate and adaptive immune cells in BAL and 16D. cytokines present in BAL.

Figure 17:
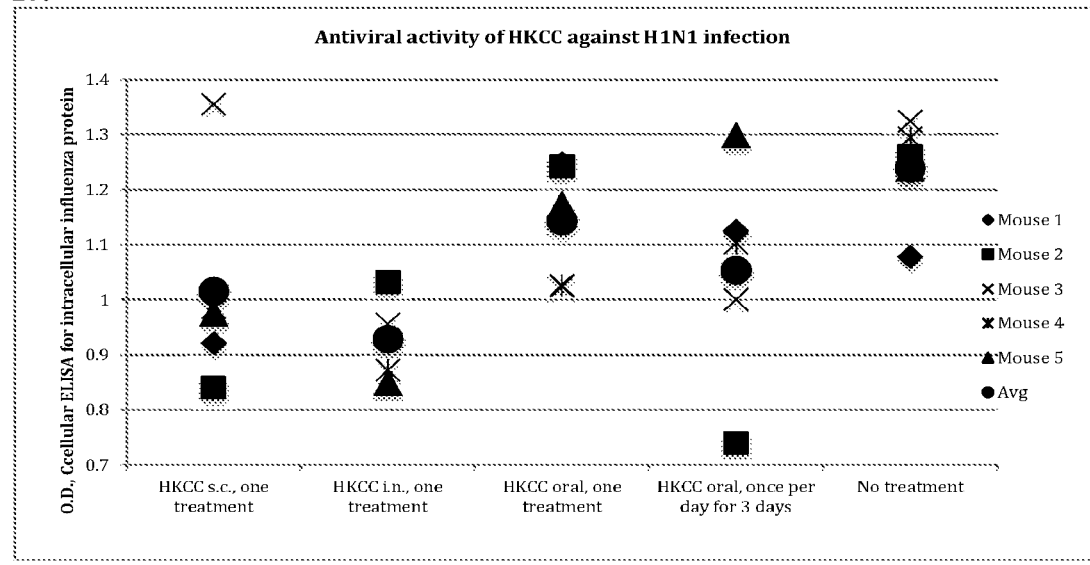

FIG. 17 depicts immunotherapeutic antiviral effect of HKCC against H1N1 infection. Groups of five BALB/c female mice were challenged intranasally with 30 µl/mouse of stock of H1N1 (PR8). Twenty-four hours after the infection, mice were treated with HKCC ($50 \times 10^6$ cfu/mouse) subcutaneously (100 µl volume/mouse at the base of the tail), intranasally (30 µl total/mouse) or orally (100 µl volume/mouse). Five days after infection, mice were euthanized and lungs were collected to determine viral titers. The data demonstrate viral titers in lungs of individual mice and the average of five mice.

FIGS. 18A and 18B depict inhibition of HCV 1a RNA replication by supernatants of human PBMCs stimulated with HKCC. Human PBMCs from a single donor #1 were stimulated with $10^5$, $10^6$ or $10^7$ HKCC/ml (Wild Type (HK WT CC), LPS negative (HK LPS-CC) and S layer negative (HK S layer-CC) (FIG. 18A), followed by collecting the supernatant at 24 hrs. The supernatant (500 µl/ml) was then added to the HCV1a replicon containing Huh-7 cells, incubated for 5 days and cells were examined for HCV RNA copy numbers by real-time RT-PCR (FIG. 18A) Inhibition of HCV 1a RNA replication upon single treatment with supernatants (300 µl and 450 µl) of human PBMCs stimulated with $10^7$ HKCC/ml with or without telaprevir (Tela) or ribavirin (RB V) and incubation for 5 days, followed by HCV RNA quantification by real-time RT-PCR (FIG. 18B). PolyI:C stimulated PBMC media was used as controls. M stands for media control (untreated cells) and PBMCs or PBS represents supernatant from unstimulated PBMCs. The data represent means of triplicates.

Figure 19:
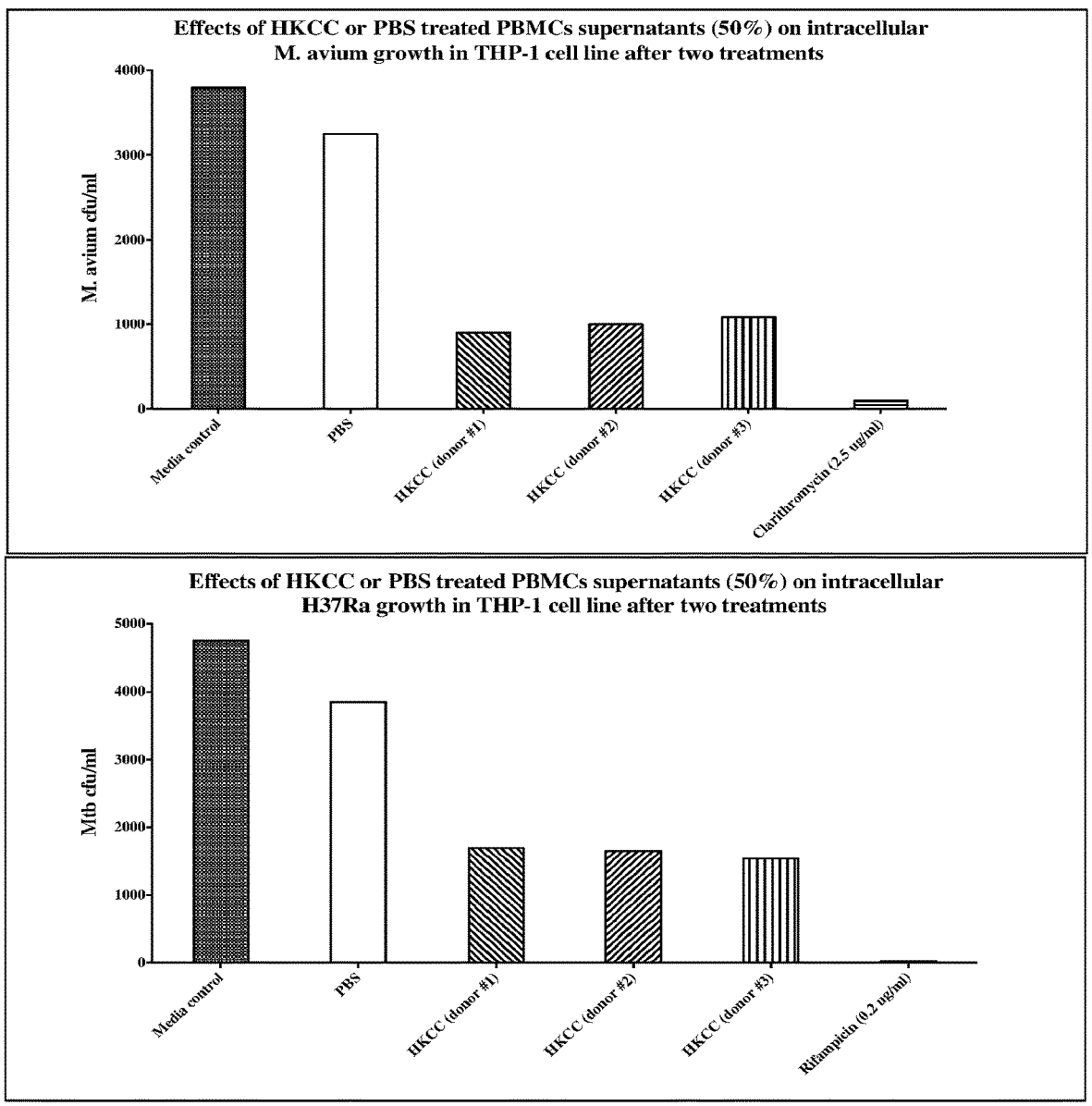

FIG. 19 demonstrates that HKCC induces cytokines from human PBMCs which can inhibit intracellular bacterial replication. Human monocytic cell line (THP-1) was infected with *M. avium* or Mtb H37Ra using published procedures, followed by two treatments (on days 0 and 4) with supernatants (50%) collected from human PBMCs treated for 24 hrs with HKCC or PBS in 24 well plates. Supernatants collected from three different donor PBMCs stimulated with HKCC were tested as donors #1, #2 and #3. In controls clarithromycin or rifampicin were added directly to infected THP-1 cells. Five days after second treatment, THP-1 were collected, lysed and plated on 7H11 agar plates to determine bacterial CFUs.

Figure 20:
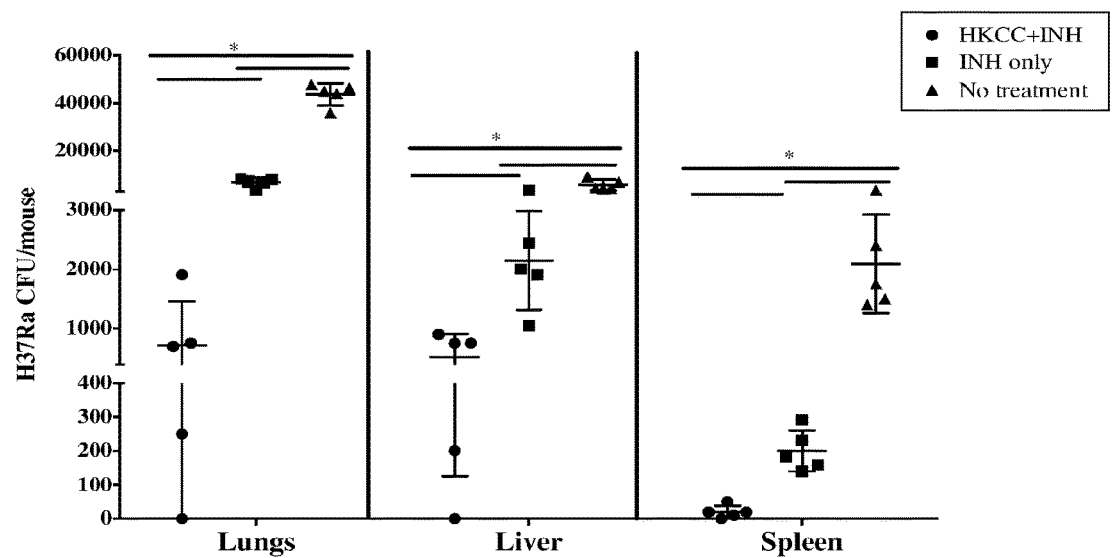

FIG. 20 illustrates the effect of HKCC in combination with a chemotherapeutic drug in reducing bacterial burden. Groups of 5 BALB/c female mice were challenged with H37Ra ($0.5 \times 10^6$ cfu/mouse) intravenously. Five days post infection, mice were treated with HKCC ($50 \times 10^6$ cfu/mouse) and INH (20 µg/mouse), INH alone or PBS using a schedule shown in the figure. Mice were euthanized 2 days after the last treatment. Spleens, lungs and liver were collected to determine bacterial loads using CFU assay.

Figure 21:
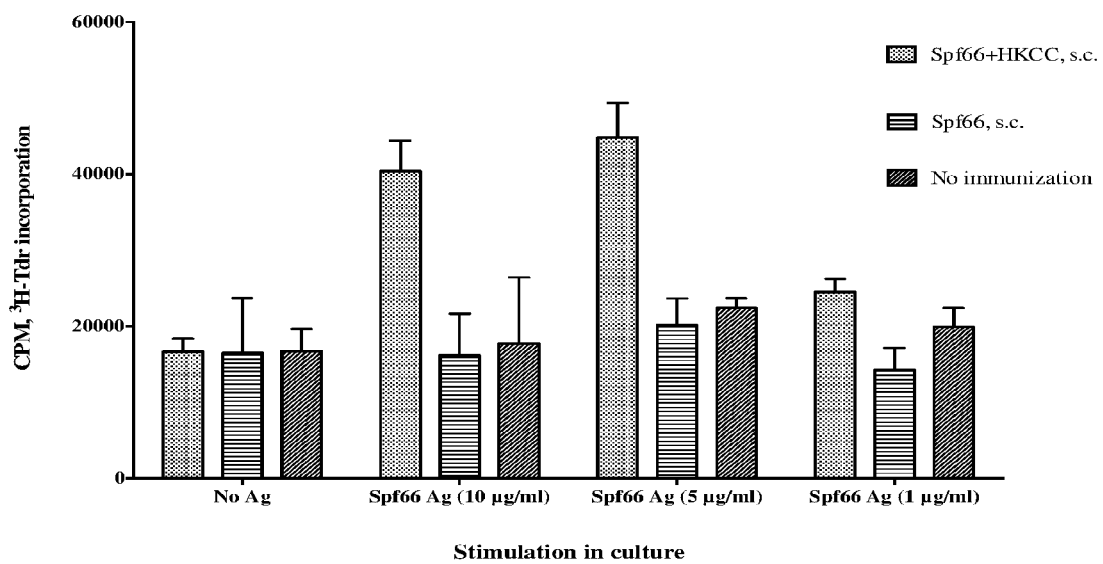

FIG. 21 demonstrates that HKCC enhances T cell responses against malaria-derived antigen Spf66. A group of five C57/b16 male mice were immunized subcutaneously twice (at 12 days interval) with HKCC ($50 \times 10^6$/mouse)+Spf66 peptide (20 µg/mouse), Spf66 peptide (20 µg/mouse) alone or PBS. Mice were euthanized eight days after second immunization. The data represent malaria antigen (Spf66)-specific T cell proliferation from splenocytes; the values are the mean of triplicates ±SD.

FIGS. 22A-C demonstrate that HKCC induces antigen-specific T cell responses upon oral immunization and viral challenge. Groups of five BALB/c female mice were immunized twice orally (at 12 days interval) with M2e lipopeptide (50 µg/mouse)+HKCC ($50 \times 10^6$ CFU/mouse), M2e lipopeptide (50 µg/mouse) alone or PBS in 200 µl total volume/mouse. Twelve days after immunizations, mice were challenged intranasally with 30 µl/mouse of stock of H1N1 (PR8) virus. Four days after infection, mice were euthanized. Spleens and BALs were collected. Antigen specific T cell proliferation (22A), activation of CTLs in splenocytes (22B) and infiltration of activated CTLs in BALs (22C) are shown.

Figure 23:
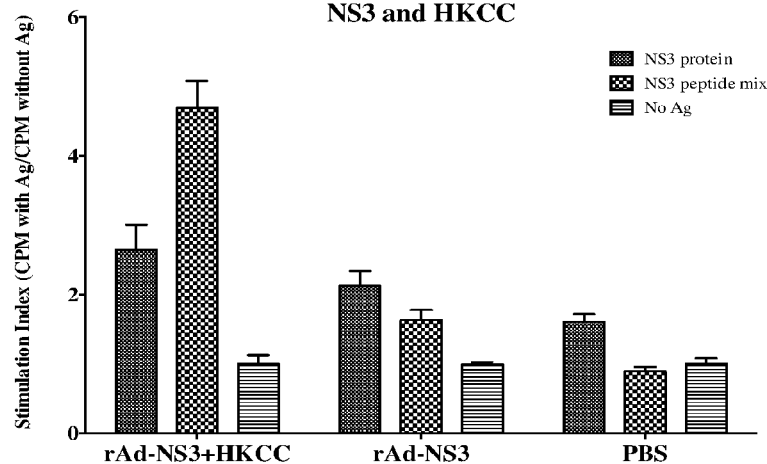

FIG. 23 demonstrates cellular immune responses generated against HCV NS3 and a pool of 15-aa long peptides from HCV-NS3 in mice immunized with adenoviral vector (rAd-NS3) in the absence or presence of HKCC. Groups of five C57bl/6 female mice were immunized twice (at 14 days interval) with $2 \times 10^7$ pfu/mouse adeno vector expressing NS3 coding region (rAd-NS3) with or without HKCC ($50 \times 10^6$ cfu/mouse) intramuscularly (i.m.) in quadriceps muscles in a total volume of 150 microlitre/mouse. PBS-immunized mice were used as negative control. Eight days after second immunization, mice were euthanized and spleens were collected. Enriched T cells ($4 \times 10^5$/well) from spleens were cultured with irradiated syngeneic spleen cells as APCs ($4 \times 10^5$/well) and recombinant HCV NS3 protein or HCV NS3 derived synthetic peptides pool (5 µg/m') for four days. Proliferation of T cells was examined by $^3$H thymidine incorporation assay, and stimulation indices were calculated using the formula (SI=CPMs in the presence of antigen/ CPMs in the absence of antigen). All data represent mean±standard deviations of triplicate wells.

Figure 24:
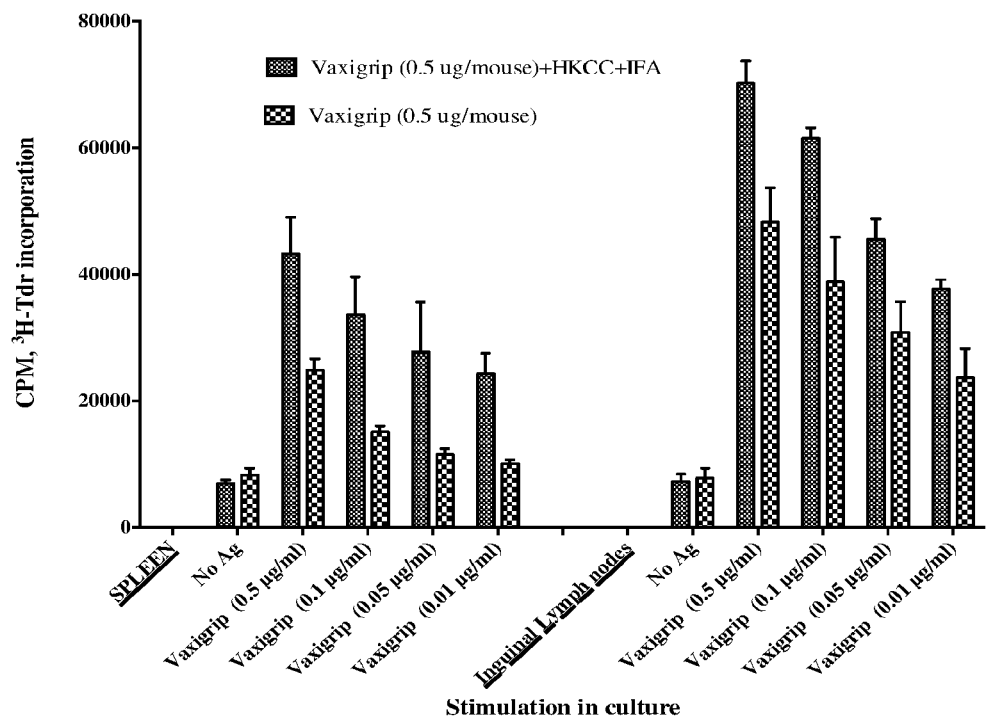

FIG. 24 demonstrates that HKCC mixed with IFA elicits strong T cell responses following single subcutaneous immunization with a low dose of antigen (Vaxigrip) and challenge with heterologous (H1N1) influenza virus. Groups of five BALB/c mice were immunized by the subcutaneous route with HKCC at $50 \times 10^6$ CFU/mouse, IFA (20 ul) with Vaxigrip (0.5 µg/mouse) in 100 µl total volume/mouse. In the control no adjuvant group, Vaxigrip (0.5 µg/mouse) alone was administered subcutaneously. Eight days after immunization, mice were challenged with H1N1 influenza virus, and euthanized three days after infection. The data represent antigen specific T cell proliferation from splenocytes and inguinal lymph nodes. Values are the mean of triplicates with ±SD.

Figure 25:
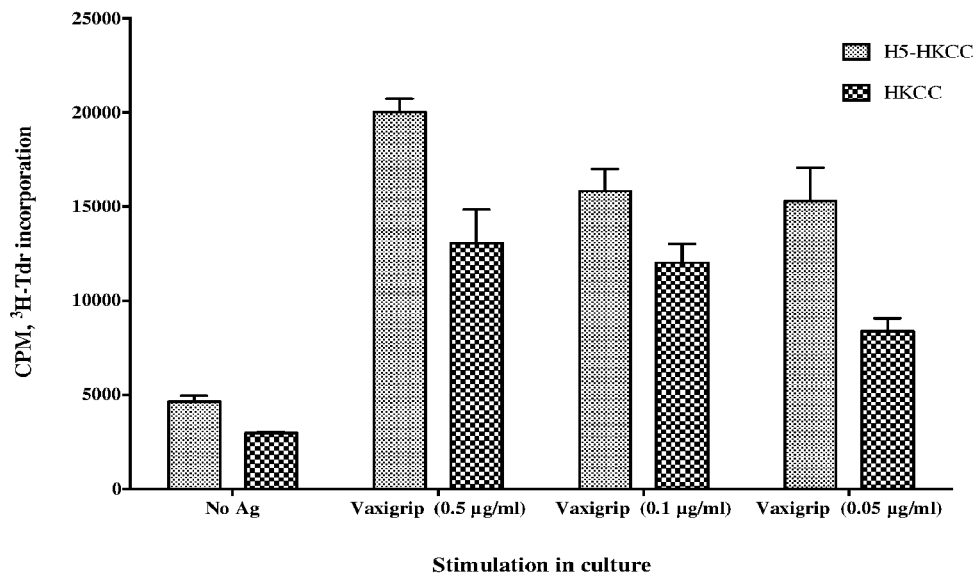

FIG. 25 depicts that recombinant HKCC containing hemagglutinin protein from influenza virus (H5-HKCC) after intranasal immunization induces influenza antigens' specific T proliferative responses. Groups of five BALB/c female mice were immunized with recombinant H5-HKCC or wild-type HKCC ($50 \times 10^6$ cfu/ml) twice intranasally (at 8 days interval) and challenged with H1N1 influenza 12 days after second immunization. Mice were euthanized 3 days after infection. The data represent influenza antigens (vaxigrip) specific T cell proliferation from splenocytes and the values are the mean of triplicates with ±SD.

FIGS. 26A and 26B illustrate the effect of live CC and/or HKCC on antigen-specific humoral immune responses against multiple antigens of influenza upon single s.c. immunization and heterologous influenza virus challenge. Groups of five BALB/s female mice were immunized with a mixture of seasonal TTV influenza vaccine (Vaxigrip 1.0 µg/mouse), M2e-monolipo peptide (20 µg/mouse) and HKCC (50×10$^6$ CFU/mouse); Vaxigrip (1.0 µg/mouse), M2e-monolipo peptide (20 µg/mouse) and live CC (50×10$^6$ CFU/mouse); Vaxigrip (1.0 µg/mouse), M2e-monolipo peptide (20 µg/mouse); or PBS once subcutaneously. Mice were challenged intranasally with H1N1 influenza virus eight days after immunization. Sera samples were collected 4 days after infection (11 days after single immunization) and examined for antibodies against Vaxigrip (26A) and M2e (26B).

DEFINITIONS

The terms "individual," "host," "subject," and "patient" are used interchangeably herein, and refer to mammals, including, but not limited to, humans, non-human primates (e.g. simians), non-human mammals (e.g., mammalian livestock animals (e.g., bovine, porcine, caprine, and ovine animals)), and mammalian pets (e.g., cats, dogs); fish; and birds (e.g., chicken).

A "biological sample" encompasses a variety of sample types obtained from an individual. The definition encompasses blood, serum, plasma, and other liquid samples of biological origin; solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as epithelial cells. The term "biological sample" encompasses a clinical sample, and also includes cells in culture, cell supernatants, organs, tissue samples, lung biopsy samples, lung epithelial cells, gastrointestinal epithelial cells, gastrointestinal tract tissue samples, bronchoalveolar lavage (BAL) fluid samples, nasal lavage fluid samples, blood, plasma, serum, cerebrospinal fluid, fecal samples, and the like.

An "immunomodulator" or "immunomodulatory agent" is any agent which does one or more of: restores depressed immune function, regulates abnormal immune function, enhances normal immune function, and provide desired immune response. Immune function includes one or more of: humoral (antibody-mediated) immunity, cellular immunity, and innate immunity. An "immunomodulalor" includes agents acting directly on the cells involved in the expression of immune response, or on cellular or molecular mechanisms, which, in turn, act to modify the function of cells involved in immune response. Augmentation of immune function may result from the action of an immunomodulatory agent to abrogate suppressive mechanisms derived by negative-feedback influences endogenous or exogenous to the immune system. Thus, immunomodulators can have diverse mechanisms of action.

An "adjuvant" is any agent which is capable of potentiating an immune response and are, therefore, one class of immunopotentiators (Stites and Ten, *Basic and Clinical Immunology*, 7$^{th}$ Ed., Appleton and Lange Norwalk Conn. pp. 797, 1991). Adjuvants are used to increase the immune responses in vaccination in order to enhance the humoral and/or cell mediated immune responses.

A "vaccine" is intended to encompass a preventive vaccine or a therapeutic vaccine. A preventive vaccine is one that is given to stimulate an immune response to an antigen, so that if an individual subsequently is exposed to the antigen, the pre-formed immunity will protect the individual from the respective disease related to the antigen. A therapeutic vaccine is given to an individual who already has a disease associated with an antigen, wherein the vaccine can elicit an immune response or boost the individual's existing immunity to the antigen, to treat and/or ameliorate symptoms of the disease.

A "cytokine" means any secreted polypeptide that affects the functions of other cells, and is a molecule, which modulates interactions between cells in the immune or inflammatory response. A cytokine includes, but is not limited to monokines, chemokines, and lymphokines, regardless of which cells produce them.

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, bi-specific antibodies, and fusion proteins comprising an antigen-binding portion of an antibody and a non-antibody protein. Also encompassed by the term are Fab', Fv, F(ab')$_2$, and or other antibody fragments that retain specific binding to antigen, and monoclonal antibodies. An antibody may be monovalent or bivalent.

A "therapeutically effective amount" or "efficacious amount" means the amount of a compound or agent that, when administered to a mammal or other subject for treating a disease, is sufficient to effect such treatment for the disease. The "therapeutically effective amount" will vary depending on the compound or agent, the disease and its severity and the age, weight, general health status, sex, etc., of the subject to be treated. In some cases, an "effective amount" of an agent is an amount that: 1) restores the immune function to normal levels; 2) increases immune function above normal levels; or 3) reduces immune function below a pathological level.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

A "pharmaceutically acceptable carrier or excipient" means a non-toxic solid, semi-solid, or liquid filler, diluent, encapsulating material or formulation auxiliary of any type. One skilled in the art of preparing formulations can readily select the proper form and mode of administration depending upon the particular characteristics of the gent selected, the disease state to be treated, the stage of the disease, and other relevant circumstances.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a heat-killed *Caulobacter crescentus*" includes a plurality of such heat-killed bacteria and reference to "the adjuvant" includes reference to one or more adjuvants and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides immunomodulatory compositions comprising heat-killed *Caulobacter crescentus* (HKCC). Immunomodulatory compositions of the present disclosure are useful for modulating an immune response in an individual. The present disclosure thus provides methods of modulating an immune response in an individual, involving administering an immunomodulatory composition comprising HKCC to the individual.

Immunomodulatory Compositions

The present disclosure provides immunomodulatory compositions comprising heat-killed *Caulobacter crescentus* (HKCC). HKCC in an immunomodulatory composition of the present disclosure are non-viable and are metabolically inactive. An immunomodulatory composition of the present disclosure can comprise a cocktail of one or more different strains of *Caulobacter crescentus* bacteria.

HKCC-containing immunomodulatory compositions include the HKCC by itself with a pharmaceutically acceptable carrier or excipients for immunological adjuvant activity, including "adjuvanting" in which HKCC administration to a subject may be wholly independent of, and/or separated temporally and/or spatially from, administration to the subject of one or more antigens against which elicitation or enhancement of an immune response (e.g., an antigen specific response) in the subject is desired.

An immunomodulatory composition of the present disclosure can increase an immune response in an individual. In some cases, an effective amount of an immunomodulatory composition of the present disclosure is an amount that is effective, when administered in a single dose or in multiple doses, to increase the number of B cells in an individual. For example, in some cases, an effective amount of an immunomodulatory composition of the present disclosure is an amount that is effective, when administered in a single dose or in multiple doses, to increase the number of B cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the number of B cells in the individual in the absence of treatment with the immunomodulatory composition. In some cases, an effective amount of an immunomodulatory composition of the present disclosure is an amount that is effective, when administered in a single dose or in multiple doses, to increase the number of antigen-specific B cells in an individual. For example, in some cases, an effective amount of an immunomodulatory composition of the present disclosure is an amount that is effective, when administered in a single dose or in multiple doses, to increase the number of antigen-specific B cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the number of antigen-specific B cells in the individual in the absence of treatment with the immunomodulatory composition.

In some cases, an effective amount of an immunomodulatory composition of the present disclosure is an amount that is effective, when administered in a single dose or in multiple doses, to increase activity of B cells in an individual. For example, in some cases, an effective amount of an immunomodulatory composition of the present disclosure is an amount that is effective, when administered in a single dose or in multiple doses, to increase activation of B cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, at least 25-fold, at least 50-fold, at least 100-fold, or more than 100-fold, compared to the activation level of B cells in the individual in the absence of treatment with the immunomodulatory composition.

In some cases, an effective amount of an immunomodulatory composition of the present disclosure is an amount that is effective, when administered in a single dose or in multiple doses, to increase the amount of antibody specific to a given antigen in the individual. For example, in some cases, an effective amount of an immunomodulatory composition of the present disclosure is an amount that is effective, when administered in a single dose or in multiple doses, to increase the amount of antibody specific to a given antigen in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of antibody specific to the antigen in the individual in the absence of treatment with the immunomodulatory composition.

In some cases, an effective amount of an immunomodulatory composition of the present disclosure is an amount that is effective, when administered in a single dose or in multiple doses, to increase production of one or more cytokines in the individual. For example, in some cases, an effective amount of an immunomodulatory composition of the present disclosure is an amount that is effective, when administered in a single dose or in multiple doses, to increase production of one or more cytokines in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of the cytokine in the individual in the absence of treatment with the immunomodulatory composition. For example, in some cases, an effective amount of an immunomodulatory composition of the present disclosure is an amount that is effective, when administered in a single dose or in multiple doses, to increase production of GM-CSF in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of GM-CSF in the individual in the absence of treatment with the immunomodulatory composition. For example, in some cases, an effective amount of an immunomodulatory composition of the present disclosure is an amount that is effective, when administered in a single dose or in multiple doses, to increase production of IL-22 in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of IL-22 in the individual in the absence of treatment with the immunomodulatory composition. For example, in some cases, an effective amount of an immunomodulatory composition of the present disclosure is an amount that is effective, when administered in a single dose or in multiple doses, to increase production of interferon (IFN)-α and/or IFN-β and/or IFN-γ in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of IFN-α or IFN-β or IFN-γ in the individual in the absence of treatment with the immunomodulatory composition. As another example, in some cases, an effective amount of an immunomodulatory composition of the present disclosure is an amount that is effective, when administered in a single dose or in multiple doses, to increase production of one or more of IL-17A, IL-2, IL-10, IL-6 and TNF-α in all individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of IL-17A, IL-2, IL-10, IL-6, or TNF-α in the individual in the absence of treatment with the immunomodulatory composition.

In some cases, an effective amount of an immunomodulatory composition of the present disclosure is an amount that is effective, when administered in a single dose or in multiple doses, to increase a Th1 response in an individual. For example, in some cases, an effective amount of an immunomodulatory composition of the present disclosure is an amount that is effective, when administered in a single dose or in multiple doses, to increase a Th1 response in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the level of the Th1 response in the individual in the absence of treatment with the immunomodulatory composition.

In some cases, an effective amount of an immunomodulatory composition of the present disclosure is an amount that is effective, when administered in a single dose or in multiple doses, to increase the number and/or activity of $CD4^+$ T cells in an individual. For example, in some cases, an effective amount of an immunomodulatory composition of the present disclosure is an amount that is effective, when administered in a single dose or in multiple doses, to increase the number and/or activity of $CD4^+$ T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of $CD4^+$ T cells in the individual in the absence of treatment with the immunomodulatory composition. In some cases, an effective amount of an immunomodulatory composition of the present disclosure is an amount that is effective, when administered in a single dose or in multiple doses, to increase the number and/or activity of antigen-specific $CD4^+$ T cells in an individual. For example, in some cases, an effective amount of an immunomodulatory composition of the present disclosure is an amount that is effective, when administered in a single dose or in multiple doses, to increase the number and/or activity of antigen-specific $CD4^+$ T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of antigen-specific $CD4^+$ T cells in the individual in the absence of treatment with the immunomodulatory composition.

In some cases, an effective amount of an immunomodulatory composition of the present disclosure is an amount that is effective, when administered in a single dose or in multiple doses, to increase the number and/or activity of CD8⁺ T cells in an individual. For example, in some cases, an effective amount of an immunomodulatory composition of the present disclosure is an amount that is effective, when administered in a single dose or in multiple doses, to increase the number and/or activity of CD8⁺ T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of CD8⁺ T cells in the individual in the absence of treatment with the immunomodulatory composition. In some cases, an effective amount of an immunomodulatory composition of the present disclosure is an amount that is effective, when administered in a single dose or in multiple doses, to increase the number and/or activity of antigen-specific CD8⁺ T cells in an individual. For example, in some cases, an effective amount of an immunomodulatory composition of the present disclosure is an amount that is effective, when administered in a single dose or in multiple doses, to increase the number and/or activity of antigen-specific CD8⁺ T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of antigen-specific CD8⁺ T cells in the individual in the absence of treatment with the immunomodulatory composition.

In some cases, an effective amount of an immunomodulatory composition of the present disclosure is an amount that is effective, when administered in a single dose or in multiple doses, to increase the number and/or activity of cytolytic T cells in an individual. For example, in some cases, an effective amount of an immunomodulatory composition of the present disclosure is an amount that is effective, when administered in a single dose or in multiple doses, to increase the number and/or activity of cytolytic T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of cytolytic T cells in the individual in the absence of treatment with the immunomodulatory composition. In some cases, an effective amount of an immunomodulatory composition of the present disclosure is an amount that is effective, when administered in a single dose or in multiple doses, to increase the number and/or activity of antigen-specific cytolytic T cells in an individual. For example, in some cases, an effective amount of an immunomodulatory composition of the present disclosure is an amount that is effective, when administered in a single dose or in multiple doses, to increase the number and/or activity of antigen-specific cytolytic T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of antigen-specific cytolytic T cells in the individual in the absence of treatment with the immunomodulatory composition.

In some cases, an effective amount of an immunomodulatory composition of the present disclosure is an amount that is effective, when administered in a single dose or in multiple doses, to increase the number and/or activity of one or more of natural killer (NK) cells, NKT cells, macrophages, and dendritic cells (DCs) in an individual. For example, in some cases, an effective amount of an immunomodulatory composition of the present disclosure is an amount that is effective, when administered in a single dose or in multiple doses, to increase the number and/or activity of one or more of NK cells, NKT cells, macrophages, and DCs in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of one or more of NK cells, NKT cells, macrophages, and DCs in the individual in the absence of treatment with the immunomodulatory composition.

In some cases, an effective amount of an immunomodulatory composition of the present disclosure is an amount that is effective, when administered in a single dose or in multiple doses, to modulate the number and/or activity of Tregs in an individual. Tregs (regulatory T cells) are CD4⁺ or CD8⁺, and may also be FoxP3⁺. Tregs may also be defined by other markers such as PD-1, CTLA-4 etc. Regulatory cells may also be comprised of other innate cells such as NK, NKT and DCs, and B lymphocytes. "Modulate the number and/or activity" of Tregs, as used herein, refers to increasing, decreasing, or balancing the number and/or activity of Tregs. For example, in some cases, an effective amount of an immunomodulatory composition of the present disclosure is an amount that is effective, when administered in a single dose or in multiple doses, to decrease the number and/or activity of Tregs in an individual by at least 10%, at least 15%, at least 20%, at least 25%, at least 30%, at least 35%, at least 40%, at least 45%, at least 50%, at least 75%, or more than 75%, compared to the number and/or activity of Tregs in the individual in the absence of treatment with the immunomodulatory composition. In some cases, an effective amount of an immunomodulatory composition of the present disclosure is an amount that is effective, when administered in a single dose or in multiple doses, to increase the number and/or activity of Tregs in an individual by at least 10%, at least 25%, at least 50%, at least 2-fold, at least 5-fold, or at least 10-fold, or more than 10-fold, compared number and/or activity of Tregs in the individual in the absence of treatment with the immunomodulatory composition.

In some cases, an effective amount of an immunomodulatory composition of the present disclosure is an amount that is effective, when administered in a single dose or in multiple doses, to increase the number and/or activity of Th17 cells in an individual. For example, in some cases, an effective amount of an immunomodulatory composition of the present disclosure is an amount that is effective, when administered in a single dose or in multiple doses, to increase the number and/or activity of Th17 cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of Th17 cells in the individual in the absence of treatment with the immunomodulatory composition. In some cases, an effective amount of an immunomodulatory composition of the present disclosure is an amount that is effective, when administered in a single dose or in multiple doses, to increase the number and/or activity of antigen-specific Th17 cells in an individual. For example, in some cases, an effective amount of an immunomodulatory composition of the present disclosure is an amount that is effective, when administered in a single dose or in multiple doses, to increase the number and/or activity of antigen-specific Th17 cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of antigen-specific Th17 cells in the individual in the absence of treatment with the immunomodulatory composition.

In some cases, an effective amount of an immunomodulatory composition of the present disclosure is an amount that is effective, when administered in a single dose or in multiple doses, to increase the number and/or activity of Th22 cells in an individual. For example, in some cases, an effective amount of an immunomodulatory composition of the present disclosure is an amount that is effective, when administered in a single dose or in multiple doses, to increase the number and/or activity of Th22 cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of Th22 cells in the individual in the absence of treatment with the immunomodulatory composition. In some cases, an effective amount of an immunomodulatory composition of the present disclosure is an amount that is effective, when administered in a single dose or in multiple doses, to increase the number and/or activity of antigen-specific Th22 cells in an individual. For example, in some cases, an effective amount of an immunomodulatory composition of the present disclosure is an amount that is effective, when administered in a single dose or in multiple doses, to increase the number and/or activity of antigen-specific Th22 cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of antigen-specific Th22 cells in the individual in the absence of treatment with the immunomodulatory composition.

In some cases, an effective amount of an immunomodulatory composition of the present disclosure is an amount that is effective, when administered in a single dose or in multiple doses, to elicit, boost and/or regulate innate and/or adaptive (including both cellular and humoral) immune responses in an individual. For example, in some cases, an effective amount of an immunomodulatory composition of the present disclosure is an amount that is effective, when administered in a single dose or in multiple doses, to modulate (e.g., increase) the number and/or activity of innate and/or adaptive immune cells and/or their effector functions in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of one or more of innate or adaptive immune cells and/or their effector functions in the individual in the absence of treatment with the immunomodulatory composition.

In some cases, an effective amount of an immunomodulatory composition of the present disclosure is an amount that is effective, when administered in a single dose or in multiple doses, to protect innate and/or adaptive immune cells from depletion or prevent their apoptosis in an individual. For example, in some cases, an effective amount of an immunomodulatory composition of the present disclosure is an amount that is effective, when administered in a single dose or in multiple doses, to protect innate and/or adaptive immune cells from depletion or prevent their apoptosis in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of one or more of innate or adaptive immune cells and/or their effector functions in the individual in the absence of treatment with the immunomodulatory composition.

In some cases, an effective amount of an immunomodulatory composition of the present disclosure is an amount that is effective, when administered in a single dose or in multiple doses, to induce proliferation and/or differentiation of hematopoietic stem cells, and restore homeostasis. For example, in some cases, an effective amount of an immunomodulatory composition of the present disclosure is an amount that is effective, when administered in a single dose or in multiple doses, to induce proliferation and/or differentiation of hematopoietic stem cells, and restore homeostasis in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the individual in the absence of treatment with the immunomodulatory composition.

In some cases, an immunomodulatory composition of the present disclosure comprises HKCC and an antigen. Where an immunomodulatory composition of the present disclosure comprises HKCC and an antigen, in some cases, an effective amount of an immunomodulatory composition of the present disclosure is an amount that is effective, when administered in a single dose or in multiple doses, to increase an immune response to the antigen by at least about 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the immune response to the antigen in the absence of treatment with the immunomodulatory composition. For example, where the antigen is an antigen associated with or derived from a cancer cell, a pathogenic bacterium, a pathogenic virus, or a pathogenic protozoan, an effective amount of an immunomodulatory composition of the present disclosure is an amount that is effective, when administered in a single dose or in multiple doses, to increase an immune response to the antigen by at least about 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the immune response to the antigen in the absence of treatment with the immunomodulatory composition. The immune response can be a humoral immune response, e.g., a B cell or antibody immune response. Thus, e.g., in some cases, where the antigen is an antigen associated with or derived from a cancer cell, a pathogenic bacterium, a pathogenic virus, or a pathogenic protozoan, an effective amount of an immunomodulatory composition of the present disclosure is an amount that is effective, when administered in a single dose or in multiple doses, to increase a B cell response to the antigen by at least about 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the B cell response to the antigen in the absence of treatment with the immunomodulatory composition. For example, in some cases, where the antigen is an antigen associated with or derived from a cancer cell, a pathogenic bacterium, a pathogenic virus, or a pathogenic protozoan, an effective amount of an immunomodulatory composition of the present disclosure is an amount that is effective, when administered in a single dose or in multiple doses, to increase the amount of antibody specific to the antigen by at least about 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the amount of antibody specific to the antigen in the absence of treatment with the immunomodulatory composition. The immune response can be a cellular immune response, e.g., a T cell response. Thus, e.g., in some cases, where the antigen is an antigen associated with or derived from a cancer cell, a pathogenic bacterium, a pathogenic virus, or a pathogenic protozoan, an effective amount of an immunomodulatory composition of the present disclosure is an amount that is effective, when administered in a single dose or in multiple doses, to increase a T cell response to the antigen by at least about 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the T cell response to the antigen in the absence of treatment with the immunomodulatory composition. In some cases, the immune response is a humoral immune response and a cellular immune response.

An immunomodulatory composition of the present disclosure can comprise HKCC in an amount of from about $10^3$ HKCC per ml to about $10^{12}$ HKCC per ml. For example, an immunomodulatory composition of the present disclosure can comprise HKCC in an amount of from about $10^3$ HKCC per ml to about $10^4$ HKCC per ml, from about $10^4$ HKCC per ml to about $10^5$ HKCC per ml, from about $10^5$ HKCC per ml to about $10^6$ HKCC per ml, from about $10^6$ HKCC per nil to about $10^7$ HKCC per ml, from about $10^8$ HKCC per nil to about $10^9$ HKCC per ml, from about $10^9$ HKCC per ml to about $10^{10}$ HKCC per ml, from about $10^{10}$ HKCC per ml to about $10^{11}$ HKCC per ml, or from about $10^{11}$ HKCC per ml to about $10^{12}$ HKCC per ml.

An immunomodulatory composition of the present disclosure can comprise HKCC in an amount of from about $10^2$ to about $10^{20}$ colony forming units (cfu) per unit dosage form; for example, an immunomodulatory composition of the present disclosure can comprise HKCC in an amount of from about $10^2$ to about $10^3$ from about $10^3$ to about $10^5$, from about $10^5$ to about $10^7$, from about $10^7$ to about $10^9$, from about $10^9$ to about $10^{11}$, from about $10^{11}$ to about $10^{13}$, from about $10^{13}$ to about $10^{15}$, from about $10^{15}$ to about $10^{18}$, or from about $10^{18}$ to about $10^{20}$, cfu per unit dosage form. A unit dosage form can be an amount that is administered in a single dose; for example, a unit dosage form can be 0.5 ml, 1.0 ml, or other volume suitable for administration in a single dose.

HKCC can be generated by exposing *Caulobacter crescentus* to a temperature of from about 37° C. to about 95° C. for a time period of from about 1 minute to about 2 hours. For example, HKCC can be generated by exposing *Caulobacter crescentus* to a temperature of about 60° C. for 1 hour. As another example, HKCC can be generated by exposing *Caulobacter crescentus* to a temperature of 80° C. for about 30 minutes. HKCC are non-viable.

Alternatively, *Caulobacter crescentus* can be inactivated by chemical treatment, e.g., by treating the bacteria with glutaraldehyde or formalin. Alternatively, *Caulobacter crescentus* can be inactivated by irradiation, e.g., microwave irradiation, gamma irradiation, X rays, ultraviolet or infrared light irradiation, a photochemical process combining treatment with a synthetic psoralen and long-wave UV light, etc. Alternatively, *Caulobacter crescentus* can be inactivated by a freeze-thaw method, freeze-drying, sonication, french press sonication, lysis, cryo preservation or any other non-denaturing method. Other processes may be used for the inactivation of *Caulobacter crescentus* that are known to those of ordinary skill in the art.

Inactivation of *Caulobacter* species can be performed by treatment with acidic and/or basic conditions, various aldehydes (e.g., glutaraldehyde, formaldehyde), chemicals (e.g., beta propriolactone), solvents and varying salt concentrations. Modulating metabolic enzymes is another method of inactivating *Caulobacter*, which can be achieved by modifying culture nutrients, limiting or providing excess of various chemicals such as nucleoside tri phosphates, carbohydrates, cyclic nucleoside monophosphates (e.g., 3',5'-cyclic GMP, 8-Bromo, N2,O2'-dibutyryl cyclic GMP) etc. in the growth medium. Further, metabolic enzymes can be modulated by genetic engineering, whereby a given enzyme can be either knocked in or knocked out from *Caulobacter* sp. (J S Poindexter, The Caulobacters: Ubiquitous Unusual Bacteria, Microbiol Rev 45, 123-179, 1981).

Inactivation of *Caulobacter* for use as immunomodulatory agent described herein can also be achieved by treatment with anti-metabolite or antibiotic agents such as mitomycin C, penicillin G, cisplatin and derivatives etc., DNA cross-linking or methylating agents such as ethidium bromide, which can inhibit further replication/division of bacteria (J S Poindexter, The Caulobacters: Ubiquitous Unusual Bacteria, Microbiol Rev 45, 123-179, 1981).

Antigens

An immunomodulatory composition of the present disclosure can comprise, in addition to HKCC, one or more (e.g., 1, 2, 3, 4, 5, 6, 7, 8, 9, 10, or more than 10) antigens. Suitable antigens include, but are not limited to, an antigen derived from a pathogenic microorganism; a tumor-associated antigen; and an allergen. Antigens derived from a pathogenic microorganism include antigens derived from a virus, a bacterium, a fungus, a protozoan, or a helminth.

In some embodiments, *Caulobacter crescentus* is genetically modified to produce an antigen; and the genetically modified *Caulobacter crescentus* is heat-killed, to produce an immunomodulatory composition of the present disclosure. Methods of genetically modifying bacteria are known in the art.

In other embodiments, HKCC is admixed with an antigen in an immunomodulatory composition of the present disclosure. *Caulobacter crescentus* can act as a carrier and/or delivery vehicle to deliver antigens. As a non genetic modification (GM), such as electrostatic and hydrophobic interactions, binding of antigens to the *Caulobacter crescentus* surface may enable the *Caulobacter crescentus* to act as an antigen carrier and/or delivery vehicle. Further, due to bioadhesion/mucoadhesion, *Caulobacter crescentus* may facilitate antigen uptake by M cell transport, delivery to and subsequent activation/maturation of DCs/APCs, induction of NK, NKT, B and T cell responses at mucosal surfaces.

An antigen, for use in certain embodiments of the herein described immunomodulatory compositions and methods employing HKCC, may be any target epitope, molecule, molecular complex, cell or tissue against which elicitation or enhancement of immunogenicity in a subject is desired.

An immunomodulatory composition of the present disclosure can include one or more antigens or antigenic compositions capable of eliciting an immune response against a human or animal pathogen. The antigen can be derived from at least one infectious pathogen that is selected from a virus, a bacterium, a *mycobacterium*, a *mycoplasma*, a fungus, a tumor or a cancer cell. In certain embodiments, the antigen may be associated with autoimmune disease, allergy, asthma, prion disease or any other conditions where stimulation of an antigen-specific response would be desirable or beneficial.

A suitable antigen can be any type of antigen known in the art. Antigens can be produced in any of a variety of sources such as plants, animals, prokaryotes, in vitro cell culture, etc. Antigens can be in variety of forms as described below.

Suitable antigens include, e.g., peptides, modified peptides, peptide mimotopes, conformationally-constrained synthetic peptides, multi-epitope peptides from one or more antigens, branched peptides, lipopeptides, monolipopeptides, dilipopeptides, peptides conjugated or fused to proteins, peptides conjugated or fused to T cell or B cell epitopes. See, e.g., U.S. Pat. No. 8,198,400. Suitable antigens include, e.g., full-length antigens, truncated antigens, mutated antigens, and inactivated or combined forms from a single pathogen or different pathogen(s) or cancer. Suitable antigens include, e.g., proteins, purified or recombinant proteins, recombinant fusion proteins, proteins and peptides conjugated to toll-like receptor (TLR) agonists, proteins and peptides conjugated to bacterial toxins, proteins and peptides conjugated to antibodies, proteins and peptides conjugated to cytokines and chemokines, glycoproteins, glycolipoproteins and derivatives thereof. Suitable antigens include, e.g., polysaccharides, polysaccharide conjugates, oligosaccharides, lipids, glycolipids, carbohydrates and derivatives thereof. Suitable antigens include small molecules, e.g., morphine, nicotine and derivatives thereof. An antigen can be modified to enhance antigen presentation and/or co-stimulation, or inhibit co-inhibitory signals. A poorly immunogenic antigen can be conjugated to a carrier such as keyhole limpet hemocyanin (KLH), albumin, hepatitis B virus (HBV) core antigen, etc.

An antigen or antigenic composition can be obtained from live viruses, dead viruses, attenuated viruses, bacteria, fungi, protozoa, helminths, etc.

An antigen can be a whole cell extract, a cell lysates, a whole cell, a whole live cell, a whole inactivated cell, a whole irradiated cell, etc. An antigen can be a whole live, dead, inactivated, irradiated or attenuated pathogenic or non-pathogenic microorganism. Antigens may be crude, purified, or recombinant form. In some cases, an antigen is at least 50% pure, at least 60% pure, at least 70% pure, at least 80% pure, at least 90% pure, at least 95% pure, at least 98% pure, or at least 99% pure, or more than 99% pure.

An antigen can be chemically, enzymatically, or genetically coupled to HKCC. In some cases, an antigen is present in an immunomodulatory composition of the present disclosure in admixture with HKCC.

An immunomodulatory composition of the present disclosure can comprise a single type of antigen. An immunomodulatory composition of the present disclosure can include 2 or more different antigens. An immunomodulatory composition of the present disclosure can include 2, 3, 4, 5, 6, or more than 6, different antigens. Where an immunomodulatory composition of the present disclosure includes more than one antigen, the more than one antigen can be from the same pathogenic organism, or from the same cancer cell. Where an immunomodulatory composition of the present disclosure includes more than one antigen, the more than one antigen can be from two or more different pathogenic organisms, or from two or more different cancer cells or two or more different types of cancers.

An antigen can be in the form of a protein, a lipopolysaccharide, a lipoprotein, a proteoglycan, glycoproteins, glycosaminoglycans, an oligosaccharide, etc.

An antigen can be in the form of a nucleic acid comprising a nucleotide sequence encoding an antigen, e.g., a polypeptide antigen. For example, an antigen can be provided in the form of DNA (e.g., plasmid DNA, naked DNA etc.), RNA, and/or a wild-type, attenuated and/or recombinant vector-based nucleic acid. The nucleic acid coding for the antigen can be either "naked" or contained in a delivery system, such as liposomes.

A recombinant vector-encoded antigen can be at least one recombinant expression construct which comprises a promoter operably linked to a nucleotide sequence encoding an antigen in recombinant viral vectors (such as adenovirus (e.g. Ad2, Ad4, Ad5, Ad35, Ad35K5 etc.), adeno-associated virus, lentivirus, herpes virus, poxvirus, vesicular stomatitis virus, alpha virus, measles virus, papaya mosaic virus, cytomegalovoirus, modified vaccinia Ankara virus MVA, polio virus, Marba virus etc.), bacterial vector vaccines (such as *Salmonella, Shigella, E. coli, Lactococcus lactic, Listeria* sp., *Lactobacillus* sp.), fungal vectors (such as heat killed recombinant *Saccharomyces* yeast), plant viruses, virus-like particles (VLPs), virosomes, synthetic vaccine particles, synthetic biomimetic supramolecular biovectors, depathogenized viral/bacterial strains (such as NIBRG14 from H5N1). The vector could be in the form of live wild-type, non-replicative, mutated, modified, defective or attenuated. The vectors could be from human, animal, plant or prokaryote origin and in any effective amount.

In treating or preventing infectious disease, cancer or autoimmune diseases, antigen can be given at the same or different times, at the same or different site than the immunostimulatory composition of the present disclosure.

Antigens from Pathogenic Bacteria

In some cases, an immunomodulatory composition of the present disclosure comprises, in addition to HKCC, an antigen derived from or associated with a pathogenic bacterium. In some cases, an immunomodulatory composition of the present disclosure comprises, in addition to HKCC, one or more bacterial antigens, e.g., 1, 2, 3, 4, 5, or more bacterial antigens, from one or more bacteria.

Non-limiting examples of pathogenic bacteria include *Mycobacteria, Streptococcus, Staphylococcus, Pseudomonas, Salmonella, Neisseria*, and *Listeria*. In some cases, the bacteria is *Neisseria gonorrhea, Mycobacterium tuberculosis* (Mtb), *M. leprae, M. bovis, M. avium, M. smegmetis, M. paratuberculosis, Listeria monocytogenes, Streptococcus pneumoniae, S. pyogenes, S. agalactiae, S. viridans, S. aureus, S. epidermis, S. faecalis*, or *S. bovis*.

Other examples of bacteria contemplated include, but are not limited to, Gram positive bacteria (e.g., *Listeria, Bacillus* such as *Bacillus anthracis, Erysipelothrix* species), Gram negative bacteria (e.g., *Bartonella, Brucella, Burkholderia, Campylobacter, Enterobacter, Escherichia, Francisella, Hemophilus, Klebsiella, Morganella, Proteus, Providencia, Pseudomonas, Salmonella, Serratia, Shigella, Vibrio*, and *Yersinia* species), spirochete bacteria (e.g., *Borrelia* species including *Borrelia burgdorferi* that causes Lyme disease), anaerobic bacteria (e.g., *Actinomyces* and *Clostridium* species including *C. difficile*), Gram positive and negative coccal bacteria, *Enterococcus* species including *E. fetalis, E. faecium, Streptococcus* species, Pneumococcus species, *Staphylococcus* species, *Neisseria* species.

Additional non-limiting examples of specific infectious bacteria include *Citrobacter, Helicobacter pyloris, Borelia burgdorferi, Legionella pneumophila, Mycobacteria avium, M. intracellulare, M. kansaii, M. gordonae, M. africanum, Staphylococcus aureus, Neisseria meningitidis, Haemophilus influenzae, Bacillus anthracis, Y. pestis, Corynebacterium diphtheriae, Erysipelothrix rhusiopathiae, Clostridium perfringens, Clostridium tetani, Enterobacter aerogenes, Klebsiella pneumoniae, Pasturella multocida, Fusobacterium nucleatum, Streptobacillus moniliformis, Treponema pallidum, Treponema pertenue, Leptospira, Rickettsia, P. gingivalis* and *Actinomyces israelli*.

An antigen can be derived from any of the aforementioned bacteria.

Non-limiting examples of suitable bacterial antigens include pertussis toxin, filamentous hemagglutinin, pertactin, FIM2, FIM3, adenylate cyclase and other pertussis bacterial antigen components; diphtheria bacterial antigens such as diphtheria toxin or toxoid and other diphtheria bacterial antigen components; tetanus bacterial antigens such as tetanus toxin or toxoid and other tetanus bacterial antigen components; streptococcal bacterial antigens such as M proteins, adhesins, lipoteichoic acid, pneumonolysins and other streptococcal bacterial antigen components; gram-negative bacilli bacterial antigens such as lipopolysaccharides, toxins and other gram-negative bacterial antigen components; *Borrelia* bacterial antigens such as OspA, OspC, DbPA or DbPB; *Mycobacterium tuberculosis* bacterial antigens such as mycolic acid, heat shock protein 65 (HSP65), the 30 kDa major secreted protein, ESAT-6, antigen 85A, 85B and 85C, ID83, ID93 and other mycobacterial antigen components; *Helicobacter pylori* bacterial antigen components such as urease, catalase, vacuolating toxin; pneumococcal bacterial antigens such as pneumolysin, pneumococcal capsular polysaccharides, pneumococcal surface protein A and other pneumococcal bacterial antigen components; *haemophilus* influenza bacterial antigens such as capsular polysaccharides, adhesins, lipoproteins and other *haemophilus* influenza bacterial antigen components; anthrax bacterial antigens such as anthrax protective antigen and other anthrax bacterial antigen components; *Nisseria* spp. bacterial antigens such as capsular polysaccharides, transferrin-binding proteins, lactoferrin-binding proteins and adhesins, rickettsiae bacterial antigens such as rompA and other rickettsiae bacterial antigen component; *Chlamydia* bacterial antigens such as Momp, heparin binding proteins, ORF3 and other proteins. Also included with the bacterial antigens described herein are any other bacterial, mycobacterial, mycoplasmal, rickettsial, or chlamydial antigens.

A bacterial antigen can be purified (e.g., at least 50% pure, at least 60% pure, at least 70% pure, at least 80% pure, at least 90% pure, at least 95% pure, at least 98% pure, or at least 99% pure, or more than 99% pure). A bacterial antigen can be an extract from a bacterial cell. A bacterial antigen can be synthetically produced, e.g., by recombinant means.

Fungal Antigens

In some cases, an immunomodulatory composition of the present disclosure comprises, in addition to HKCC, one or more fungal antigens, e.g., 1, 2, 3, 4, 5, or more fungal antigens, from one or more fungi.

Fungal antigens suitable for inclusion in an immunomodulatory composition of the present disclosure include, but are not limited to, e.g., *candida* fungal antigen components; *histoplasma* fungal antigens such as heat shock protein 60 (HSP60) and other *histoplasma* fungal antigen components; cryptococcal fungal antigens such as capsular polysaccharides and other cryptococcal fungal antigen components; *Coccidioides* fungal antigens such as spherule antigens and other *Coccidioides* fungal antigen components; and tinea fungal antigens such as trichophytin and other *Coccidioides* fungal antigen components.

Fungal antigens suitable for inclusion in an immunomodulatory composition of the present disclosure can be obtained from *Candida* spp. including *C. albicans*, *Aspergillus* spp., *Cryptococcus* spp. including *C. neoformans*, *Blastomyces* sp., *Pneumocytes* spp., or *Coccidioides* spp.

Parasite Antigens

In some cases, an immunomodulatory composition of the present disclosure comprises, in addition to HKCC, a parasite antigen. Parasites include protozoan parasites and helminths. In some cases, an immunomodulatory composition of the present disclosure comprises, in addition to HKCC, one or more parasitic antigens, e.g., 1, 2, 3, 4, 5, or more parasitic antigens, from one or more parasites.

Examples of parasites include *Plasmodium* spp., *Toxoplasma gondii, Babesia* spp., *Trichinella spiralis, Entamoeba histolytica, Giardia lamblia, Enterocytozoon bieneusi, Naegleria, Acanthamoeba, Trypanosoma rhodesiense* and *Trypanosoma gambiense, Isospora* spp., *Cryptosporidium* spp, *Eimeria* spp., *Neospora* spp., *Sarcocystis* spp., and *Schistosoma* spp.

Parasite antigens can be derived from *Plasmodium* spp. (such as RTS, S, TRAP, MSP-1, MSP-3, RAP1, RAP2 etc.), *Toxoplasma* spp. including *T. gondii* (such as SAG2, SAG3, Tg34), *Entamoeba* spp. including *E. histolytica, Schistosoma* spp., *Trypanosoma cruzi Cryptosporidium* spp., *Angiostrongylus* spp., *Ancyclostoma* spp., *Wuchereria* spp., *Brugia* spp., *Giardia* spp., *Leishmania* spp., *Pneumonocystis* spp., *Enterobius* spp., *Ascaris* spp., *Trichuris* spp., *Trichomonas* spp., *Necator* spp., *Onchocerca* spp., *Dracanculus* spp., *Trichinella* spp., *Strongyloides* spp., *Opisthorchis* spp., *Paragonimus* spp., *Fasciola* spp., or *Taenia* spp.

Protozoan Antigens

In some cases, an immunomodulatory composition of the present disclosure comprises, in addition to HKCC, a protozoan antigen. A protozoan antigen can be derived from any protozoan parasite, including, but not limited to, *Giardia*; a plasmodium species (e.g., *Plasmodium falciparum*); *Toxoplasma gondii*; a *Cryptosporidium*; a *Trichomonas* species; a trypanosome (e.g., *Trypanosoma cruzi*); or *Leishmania*.

Protozoan antigens include, but are not limited to, e.g., *Plasmodium falciparum* antigens such as merozoite surface antigens, sporozoite surface antigens, circumsporozoite antigens, gametocyte/gamete surface antigens, blood-stage antigen pf 155/RESA and other plasmodial antigen components, and parasites killed by freeze-thawing etc.; toxoplasma antigens such as SAG-1, p30 and other toxoplasmal antigen components; schistosomae antigens such as glutathione-S-transferase, paramyosin, and other schistosomal antigen components; *Leishmania major* and other leishmanial antigens such as gp63, lipophosphoglycan and its associated protein and other leishmanial antigen components; and *Trypanosoma cruzi* antigens such as the 75-77 kDa antigen, the 56 kDa antigen and other trypanosomal antigen components.

Helminth Antigens

Helminth antigens that can be included in an immunomodulatory composition of the present disclosure include antigens derived from flatworms, thorny-headed worms, and roundworms (nematodes).

Viral Antigens

In some cases, an immunomodulatory composition of the present disclosure comprises, in addition to HKCC, one or more viral antigens, e.g., 1, 2, 3, 4, 5, or more viral antigens, from one or more viruses.

Viruses that can be the source of the viral antigen(s) include, but are not limited to, herpes viruses (HSV-1, HSV-2, VZV, EBV, CMV, HHV-6, HHV-8), influenza viruses (Flu A, B), hepatitis viruses (HepA, HepB, HepC, HepD, HepE), human immunodeficiency viruses (HIV-1, HIV-2), respiratory syncytial viruses, measles viruses, rhinoviruses, adenoviruses, SARS viruses, papillomaviruses, orthopoxviruses, West Nile viruses, and a dengue viruses. Viruses that can be the source of the viral antigen(s) include members of the Flaviviridae family of viruses. Viruses that can be the source of the viral antigen(s) include a flavivirus selected from the group consisting of dengue, Kunjin, Japanese encephalitits, West Nile, and yellow fever virus. Viruses that can be the source of the viral antigen(s) include lymphocytic choriomenignitis virus, hepatitis B virus, Epstein Barr virus, and human immunodeficiency virus. Viruses that can be the source of the viral antigen(s) include, but are not limited to: Retroviridae (e.g. human immunodeficiency viruses, such as HIV-1, also referred to as LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronaviridae (e.g. coronaviruses); Rhabdoviridae (e.g. vesicular stomatitis viruses, rabies viruses); Filoviridae (e.g. ebola-like viruses, Marburg viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arenaviridae (hemorrhagic fever viruses); Reoviridae (e.g. reoviruses, orbiviruses and rotaviruses); Bornaviridae; Hepadnaviridae (Hepatitis B virus); Parvoviridae (parvoviruses); Papovaviridae (papilloma viruses, polyoma viruses); Adenoviridae (e.g., adenoviruses); Herpesviridae (herpes simplex virus (HSV) 1 and 2), varicella zoster virus, cytomegalovirus (CMV), herpes virus; Poxviridae (variola viruses, vaccinia viruses, pox viruses); Bunyaviridae (e.g., Rift valley fever virus, Schmallenberg virus); and Iridoviridae (e.g. African swine fever virus); and unclassified viruses (e.g. the etiological agents of Spongiform encephalopathies, the agent of delta hepatitis, thought to be a defective satellite of hepatitis B virus), the agents of non-A, non-B hepatitis (class 1, internally transmitted; class 2, parenterally transmitted, i.e., Hepatitis C); Norwalk and related viruses, and astroviruses.

Suitable viral antigens include antigens from the herpesvirus family, including proteins derived from herpes simplex virus (HSV) types 1 and 2, such as HSV-1 and HSV-2 glycoproteins gB, gC, gD, gE, gH and ICP27; antigens derived from varicella zoster virus (VZV) such as gpI, II, IE-63, Epstein-Barr virus (EBV) such as gp350 and cytomegalovirus (CMV) including CMV gB and gH; and antigens derived from other human herpesviruses such as HHV6 and HHV7. (See, e.g. Chee et al., Cytomegaloviruses (J. K. McDougall, ed., Springer-Verlag 1990) pp. 125-169, for a review of the protein coding content of cytomegalovirus; McGeoch et al., J. Gen. Virol. (1988) 69:1531-1574, for a discussion of the various HSV-1 encoded proteins; U.S. Pat. No. 5,171,568 for a discussion of HSV-1 and HSV-2 gB and gD proteins and the genes encoding therefor; Baer et al., Nature (1984) 310:207-211, for the identification of protein coding sequences in an EBV genome; and Davison and Scott, J. Gen. Virol. (1986) 67:1759-1816, for a review of VZV.)

Suitable viral antigens include antigens from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV), can also be conveniently used in the techniques described herein. By way of example, the viral genomic sequence of HCV is known, as are methods for obtaining the sequence. See, e.g., International Publication Nos. WO 89/04669; WO 90/11089; and WO 90/14436. The HCV genome encodes several viral proteins, including E1 (also known as E) and E2 (also known as E2/NSI) and an N-terminal nucleocapsid protein (termed "core") (see, Houghton et al., Hepatology (1991) 14:381-388, for a discussion of HCV proteins, including E1 and E2). Each of these proteins, as well as antigenic fragments thereof, will find use in the present composition and methods.

Suitable viral antigens include the δ-antigen from HDV (see, e.g., U.S. Pat. No. 5,378,814). Additionally, antigens derived from HBV, such as the core antigen, the surface antigen, sAg, as well as the presurface sequences, pre-S1 and pre-S2 (formerly called pre-S), as well as combinations of the above, such as sAg/pre-S1, sAg/pre-S2, sAg/pre-S1/pre-S2, and pre-S1/pre-S2, are suitable. See, e.g., "HBV Vaccines—from the laboratory to license: a case study" in Mackett, M. and Williamson, J. D., Human Vaccines and Vaccination, pp. 159-176, for a discussion of HBV structure; and U.S. Pat. Nos. 4,722,840, 5,098,704, 5,324,513; Beames et al., J. Virol. (1995) 69:6833-6838, Birnbaum et al., J. Virol. (1990) 64:3319-3330; and Zhou et al., J. Virol. (1991) 65:5457-5464.

Suitable viral antigens include, but are not limited to, proteins from members of the families Picornaviridae (e.g., polioviruses, etc.); Caliciviridae; Togaviridae (e.g., rubella virus, dengue virus, etc.); Flaviviridae (e.g., nucleoprotein, VP35, VP40, glycoprotein, L protein); Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae (e.g., arenaviruses, tick-fever viruses); Retroviradae (e.g., HTLV-I; HTLV-II; HIV-1 (also known as HTLV-III, LAV, ARV, hTLR, etc.)), including but not limited to antigens from the isolates HIV-IIIb, HIV-SF2, HIV-LAV, HIV-LAI, HIV-MN); HIV-1-CM235, HIV-1-US4; HIV-2; simian immunodeficiency virus (SIV) among others. Additionally, antigens may also be derived from human papillomavirus (e.g., HPV6; HPV11, HPV16; HPV18) such as E1, E2, E5, E6, E7, L1, L2 proteins and the tick-borne encephalitis viruses. See, e.g. Virology, 3rd Edition (W. K. Joklik ed. 1988); Fundamental Virology, 2nd Edition (B. N. Fields and D. M. Knipe, eds. 1991), for a description of these and other viruses.

Suitable viral antigens include the gp120 or gp140 envelope proteins from any of the above HIV isolates, including members of the various genetic subtypes of HIV, are known and reported (see, e.g., Myers et al., Los Alamos Database, Los Alamos National Laboratory, Los Alamos, N. Mex. (1992); Myers et al., Human Retroviruses and Aids, 1990, Los Alamos, N. Mex.: Los Alamos National Laboratory; and Modrow et al., J. Virol. (1987) 61:570-578, for a comparison of the envelope sequences of a variety of HIV isolates) and antigens derived from any of these isolates will find use in the present methods. Suitable viral antigens include proteins derived from any of the various HIV isolates, including any of the various envelope proteins such as gp160 and gp41, gag antigens such as p24gag and p55gag, as well as proteins derived from the pol, nef, and tat regions, as well as core regions.

Suitable viral antigens include antigens of influenza virus. Specifically, the envelope glycoproteins HA and NA of influenza A can be used. Numerous HA subtypes of influenza A have been identified (Kawaoka et al., Virology (1990) 179:759-767; Webster et al., "Antigenic variation among type A influenza viruses," p. 127-168. In: P. Palese and D. W. Kingsbury (ed.), Genetics of influenza viruses. Springer-Verlag, New York). Conserved antigens of influenza such as nucleoprotein, M2 and M1 can also be used in vaccine compositions. Thus, proteins derived from any of these isolates can also be used in the compositions and methods described herein.

Suitable viral antigens include antigens of respiratory syncytial virus such as F, N, M, G proteins. Suitable viral antigens include antigens of Dengue virus such as NS1, NS3, and NS5 proteins. Thus, proteins derived from any of these isolates can also be used in the compositions and methods described herein. Suitable viral antigens for non-human mammals and other animals include, but are not limited to, antigens of porcine epidemic diarrhea (PED) virus, Foot and mouth diseases virus, classical swine fever virus, rabies virus, Pseudorabies virus, infectious bovine rhinotracheitis (IBR) virus, avian influenza, West Nile virus, chicken infectious anemia virus, bovine viral diarrhea virus (BVDV), equine herpes viruses, simian immunodeficiency virus, feline leukemia virus, feline sarcoma virus etc.

Cancer-Associated Antigens

In some cases, an immunomodulatory composition of the present disclosure comprises, in addition to HKCC, a cancer-associated antigen. Cancer-associated antigens can be derived from the cell surface, cytoplasm, nucleus, organelles and the like of cells of tumor tissue. Cancer associated antigens can also be associated with tumor-support mechanisms e.g., angiogenesis and tumor invasion. Tumor associated antigens (TAAs) may be autologous tumor cells (e.g., irradiated, sonicated, lysed, etc.). In some cases, an immunomodulatory composition of the present disclosure comprises, in addition to HKCC, one or more cancer antigens, e.g., 1, 2, 3, 4, 5, or more cancer antigens, from one or more cancers.

Examples of cancer-associated antigens include, without limitation, antigens associated with hematological cancers such as leukemias and lymphomas, neurological tumors such as astrocytomas or glioblastomas, melanoma, breast cancer, lung cancer, head and neck cancer, gastrointestinal tumors such as gastric or colon cancer, liver cancer, pancreatic cancer, genitourinary tumors such cervix, uterus, ovarian cancer, vaginal cancer, testicular cancer, prostate cancer or penile cancer, bone tumors, vascular tumors, or cancers of the lip, nasopharynx, pharynx and oral cavity, esophagus, rectum, gall bladder, biliary tree, larynx, lung and bronchus, bladder, kidney, brain and other parts of the nervous system, thyroid, Hodgkin's disease, non-Hodgkin's lymphoma, multiple myeloma and leukemia.

Cancer-associated antigens include, e.g., mutated oncogenes; viral proteins associated with tumors; and tumor mucins and glycolipids. The antigens may be viral proteins associated with tumors. Certain antigens may be characteristic of tumors (one subset being proteins not usually expressed by a tumor precursor cell), or may be a protein which is normally expressed in a tumor precursor cell, but having a mutation characteristic of a tumor. Other antigens include mutant variant(s) of the normal protein having an altered activity or subcellular distribution, e.g., mutations of genes giving rise to tumor antigens.

Specific non-limiting examples of suitable tumor antigens include: CEA, prostate specific antigen (PSA), HER-2/neu, BAGE, GAGE, MAGE 1-4, 6 and 12, MUC (Mucin) (e.g., MUC-1, MUC-2, etc.), GM2 and GD2 gangliosides, ras, myc, tyrosinase, MART (melanoma antigen), Pmel 17 (gp100), GnT-V intron V sequence (N-acetylglucoaminyl-transferase V intron V sequence), Prostate Ca psm, PRAME (melanoma antigen), β-catenin, MUM-1-B (melanoma ubiquitous mutated gene product), GAGE (melanoma antigen) 1, BAGE (melanoma antigen) 2-10, c-ERB2 (Her2/neu), EBNA (Epstein-Barr Virus nuclear antigen) 1-6, gp75, human papilloma virus (HPV) E6 and E7, p53, lung resistance protein (LRP), Bcl-2, and Ki-67.

Suitable cancer-associated antigens include, e.g., Melan-A/MART-1, Dipeptidyl peptidase IV (DPPIV), adenosine deaminase-binding protein (ADAbp), cyclophilin b, Colorectal associated antigen (CRC)-C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100.sup.Pme1117, PRAME, NY-ESO-1, brain glycogen phosphorylase, SSX-1, SSX-2 (HOM-MEL-40), SSX-1, SSX-4, SSX-5, SCP-1, CT-7, cdc27, adenomatous polyposis coli protein (APC), fodrin, P1A, Connexin 37, Ig-idiotype, p15, gp75, GM2 and GD2 gangliosides, viral products such as human papilloma virus proteins, Smad family of tumor antigens, 1mp-1, EBV-encoded nuclear antigen (EBNA)-1, or c-erbB-2.

Autoantigens

In some cases, an immunomodulatory composition of the present disclosure comprises, in addition to HKCC, an autoantigen. In some cases, an immunomodulatory composition of the present disclosure comprises, in addition to HKCC, one or more autoantigens, e.g., 1, 2, 3, 4, 5, or more antigens, from one or more self tissues.

For example, where the autoimmune disease is type 1 diabetes, an antigen can be pancreatic islet beta cell associated antigen, HSP60; for systemic lupus erythematosus, an antigen can be snRNP; for Grave's disease, an antigen can be thyroglobulin, thyrotropin receptor or a thyroid epithelial cell; for thrombocytopenic purpura, an antigen can be a platelet, GPIIB/IIIa; for multiple sclerosis, an antigen can be myelin basic protein, MOG, PLP; for celiac disease, an antigen can be transglutaminidase.

A suitable autoantigen can be an autoantigen involved in the initiation and/or propagation of an autoimmune disease, the pathology of which can be due to the presence of antibodies specific for a molecule expressed by the relevant target organ, tissue, or cells, e.g., systemic lupus erythematosus (SLE) or myasthenia gravis (MG). In such diseases, it can be desirable to direct an ongoing antibody-mediated (i.e., a Th2-type) immune response to the relevant autoantigen towards a cellular (i.e., a Th1-type) immune response. Alternatively, it can be desirable to prevent onset of or decrease the level of a Th2 response to the autoantigen in a subject not having, but who is suspected of being susceptible to, the relevant autoimmune disease by prophylactically inducing a Th1 response to the appropriate autoantigen. Autoantigens that can be included in a subject immunomodulatory composition include, without limitation: (a) with respect to SLE, the Smith protein, RNP ribonucleoprotein, and the SS-A and SS-B proteins; and (b) with respect to MG, the acetylcholine receptor. Examples of other antigens involved in one or more types of autoimmune response include, e.g., endogenous hormones such as luteinizing hormone, follicular stimulating hormone, testosterone, growth hormone, prolactin, and other hormones.

Other examples of suitable autoantigens include antigens associated with neurological diseases such as schizophrenia, Alzheimer's disease, depression, hypopituitarism, and cardiovascular diseases such as atherosclerosis (e.g., an antigen for atherosclerosis can be cholesteryl ester transfer protein, oxidized LDL, apoB210, apoB100) etc.

Allergens

In some cases, an immunomodulatory composition of the present disclosure comprises, in addition to HKCC, an allergen. Suitable allergens can be obtained and/or produced using known methods. Classes of suitable allergens include, but are not limited to, pollens, animal dander other than cat dander, grasses, molds, dusts, antibiotics, stinging insect venoms, and a variety of environmental (including chemicals and metals), drug and food allergens. Common tree allergens include pollens from cottonwood, popular, ash, birch, maple, oak, elm, hickory, and pecan trees; common plant allergens include those from mugwort, ragweed, English plantain, sorrel-dock and pigweed; plant contact allergens include those from poison oak, poison ivy and nettles; common grass allergens include rye grass, Timothy, Johnson, Bermuda, fescue and bluegrass allergens; common allergens can also be obtained from molds or fungi such as *Alternaria, Fusarium, Hormodendrum, Aspergillus, Micropolyspora, Mucor* and thermophilic actinomycetes; epidermal allergens can be obtained from house or organic dusts (typically fungal in origin), from arthropods such as house mites (*Dermatophagoides pteronyssinus*), or from animal sources such as feathers, and dog dander; common food allergens include milk and cheese (diary), egg, wheat, nut (e.g., peanut), seafood (e.g., shellfish), pea, bean and gluten allergens; common environmental allergens include metals (nickel and gold), chemicals (formaldehyde, trinitrophenol and turpentine), Latex, rubber, fiber (cotton or wool), burlap, hair dye, cosmetic, detergent and perfume allergens; common drug allergens include local anesthetic and salicylate allergens; antibiotic allergens include penicillin, tetracycline and sulfonamide allergens; and common insect allergens include bee, wasp and ant venom, and cockroach calyx allergens. Particularly well characterized allergens include, but are not limited to, the major and cryptic epitopes of the Der p I allergen (Hoyne et al. (1994) Immunology 83190-195), bee venom phospholipase A2 (PLA) (Akdis et al. (1996) J. Clin. Invest. 98:1676-1683), birch pollen allergen Bet v 1 (Bauer et al. (1997) Clin. Exp. Immunol. 107:536-541), and the multi-epitopic recombinant grass allergen rKBG8.3 (Cao et al. (1997) Immunology 90:46-51). These and other suitable allergens are commercially available and/or can be readily prepared as extracts following known techniques.

Suitable allergens include tree pollen allergens, weed pollen allergens, herb pollen allergens, grass pollen allergens, mile allergens, insect allergens, venom allergens, animal hair allergens, dander allergens and food allergens.

In some cases, the allergen is in the form of an extract, a purified allergen, a modified allergen or a recombinant allergen or a mutant of a recombinant allergen or any combination thereof. In some cases, the allergen is selected from the group consisting of grass pollen allergen, dust mite allergen, ragweed allergen, cat allergen and birch allergen.

An allergen can be present in an immunomodulatory composition of the present disclosure in an amount of from about 2.5 µg to about 75 µg per unit dosage form. For example, an allergen can be present in an immunomodulatory composition of the present disclosure in an amount of from about 2.5 µg to about 5 µg, from about 5 µg to about 10 µg, from about 10 µg to about 15 µg, from about 15 µg to about 20 µg, from about 20 µg to about 25 µg, from about 25 µg to about 50 µg, or from about 50 µg to about 75 µg, or more than 75 µg, per unit dosage form.

In some cases, a dose of an immunomodulatory composition of the present disclosure that comprises an allergen has a potency of about 65 to about 17,600 Biological Allergen Units (BAU). In some cases, a dose of an immunomodulatory composition of the present disclosure that comprises an allergen comprises from about 650 BAU to about 6,000 BAU.

Antibodies

In some cases, an immunomodulatory composition of the present disclosure comprises, in addition to HKCC, an antibody against a cancer antigen or a pathogenic antigen (e.g., a therapeutic antibody, monoclonal antibodies, bispecific antibodies, chemoimmuno conjugated antibodies, radioimmunoconjugated antibodies, antibody-cytokine fusion proteins, antibody-antigen fusion proteins, antibody-immunotoxin fusion protein etc.).

Antibodies that can be included in an immunomodulatory composition of the present disclosure include, without limitation, antibodies directed against co-stimulatory or co-inhibitory molecules (CD28, CD40, CTLA-4, PD-1 etc.); and other therapeutic antibodies.

Non-limiting examples of suitable antibodies include, but are not limited to, adalimumab, bevacizumab, infliximab, abciximab, alemtuzumab, bapineuzumab, basiliximab, belimumab, briakinumab, brodalumab, canakinumab, certolizumab pegol, cetuximab, conatumumab, denosumab, eculizumab, etrolizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumornab, pertuzumab, ranibizumab, rituximab, rovelizumab, tocilizumab, tositumomab, trastuzumab, ustekinumab, vedolizomab, zalutumumab, and zanolimumab.

Non-limiting examples of therapeutic and prophylactic antibodies that can be used in combination with an immunomodulatory composition of the present disclosure include MDX-010 (Medarex, N.J.) which is a humanized anti-CTLA-4 antibody for the treatment of prostate cancer; SYNAGIS™ (MedImmune, Md.) which is a humanized anti-respiratory syncytial virus (RSV) monoclonal antibody for the treatment of RSV infection; and HERCEPTIN™ (Trastuzumab) (Genentech, Calif.) which is a humanized anti-HER2 monoclonal antibody for the treatment of metastatic breast cancer. Other examples are humanized anti-CD18 F(ab')$_2$ (Genentech); CDP860 which is a humanized anti-CD18 F(ab')$_2$ (Celltech, UK); PRO542 which is an anti-HIV gp120 antibody fused with CD4 (Progenics/Genzyme Transgenics); Ostavir which is a human anti-Hepatitis B virus antibody (Protein Design Lab/Novartis); PROTOVIR™ which is a humanized anti-CMV IgGI antibody (Protein Design Lab/Novartis); MAK-195 (SEGARD) which is a murine anti-TNF-α F(ab')$_2$ (Knoll Pharma/BASF); IC14 which is an anti-CD14 antibody (ICOS Pharm); a humanized anti-VEGF IgG1 antibody (Genentech); OVAREX™ which is a murine anti-CA 125 antibody (Altarex); PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti-CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); Smart ID10 which is a humanized anti-HLA antibody (Protein Design Lab); ONCOLYM™ (Lym-1) is a radiolabelled murine anti-HLA DIAGNOSTIC REAGENT antibody (Techniclone); ABX-IL8 is a human anti-IL8 antibody (Abgenix); anti-CD11a is a humanized IgG1 antibody (Genentech/Xoma); ICM3 is a humanized anti-ICAM3 antibody (ICOS Pharm); IDEC-114 is a primatized anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); MDX-33 is a human anti-CD64 (FcγR) antibody (Medarex/Centeon); SCH55700 is a humanized anti-IL-5 IgG4 antibody (Celltech/Schering); SB-240563 and SB-240683 are humanized anti-IL-5 and IL-4 antibodies, respectively, (SmithKline Beecham); rhuMab-E25 is a humanized anti-IgE IgG1 antibody (Genentech/Norvartis/Tanox Biosystems); ABX-CBL is a murine anti CD-147 IgM antibody (Abgenix); BTI-322 is a rat anti-CD2 IgG antibody (MedImmune/Bio Transplant); Orthoclone/OKT3 is a murine anti-CD3 IgG2a antibody (ortho Biotech); SIMULECT™ is a chimeric anti-CD25 IgG1 antibody (Novartis Pharm); LDP-01 is a humanized anti-β$_2$-integrin IgG antibody (LeukoSite); Anti-LFA-1 is a murine anti CD18 F(ab').sub.2 (Pasteur-Merieux/Immunotech); CAT-152 is a human anti-TGF-β$_2$ antibody (Cambridge Ab Tech); and Corsevin M is a chimeric anti-Factor VII antibody (Centocor). The above-listed immunoreactive reagents, as well as any other immunoreactive reagents, may be administered according to any regimen known to those of skill in the art, including the regimens recommended by the suppliers of the immunoreactive reagents.

Cytokines

In some cases, an immunomodulatory composition of the present disclosure comprises, in addition to HKCC, a cytokine. Cytokines that can be included in an immunomodulatory composition of the present disclosure include, without limitation, interleukins, transforming growth factors (TGFs), fibroblast growth factors (FGFs), platelet derived growth factors (PDGFs), epidermal growth factors (EGFs), colony stimulating factors (CSFs), connective tissue activated peptides (CTAPs), osteogenic factors, and biologically active analogs, fragments, and derivatives of such growth factors. Suitable cytokines include B/T-cell differentiation factors, B/T-cell growth factors, mitogenic cytokines, chemotactic cytokines, colony stimulating factors, angiogenesis factors, IFN-α, IFN-β, IFN-γ, IL1, IL2, IL3, IL4, IL5, IL6, IL7, IL8, IL9, IL10, IL11, IL12, IL13, IL14, IL15, IL16, IL17, IL18, IL22, etc., leptin, myostatin, macrophage stimulating protein, platelet-derived growth factor, tumor necrosis factor (TNF)-alpha (TNF-α), TNF-β, nerve growth factor (NGF), CD40L, CD137L/4-1BBL, human lymphotoxin-β, G-CSF, M-CSF, GM-CSF, platelet-derived growth factor (PDGF), IL-1α, IL-1β, IP-10, PF4, GRO, 9E3, erythropoietin, endostatin, angiostatin, vascular endothelial growth factor (VEGF) or any fragments or combinations thereof. Other cytokines include members of the transforming growth factor (TGF) supergene family include the beta transforming growth factors (for example TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); hematopoietic growth factors (Flt3); pituitary growth hormones or derivatives; growth hormones, neuroactive hormones, Inhibins (for example, Inhibin A, Inhibin B); differentiation factors (for example, GDF-1); and Activins (for example, Activin A, Activin B, Activin AB). In some cases, an immunomodulatory composition of the present disclosure comprises, in addition to HKCC, a compound or agent modulating cytokines.

Caulobacter crescentus

An immunomodulatory composition of the present disclosure comprises inactivated *Caulobacter*, where the *Caulobacter* is non-pathogenic. The non-pathogenic *Caulobacter* genus includes 19 different species, including two species of Asliccacaulis (*C. vibroides, C. henricii, C. intermedius, C. robiginosus, C. rutilis, C. subvibriodes, C. fusiformis, C. rossii, A. excentricus, A. biprosthecum* etc.). See, e.g., JS Poindexter, The Caulobacters: Ubiquitous Unusual Bacteria, Microbiol Rev 45, 123-179, 1981). Several of the *Caulobacter* sp. are available from the American Type Culture Collection (ATCC), such as CB35, CB26, CB28, KA5, CB66, FC4 etc. All of these species of *Caulobacter* in heat-killed, inactivated, mutated or attenuated forms can be used as immunomodulatory agents described herein. In addition, *Caulobacter* bacteria can be in non-motile prosthecate, motile swarmer, stubby flagellin and flagellin positive, flagellin negative, dividing and/or non-dividing forms. *Caulobacter* sp. can be grown at temperatures ranging from 18°-42° C., and pH ranging from 5-9, but optimally at a temperature in a range of 23-25° C. and pH 7.

Mutated or genetically modified forms of *Caulobacter* sp. can be produced by modifying the nutrients, chemicals, pH, temperature, ultraviolet or infrared light, radiation etc. of the culture conditions, or genetically modifying various enzymes, metabolic pathways, surface molecules, nucleic acids, plasmids, cellular and cell wall components, smooth and rough LPS in live bacteria (JS Poindexter, The Caulobacters: Ubiquitous Unusual Bacteria, Microbiol Rev 45, 123-179, 1981).

*Caulobacter crescentus* can act as a carrier and/or delivery vehicle to deliver antigens. As a non genetic modification (GM), such as electrostatic and hydrophobic interactions, binding of antigens to the *Caulobacter crescentus* surface may enable the *Caulobacter crescentus* to act as an antigen carrier and/or delivery vehicle. Further, due to bioadhesion/mucoadhesion, *Caulobacter crescentus* may facilitate antigen uptake by M cell transport, delivery to and subsequent activation/maturation of DCs/APCs, induction of NK, NKT, B and T cell responses at mucosal surfaces.

Although the discussion below focuses on *Caulobacter crescentus*, any of a variety of non-pathogenic *Caulobacter* species can be included in an immunomodulatory composition of the present disclosure.

In some cases, an immunomodulatory composition of the present disclosure comprises heat-killed *Caulobacter crescentus* (HKCC). In some cases, the *Caulobacter crescentus* is wild-type. In some cases, the *Caulobacter crescentus* is a lipopolysaccharide-negative strain. In some cases, the *Caulobacter crescentus* is an S-layer-negative strain. In some cases, the HKCC is mutated attenuated, or contains suicidal mutations. In some cases CC is chemically or physically inactivated. In some cases, *Caulobacter crescentus* is with or without a drug resistant plasmid such as chloramphenicol, penicillin resistant plasmids.

In some cases, the *Caulobacter crescentus* is genetically modified to produce one or more heterologous polypeptides. The polypeptides can be of a wide range of sizes. Suitable heterologous polypeptides include, but are not limited to, CD40, a costimulatory protein found on antigen-presenting cells or T cells; DEC205 (see, e.g. Lahoud et al. (2012) *Proc. Natl. Acad. Sci. USA* 109:16270); CD40L; a co-inhibitory protein found on antigen-presenting cells (APCs) or T cells; a cytokine (e.g., GM-CSF; or any of the above-listed cytokines); a chemokine; an antigen (e.g., a viral antigen; a bacterial antigen; a tumor-associated antigen; a helminth antigen; a protozoan antigen; an autoantigen as described herein above); an antibody against an antigen (e.g., a viral antigen; a bacterial antigen; a tumor-associated antigen; a helminth antigen; a protozoan antigen; as described herein above), a signalling molecule, a receptor, a cytokine; a fusion protein (e.g., an antigen and a cytokine, an antigen and a carrier protein) etc. In some cases, *Caulobacter crescentus* is genetically modified to express anticancer (e.g., kinesin spindle protein), antiviral (e.g., entry and fusion inhibitors), antibacterial, antifungal and/or antimicrobial peptides on the surface, in secreted form or intracellularly.

In some cases, *Caulobacter crescentus* is modified by labeling or coupling the bacterium with fluorescent, radioactive isotope, light tags etc.

In some cases, *Caulobacter crescentus* is genetically modified to provide desired immune responses. In some cases, *Caulobacter crescentus* is genetically modified so that microbe is attenuated. In some cases, the nucleic acid of the *Caulobacter crescentus* is modified so that microbe is attenuated for proliferation.

In some cases, an immunomodulatory composition of the present disclosure comprises whole HKCC. In some cases, an immunomodulatory composition of the present disclosure comprises individual or multiple components of HKCC which can be isolated, synthesized, or genetically manufactured. Fractions of inactivated *Caulobacter crescentus* can be obtained by treatment with various organic solvents, enzymes such as glycosidases, lipase, DNAse, RNAse, protease, lysozyme etc.

In some cases, *Caulobacter crescentus* is bioengineered in its outer membrane vesicle to package and deliver chemotherapeutics and/or immunotherapeutics.

Adjuvants

An immunomodulatory composition of the present disclosure can comprise, in addition to HKCC, one or more additional adjuvants.

Exemplary additional adjuvants include, but are not limited to: (1) oil-in-water emulsion formulations (with or without other specific immunostimulating agents such as muramyl peptides (see below) or bacterial cell wall components), such as for example (a) MF59™ (WO 90/14837; Chapter 10 in Vaccine design: the subunit and adjuvant approach, eds. Powell & Newman, Plenum Press 1995), containing 5% Squalene, 0.5% Tween 80, and 0.5% Span 85 (optionally containing MTP-PE) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), e.g., MPL+CWS (Detox™); (2) saponin adjuvants, such as QS21 or Stimulon™ (Cambridge Bioscience, Worcester, Mass.) may be used or particles generated therefrom such as ISCOMs (immunostimulating complexes), which ISCOMS may be devoid of additional detergent e.g. WO 00/07621;

(3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12, IL-15, IL-28, etc.) (WO99/44636), etc.), interferons (e.g. gamma interferon), macrophage colony stimulating factor (M-CSF), tumor necrosis factor (TNF), colony-stimulating factors (e.g., GM-CSF), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO 00/56358; (6) combinations of 3dMPL with, for example, QS21 and/or oil-in-water emulsions e.g. EP-A-0835318, EP-A-0735898, EP-A-0761231; (7) oligonucleotides comprising CpG motifs (Krieg Vaccine 2000, 19, 618-622; WO 96/02555, WO 98/16247, WO 98/18810, WO 98/40100, WO 98/55495, WO 98/37919 and WO 98/52581), i.e., oligonucleotides containing at least one CG dinucleotide, where the cytosine is unmethylated; (8) a polyoxyethylene ether or a polyoxyethylene ester e.g. WO 99/52549; (9) a polyoxyethylene sorbitan ester surfactant in combination with an octoxynol (WO 01/21207) or a polyoxyethylene alkyl ether or ester surfactant in combination with at least one additional non-ionic surfactant such as an octoxynol (WO 01/21152); (10) a saponin and an immunostimulatory oligonucleotide (e.g. a CpG oligonucleotide) (WO 00/62800); (11) an immunostimulant and a particle of metal salt e.g. WO 00/23105; (12) a saponin and an oil-in-water emulsion e.g. WO 99/11241; (13) a saponin (e.g. QS21)+3dMPL+IM2 (optionally including a sterol) e.g. WO 98/57659; (14) alphaGalCer and its derivatives; (16) toll-like receptor (TLR) agonists, NOD-like receptor (NLR) agonists, RIG-I agonists, agonists for C-type lectin receptors and other pathogen recognition receptor (PRR) agonists e.g., CpG ODNs, ISS-ODNs, rinatolimod, polyI:C and its derivatives, flagellin, ampligen, imidazoquinalines (e.g., imiquimod, resiquimod), muramyl dipeptides; (17) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc. Adjuvants suitable for administration to a human included in some cases.

Further exemplary additional adjuvants include, but are not limited to: cholera toxin B subunit, BCG, *Pseudomonas aeruginosa* exoprotein A, tocopherol, HBV core, *E. coli* heat labile toxins (such as LT-A, LT-B), Pertussis toxin, Diphtheria toxoid, tetanus toxoid, Cholera toxin derived (CTA1-DD, CT), mutant LT and CT, Aluminium salt-based adjuvants (such as Alum, Aluminum phosphate, Aluminum sulphate, Alhydrogel), Calcium phosphate, kaolin, monophosphoryl lipid Λ (MPL$^R$) and its derivatives, glucoppyranosyl lipid Λ, synthetic lipid Λ, Lipid A mimetics, Vitamin E, Depovax™, Saponins (Quil-A, AS01, AS02 (squalene+MPL+QS-21)), AS03, AS04 (alum+MPL$^R$), Tomatin, Protolin, RC-529, Pluronic™, Monatides, Matrix-M, OM-174, Lipovac, IC-31, bacterial/mycobacterial peptides (such as KLK, cationic (poly)peptides, anti-bacterial microbial peptides, defensins, tuftsin, cathelicidin), dipeptides (such as pidotimod), Bestatin, Hepon (tetradecapeptide), SCV-07 (gamma-D-glutamyl-L-tryptophan), Thymosin-a, Immunofan, Thymogen, Indolicidin and its derivatives, polyphosphagene and its derivatives, Gellan, nucleotides (mononucleotides, dinucleotides, polynucleotides, cyclic nucleotides), Eurocine etc.

An immunomodulatory composition of the present disclosure can comprise, in addition to HKCC, one or more mucoadhesives such as sodium alginate, starch, lectins, thiolated polymers, GelVac™, sodium carboxymethylcellulose, hydroxylpropyl methylcellulose, carbomers, cetyl trimethyl ammonium bromide.

An immunomodulatory composition of the present disclosure can comprise, in addition to HKCC, one or more additional adjuvant formulations such as oil-in-water emulsions, water-in-oil emulsions, nanoemulsions, particulate delivery systems, liposomes, microspheres, biodegradable microspheres, patches virosomes, proteoliposomes, proteasomes, Immunostimulatory complexes (ISCOMs, ISCO-MATRIX), microparticles, nanoparticles, biodegradable nanoparticles, silicon nanoparticles, polymeric micro/nano particles, polymeric lamellar substrate particles (PLSP), microparticle resins, nanolipogels, synthetic/biodegradable and biocompatible semisynthetic or natural polymers or dendrimers (such as PLG, PLGA, PLA, polycaprolactone, silicone polymer, polyesters, poly-dimethyl siloxane, sodium polystyrene sulphonate, polystyrene benzyl trimethyl ammonium chloride, polystyrene divinyl benzene resin, polyphosphazene, poly-[di-(carboxylactophenoxy) phosphazene] (PCPP), poly-(methylmethacrylate), dextran, polyvinylpyrrolidone, hyaluronic acid and derivatives, chitosan and its derivatives, polysaccharides, Delta inulin polysaccharide, glycolipids (synthetic or natural), lipopolysaccharides, polycationic compound(s) (such as Poly-amino acids, poly-(γ-glutamic acid), poly-arginine-HCl, poly-L-lysine, polypeptides, biopolymers), cationic dimethyldioctadecyl ammonium (DDA), alpha-galactosyl ceramide and its derivatives, archaeal lipids and derivatives, lactanes, gallen, glycerolipids, phospholipids, cochleates, etc. or mixtures thereof.

An immunomodulatory composition of the present disclosure can comprise, in addition to HKCC, one or more additional adjuvant formulations such as oil-in-water emulsions or water-in-oil emulsions including edible oils (such as olive oil, mustard oil, vegetable oil, soybean oil, mineral oil etc.).

An immunomodulatory composition of the present disclosure can comprise, in addition to HKCC, one or more additional surfactants and detergents (e.g., non-ionic detergents or niosomes) (such as Tween-80, Polysorbate 80, Span 85, Stearyl tyrosine etc.). An immunomodulatory composition of the present disclosure can comprise, in addition to HKCC, an additional component or adjuvant mentioned above which provides a depot effect.

Methods

The present disclosure provides methods of modulating an immune response in an individual, the method comprising administering to the individual an effective amount of an immunomodulatory composition of the present disclosure.

The present disclosure also provides a method of enhancing antigen presentation on a dendritic cell, the method comprising: a) contacting dendritic cells (DCs) obtained from an individual with a composition comprising: i) heat-killed *Caulobacter crescentus*; and ii) an antigen; the contacting step is in vitro, and enhances antigen presentation of the antigen on the DCs, thereby generating a population of antigen-presenting DCs. The population of antigen-presenting DCs can then be administered to the individual from whom the DCs were obtained.

In some cases, various immune cells can be obtained from lymphoid tissues, peripheral blood, organs and tissues, and/or can be differentiated from stem cells obtained from bone marrow or various organs.

The present disclosure also provides a method of inducing proliferation and/or differentiation of stem cells, the method comprising contacting stem cells obtained from an individual with a composition comprising heat-killed *Caulobacter crescentus*. Contacting the stem cells with the HKCC leads to proliferation and differentiation of the stem cells, thereby generating a population of expanded and differentiated cells. The population of expanded and differentiated cells can then be administered to the individual from whom the stem cells were obtained.

The present disclosure further provides a method of activating effector lymphocytes such as NK, NKT, T cells, and B cells, the method comprising: a) contacting effector cells (NK, NKT, T cells, B cells) obtained from an individual with a composition comprising: i) heat-killed *Caulobacter crescentus*; and/or ii) an antigen in the presence or absence of antigen presenting cells. Contacting the effector lymphocytes with the HKCC enhances activation of the effector lymphocytes, thereby generating a population of activated effector lymphocytes. The population of activated effector lymphocytes can then be administered to the individual from whom the lymphocytes were obtained.

Methods of Modulating an Immune Response

The present disclosure provides methods of modulating an immune response in an individual, the method comprising administering to the individual an effective amount of an immunomodulatory composition of the present disclosure.

In some cases, the immune response is a humoral immune response. In some cases, the present disclosure provides methods of enhancing a humoral immune response in an individual, the method comprising administering to the individual an effective amount of an immunomodulatory composition of the present disclosure. In some cases, the immunomodulatory composition does not include any additional antigens (other than antigens present on HKCC). In some cases, the immunomodulatory composition comprises an antigen (e.g., an antigen other than antigens present on HKCC). As described above, suitable antigens include bacterial antigens, viral antigens, tumor-associated antigens, protozoan antigens, and helminth antigens.

In some cases, the immune response is a cellular immune response. In some cases, the present disclosure provides methods of enhancing a cellular immune response in an individual, the method comprising administering to the individual an effective amount of an immunomodulatory composition of the present disclosure. In some cases, the immunomodulatory composition does not include any additional antigens (other than antigens present on HKCC). In some cases, the immunomodulatory composition comprises an antigen (e.g., an antigen other than antigens present on HKCC). As described above, suitable antigens include bacterial antigens, viral antigens, tumor-associated antigens, protozoan antigens, and helminth antigens.

In some cases, the immune response comprises an increase in the number of B cells. In some cases, a subject method comprising administering to an individual in need thereof an effective amount of an immunomodulatory composition, where an effective amount of an immunomodulatory composition is an amount that, when administered to the individual in a single dose or in multiple doses, is effective to increase the number of B cells in an individual. For example, in some cases, an effective amount of an immunomodulatory composition of the present disclosure is an amount that is effective, when administered in a single dose or in multiple doses, to increase the number of B cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the number of B cells in the individual in the absence of treatment with the immunomodulatory composition. In some cases, an effective amount of an immunomodulatory composition of the present disclosure is an amount that is effective, when administered in a single dose or in multiple doses, to increase the number of antigen-specific B cells in an individual. For example, in some cases, an effective amount of an immunomodulatory composition of the present disclosure is an amount that is effective, when administered in a single dose or in multiple doses, to increase the number of antigen-specific B cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the number of antigen-specific B cells in the individual in the absence of treatment with the immunomodulatory composition.

In some cases, an effective amount of an immunomodulatory composition of the present disclosure is an amount that is effective, when administered in a single dose or in multiple doses, to increase activation of B cells in an individual. For example, in some cases, an effective amount of an immunomodulatory composition of the present disclosure is an amount that is effective, when administered in a single dose or in multiple doses, to increase activation of B cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, at least 25-fold, at least 50-fold, at least 100-fold, or more than 100-fold, compared to the activation level of B cells in the individual in the absence of treatment with the immunomodulatory composition.

In some cases, an effective amount of an immunomodulatory composition of the present disclosure is an amount that is effective, when administered in a single dose or in multiple doses, to increase the amount of antibody specific to a given antigen in the individual. For example, in some cases, an effective amount of an immunomodulatory composition of the present disclosure is an amount that is effective, when administered in a single dose or in multiple doses, to increase the amount of antibody specific to a given antigen in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of antibody specific to the antigen in the individual in the absence of treatment with the immunomodulatory composition.

In some cases, an effective amount of an immunomodulatory composition of the present disclosure is an amount that is effective, when administered in a single dose or in multiple doses, to increase production of one or more cytokines in the individual. For example, in some cases, an effective amount of an immunomodulatory composition of the present disclosure is an amount that is effective, when administered in a single dose or in multiple doses, to increase production of one or more cytokines in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of the cytokine in the individual in the absence of treatment with the immunomodulatory composition. For example, in some cases, an effective amount of an immunomodulatory composition of the present disclosure is an amount that is effective, when administered in a single dose or in multiple doses, to increase production of GM-CSF in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of GM-CSF in the individual in the absence of treatment with the immunomodulatory composition. For example, in some cases, an effective amount of an immunomodulatory composition of the present disclosure is an amount that is effective, when administered in a single dose or in multiple doses, to increase production of IL-22 in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of IL-22 in the individual in the absence of treatment with the immunomodulatory composition. For example, in some cases, an effective amount of an immunomodulatory composition of the present disclosure is an amount that is effective, when administered in a single dose or in multiple doses, to increase production of interferon (IFN)-α and/or IFN-β and/or IFN-γ in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of IFN-α or IFN-β or IFN-γ in the individual in the absence of treatment with the immunomodulatory composition. For example, in some cases, an effective amount of an immunomodulatory composition of the present disclosure is an amount that is effective, when administered in a single dose or in multiple doses, to increase production of one or more of IL-17A, IL-2, IL-10, IL-6 and/or TNF-α in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of IL-17A, IL-2, IL-10, IL-6, or TNF-α in the individual in the absence of treatment with the immunomodulatory composition.

In some cases, an effective amount of an immunomodulatory composition of the present disclosure is an amount that is effective, when administered in a single dose or in multiple doses, to increase a Th1 response in an individual. For example, in some cases, an effective amount of an immunomodulatory composition of the present disclosure is an amount that is effective, when administered in a single dose or in multiple doses, to increase a Th1 response in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the level of the Th1 response in the individual in the absence of treatment with the immunomodulatory composition.

In some cases, an effective amount of an immunomodulatory composition of the present disclosure is an amount that is effective, when administered in a single dose or in multiple doses, to increase the number and/or activity of CD4$^+$ T cells in an individual. For example, in some cases, an effective amount of an immunomodulatory composition of the present disclosure is an amount that is effective, when administered in a single dose or in multiple doses, to increase the number and/or activity of CD4$^+$ T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of CD4$^+$ T cells in the individual in the absence of treatment with the immunomodulatory composition. In some cases, an effective amount of an immunomodulatory composition of the present disclosure is an amount that is effective, when administered in a single dose or in multiple doses, to increase the number and/or activity of antigen-specific CD4$^+$ T cells in an individual. For example, in some cases, an effective amount of an immunomodulatory composition of the present disclosure is an amount that is effective, when administered in a single dose or in multiple doses, to increase the number and/or activity of antigen-specific CD4$^+$ T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of antigen-specific CD4$^+$ T cells in the individual in the absence of treatment with the immunomodulatory composition.

In some cases, an effective amount of an immunomodulatory composition of the present disclosure is an amount that is effective, when administered in a single dose or in multiple doses, to increase the number and/or activity of CD8$^+$ T cells in an individual. For example, in some cases, an effective amount of an immunomodulatory composition of the present disclosure is an amount that is effective, when administered in a single dose or in multiple doses, to increase the number and/or activity of CD8$^+$ T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of CD8$^+$ T cells in the individual in the absence of treatment with the immunomodulatory composition. In some cases, an effective amount of an immunomodulatory composition of the present disclosure is an amount that is effective, when administered in a single dose or in multiple doses, to increase the number and/or activity of antigen-specific CD8$^+$ T cells in an individual. For example, in some cases, an effective amount of an immunomodulatory composition of the present disclosure is an amount that is effective, when administered in a single dose or in multiple doses, to increase the number and/or activity of antigen-specific CD8$^+$ T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of antigen-specific CD8$^+$ T cells in the individual in the absence of treatment with the immunomodulatory composition.

In some cases, an effective amount of an immunomodulatory composition of the present disclosure is an amount that is effective, when administered in a single dose or in multiple doses, to increase the number and/or activity of cytolytic T cells in an individual. For example, in some cases, an effective amount of an immunomodulatory composition of the present disclosure is an amount that is effective, when administered in a single dose or in multiple doses, to increase the number and/or activity of cytolytic T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of cytolytic T cells in the individual in the absence of treatment with the immunomodulatory composition. In some cases, an effective amount of an immunomodulatory composition of the present disclosure is an amount that is effective, when administered in a single dose or in multiple doses, to increase the number and/or activity of antigen-specific cytolytic T cells in an individual. For example, in some cases, an effective amount of an immunomodulatory composition of the present disclosure is an amount that is effective, when administered in a single dose or in multiple doses, to increase the number and/or activity of antigen-specific cytolytic T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of antigen-specific cytolytic T cells in the individual in the absence of treatment with the immunomodulatory composition.

In some cases, an effective amount of an immunomodulatory composition of the present disclosure is an amount that is effective, when administered in a single dose or in multiple doses, to increase the number and/or activity of one or more of natural killer (NK) cells, NKT cells, macrophages, and dendritic cells (DCs) in an individual. For example, in some cases, an effective amount of an immunomodulatory composition of the present disclosure is an amount that is effective, when administered in a single dose or in multiple doses, to increase the number and/or activity of one or more of NK cells, NKT cells, macrophages, and DCs in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of one or more of NK cells, NKT cells, macrophages, and DCs in the individual in the absence of treatment with the immunomodulatory composition.

In some cases, an effective amount of an immunomodulatory composition of the present disclosure is an amount that is effective, when administered in a single dose or in multiple doses, to increase, decrease or balance the number and/or function of Tregs in an individual. Tregs (regulatory T cells) are $CD4^+$ or $CD8^+$, and may also be $FoxP3^+$. $T_{regs}$ may also be defined by other markers such as PD-1, CTLA-4 etc. Regulatory cells may also be comprised of other innate cells such as NK, NKT and DCs, and B lymphocytes. For example, in some cases, an effective amount of an immunomodulatory composition of the present disclosure is an amount that is effective, when administered in a single dose or in multiple doses, to modulate the number of Tregs in an individual by at least 10%, at least 15%, at least 20%, at least 25%, at least 30%, at least 35%, at least 40%, at least 45%, at least 50%, at least 75%, or more than 75%, compared to the number of Tregs in the individual in the absence of treatment with the immunomodulatory composition. For example, in some cases, an effective amount of an immunomodulatory composition of the present disclosure is an amount that is effective, when administered in a single dose or in multiple doses, to reduce the number of Tregs in an individual by at least 10%, at least 15%, at least 20%, at least 25%, at least 30%, at least 35%, at least 40%, at least 45%, at least 50%, at least 75%, or more than 75%, compared to the number of Tregs in the individual in the absence of treatment with the immunomodulatory composition.

In some cases, an effective amount of an immunomodulatory composition of the present disclosure is an amount that is effective, when administered in a single dose or in multiple doses, to increase the number and/or activity of Th17 cells in an individual. For example, in some cases, an effective amount of an immunomodulatory composition of the present disclosure is an amount that is effective, when administered in a single dose or in multiple doses, to increase the number and/or activity of Th17 cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of Th17 cells in the individual in the absence of treatment with the immunomodulatory composition. In some cases, an effective amount of an immunomodulatory composition of the present disclosure is an amount that is effective, when administered in a single dose or in multiple doses, to increase the number and/or activity of antigen-specific Th17 cells in an individual. For example, in some cases, an effective amount of an immunomodulatory composition of the present disclosure is an amount that is effective, when administered in a single dose or in multiple doses, to increase the number and/or activity of antigen-specific Th17 cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of antigen-specific Th17 cells in the individual in the absence of treatment with the immunomodulatory composition.

In some cases, an effective amount of an immunomodulatory composition of the present disclosure is an amount that is effective, when administered in a single dose or in multiple doses, to increase the number and/or activity of Th22 cells in an individual. For example, in some cases, an effective amount of an immunomodulatory composition of the present disclosure is an amount that is effective, when administered in a single dose or in multiple doses, to increase the number and/or activity of Th22 cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of Th22 cells in the individual in the absence of treatment with the immunomodulatory composition. In some cases, an effective amount of an immunomodulatory composition of the present disclosure is an amount that is effective, when administered in a single dose or in multiple doses, to increase the number and/or activity of antigen-specific Th22 cells in an individual. For example, in some cases, an effective amount of an immunomodulatory composition of the present disclosure is an amount that is effective, when administered in a single dose or in multiple doses, to increase the number and/or activity of antigen-specific Th22 cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of antigen-specific Th22 cells in the individual in the absence of treatment with the immunomodulatory composition.

In some cases, an effective amount of an immunomodulatory composition of the present disclosure is an amount that is effective, when administered in a single dose or in multiple doses, to elicit, boost and/or regulate innate and/or adaptive (including both cellular and humoral) immune responses in an individual. For example, in some cases, an effective amount of an immunomodulatory composition of the present disclosure is an amount that is effective, when administered in a single dose or in multiple doses, to modulate the number and/or activity of innate and/or adaptive immune cells and/or their effector functions in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of one or more of innate or adaptive immune cells and/or their effector functions in the individual in the absence of treatment with the immunomodulatory composition.

In some cases, an effective amount of an immunomodulatory composition of the present disclosure is an amount that is effective, when administered in a single dose or in multiple doses, to protect innate and/or adaptive immune cells from depletion or prevent their apoptosis in an individual. For example, in some cases, an effective amount of an immunomodulatory composition of the present disclosure is an amount that is effective, when administered in a single dose or in multiple doses, to protect innate and/or adaptive immune cells from depletion or prevent their apoptosis in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of one or more of innate or adaptive immune cells and/or their effector functions in the individual in the absence of treatment with the immunomodulatory composition.

In some cases, an immunomodulatory composition of the present disclosure comprises HKCC and an antigen. Where an immunomodulatory composition of the present disclosure comprises HKCC and an antigen, in some cases, an effective amount of an immunomodulatory composition of the present disclosure is an amount that is effective, when administered in a single dose or in multiple doses, to increase an immune response to the antigen by at least about 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the immune response to the antigen in the absence of treatment with the immunomodulatory composition. For example, where the antigen is an antigen associated with or derived from a cancer cell, a pathogenic bacterium, a pathogenic virus, or a pathogenic protozoan, an effective amount of an immunomodulatory composition of the present disclosure is an amount that is effective, when administered in a single dose or in multiple doses, to increase an immune response to the antigen by at least about 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the immune response to the antigen in the absence of treatment with the immunomodulatory composition. The immune response can be a humoral immune response, e.g., a B cell or antibody immune response. Thus, e.g., in some cases, where the antigen is an antigen associated with or derived from a cancer cell, a pathogenic bacterium, a pathogenic virus, or a pathogenic protozoan, an effective amount of an immunomodulatory composition of the present disclosure is an amount that is effective, when administered in a single dose or in multiple doses, to increase a B cell response to the antigen by at least about 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the B cell response to the antigen in the absence of treatment with the immunomodulatory composition. For example, in some cases, where the antigen is an antigen associated with or derived from a cancer cell, a pathogenic bacterium, a pathogenic virus, or a pathogenic protozoan, an effective amount of an immunomodulatory composition of the present disclosure is an amount that is effective, when administered in a single dose or in multiple doses, to increase the amount of antibody specific to the antigen by at least about 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the amount of antibody specific to the antigen in the absence of treatment with the immunomodulatory composition. The immune response can be a cellular immune response, e.g., a T cell immune response. Thus, e.g., in some cases, where the antigen is an antigen associated with or derived from a cancer, a pathogenic bacterium, a pathogenic virus, or a pathogenic protozoan, an effective amount of an immunomodulatory composition of the present disclosure is an amount that is effective, when administered in a single dose or in multiple doses, to increase a T cell response to the antigen by at least about 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the T cell response to the antigen in the absence of treatment with the immunomodulatory composition. In some cases, the immune response is a humoral immune response and a cellular immune response.

Adjuvants

In some embodiments, a subject method involves administration of a subject immunomodulatory composition, where the immunomodulatory composition comprises HKCC and one or more additional adjuvants.

Exemplary additional adjuvants include, but are not limited to: (1) oil-in-water emulsion formulations (with or without other specific immunostimulating agents such as muramyl peptides (see below) or bacterial cell wall components), such as for example (a) MF59™ (WO 90/14837; Chapter 10 in Vaccine design: the subunit and adjuvant approach, eds. Powell & Newman, Plenum Press 1995), containing 5% Squalene, 0.5% Tween 80, and 0.5% Span 85 (optionally containing MTP-PE) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), e.g., MPL+CWS (Detox™); (2) saponin adjuvants, such as QS21 or Stimulon™ (Cambridge Bioscience, Worcester, Mass.) may be used or particles generated therefrom such as ISCOMs (immunostimulating complexes), which ISCOMS may be devoid of additional detergent e.g. WO 00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12, IL-15, IL-28, etc.) (WO99/44636), etc.), interferons (e.g. gamma interferon), macrophage colony stimulating factor (M-CSF), tumor necrosis factor (TNF), colony-stimulating factors (e.g., GM-CSF), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO 00/56358; (6) combinations of 3dMPL with, for example, QS21 and/or oil-in-water emulsions e.g. EP-A-0835318, EP-A-0735898, EP-A-0761231; (7) oligonucleotides comprising CpG motifs (Krieg Vaccine 2000, 19, 618-622; WO 96/02555, WO 98/16247, WO 98/18810, WO 98/40100, WO 98/55495, WO 98/37919 and WO 98/52581), i.e., oligonucleotides containing at least one CG dinucleotide, where the cytosine is unmethylated; (8) a polyoxyethylene ether or a polyoxyethylene ester e.g. WO 99/52549; (9) a polyoxyethylene sorbitan ester surfactant in combination with an octoxynol (WO 01/21207) or a polyoxyethylene alkyl ether or ester surfactant in combination with at least one additional non-ionic surfactant such as an octoxynol (WO 01/21152); (10) a saponin and an immunostimulatory oligonucleotide (e.g. a CpG oligonucleotide) (WO 00/62800); (11) an immunostimulant and a particle of metal salt e.g. WO 00/23105; (12) a saponin and an oil-in-water emulsion e.g. WO 99/11241; (13) a saponin (e.g. QS21)+3dMPL+IM2 (optionally including a sterol) e.g. WO 98/57659; (14) alphaGalCer and its derivatives; (16) toll-like receptor (TLR) agonists, NOD-like receptor (NLR) agonists, RIG-I agonists, agonists for C-type lectin receptors and other pathogen recognition receptor (PRR) agonists e.g., CpG ODNs, ISS-ODNs, rinatolimod, polyI:C and its derivatives, flagellin, ampligen, imidazoquinalines (e.g., imiquimod, resiquimod), muramyl dipeptides; (17) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc. Adjuvants suitable for administration to a human included in some cases.

Further exemplary additional adjuvants include, but are not limited to: cholera toxin B subunit, BCG, Pseudomonas aeruginosa exoprotein A, tocopherol, HBV core, E. coli heat labile toxins (such as LT-A, LT-B), Pertussis toxin, Diphtheria toxoid, tetanus toxoid, Cholera toxin derived (CTA1-DD, CT), mutant LT and CT, Aluminium salt-based adjuvants (such as Alum, Aluminum phosphate, Aluminum sulphate, Alhydrogel), Calcium phosphate, kaolin, monophosphoryl lipid A ($MPL^R$) and its derivatives, glucoppyranosyl lipid A, synthetic lipid A, Lipid A mimetics, Vitamin E, Depovax™, Saponins (Quil-A, AS01, AS02 (squalene+MPL+QS-21)), AS03, AS04 (alum+$MPL^R$), Tomatin, Protolin, RC-529, Pluronic™, Monatides, Matrix-M, OM-174, Lipovac, IC-31, bacterial/mycobacterial peptides (such as KLK, cationic (poly)peptides, anti-bacterial microbial peptides, defensins, tuftsin, cathelicidin), dipeptides (such as pidotimod), Bestatin, Hepon (tetradecapeptide), SCV-07 (gamma-D-glutamyl-L-tryptophan), Thymosin-a, Immunofan, Thymogen, Indolicidin and its derivatives, polyphosphagene and its derivatives, Gellan, nucleotides (mononucleotides, dinucleotides, polynucleotides, cyclic nucleotides), Eurocine etc.

Combination Therapy

In some embodiments, a subject method involves administration of a subject immunomodulatory composition as monotherapy, e.g., administration of a subject immunomodulatory composition only, without co-administration of any other therapeutic agent. In other embodiments, a subject treatment method is a combination therapy involving administration of: a) a subject immunomodulatory composition; and b) at least one additional therapeutic agent (or a pharmaceutically acceptable salt, prodrugs, salts of prodrugs, stereoisomers, tautomers etc. of the therapeutic agent), where the immunomodulatory composition and the at least one additional therapeutic agent are administered in combined amounts that are effective to modulate an immune response. Suitable additional therapeutic agents are described below.

A subject combination therapy can involve: a) administration of an immunomodulatory composition and at least one additional therapeutic agent at the same time, in the same formulation or in separate formulations; b) administration of at least one additional therapeutic agent within about 5 minutes to about 4 weeks of administration of an immunomodulatory composition, e.g., administration of at least one additional therapeutic agent within about 5 minutes to about 15 minutes, within about 15 minutes to about 30 minutes, within about 30 minutes to about 60 minutes, within about 1 hour to about 2 hours, within about 2 hours to about 4 hours, within about 4 hours to about 8 hours, within about 8 hours to about 12 hours, within about 12 hours to about 24 hours, within about 24 hours to about 2 days, within about 2 days to about 4 days, within about 4 days to about 7 days, within about 1 week to about 2 weeks, or within about 2 weeks to about 4 weeks of administration of an immunomodulatory composition.

In some embodiments, the at least one additional therapeutic agent is co-formulated with the immunomodulatory composition. In other embodiments, the at least one additional therapeutic agent and the immunomodulatory composition are separately formulated.

In some embodiments, an effective amount of an immunomodulatory composition and an at least one additional therapeutic agent are synergistic amounts. As used herein, a "synergistic combination" or a "synergistic amount" of a subject immunomodulatory composition and an additional (e.g., a second) therapeutic agent is a combination or amount that is more effective in the therapeutic or prophylactic treatment of a disease than the incremental improvement in treatment outcome that could be predicted or expected from a merely additive combination of (i) the therapeutic or prophylactic benefit of the immunomodulatory composition when administered at that same dosage as a monotherapy and (ii) the therapeutic or prophylactic benefit of the additional therapeutic agent when administered at the same dosage as a monotherapy.

A subject combination therapy can involve: administration of an immunomodulatory composition and at least one additional form of therapy such as radiation therapy (comprising radioisotopes such as $^{125}$I, strontium-89, $^{32}$P, alpha-emitting isotopes, beta-emitting isotopes etc.), photodynamic therapy, laser therapy, natural product therapy, nutraceutical therapy, cellular therapy, prebiotic therapy, probiotic therapy, symbiotic therapy, paraprobiotic therapy etc., given at the same or different times.

In some embodiments, an effective amount of an immunomodulatory composition can be administered in a heterologous or homologous prime-boost vaccine, immunotherapy and/or chemotherapy regimen(s).

A subject combination therapy can involve: administration of an immunomodulatory composition and a therapeutic vaccine.

A subject combination therapy can involve: administration of an immunomodulatory composition and a therapeutic antibody. For example, in some embodiments, a subject method involves: a) administration of an immunomodulatory composition of the present disclosure; and b) administration of at least one antibody. The HKCC and the antibody can be in the same formulation or in separate formulations. The HKCC and the antibody can be administered simultaneously, or at different times. Suitable antibodies include an antibody against a cancer antigen or a pathogenic antigen (e.g., a therapeutic antibody, monoclonal antibodies, bispecific antibodies, chemoimmuno conjugated antibodies, radioimmunoconjugated antibodies, antibody-cytokine fusion proteins, antibody-antigen fusion proteins, antibody-immunotoxin fusion protein etc.). Suitable antibodies include, without limitation, antibodies directed against co-stimulatory or co-inhibitory molecules (CD28, CD40, CTLA-4, PD-1 etc.); and other therapeutic antibodies. Non-limiting examples of suitable antibodies include, but are not limited to, adalimumab, bevacizumab, infliximab, abciximab, alemtuzumab, bapineuzumab, basiliximab, belimumab, briakinumab, brodalumab, canakinumab, certolizumab pegol, cetuximab, conatumumab, denosumab, eculizumab, etrolizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumornab, pertuzumab, ranibizumab, rituximab, rovelizumab, tocilizumab, tositumomab, trastuzumab, ustekinumab, vedolizumab, zalutumumab, and zanolimumab.

Non-limiting examples of therapeutic and prophylactic antibodies that can be used in combination therapy with an immunomodulatory composition of the present disclosure include MDX-010 (Medarex, N.J.) which is a humanized anti-CTLA-4 antibody for the treatment of prostate cancer; SYNAGIS™ (MedImmune, Md.) which is a humanized anti-respiratory syncytial virus (RSV) monoclonal antibody for the treatment of RSV infection; and HERCEPTIN™ (Trastuzumab) (Genentech, Calif.) which is a humanized anti-HER2 monoclonal antibody for the treatment of metastatic breast cancer. Other examples are humanized anti-CD18 F(ab')$_2$ (Genentech); CDP860 which is a humanized anti-CD18 F(ab')$_2$ (Celltech, UK); PRO542 which is an anti-HIV gp120 antibody fused with CD4 (Progenics/Genzyme Transgenics); Ostavir which is a human anti-Hepatitis B virus antibody (Protein Design Lab/Novartis); PROTOVIR™ which is a humanized anti-CMV IgGI antibody (Protein Design Lab/Novartis); MAK-195 (SEGARD) which is a murine anti-TNF-α (Knoll Pharma/BASF); IC14 which is an anti-CD14 antibody (ICOS Pharm); a humanized anti-VEGF IgG1 antibody (Genentech); OVAREX™ which is a murine anti-CA 125 antibody (Altarex); PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti-CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); Smart ID10 which is a humanized anti-HLA antibody (Protein Design Lab); ONCOLYM™ (Lym-1) is a radiolabelled murine anti-HLA DIAGNOSTIC REAGENT antibody (Techniclone); ABX-IL8 is a human anti-IL8 antibody (Abgenix); anti-CD11a is a humanized IgG1 antibody (Genentech/Xoma); ICM3 is a humanized anti-ICAM3 antibody (ICOS Pharm); IDEC-114 is a primatized anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); MDX-33 is a human anti-CD64 (FcγR) antibody (Medarex/Centeon); SCH55700 is a humanized anti-IL-5 IgG4 antibody (Celltech/Schering); SB-240563 and SB-240683 are humanized anti-IL-5 and IL-4 antibodies, respectively, (SmithKline Beecham); rhuMab-E25 is a humanized anti-IgE IgG1 antibody (Genentech/Norvartis/Tanox Biosystems); ABX-CBL is a murine anti CD-147 IgM antibody (Abgenix); BTI-322 is a rat anti-CD2 IgG antibody (MedImmune/Bio Transplant); Orthoclone/OKT3 is a murine anti-CD3 IgG2a antibody (ortho Biotech); SIMULECT™ is a chimeric anti-CD25 IgG1 antibody (Novartis Pharm); LDP-01 is a humanized anti-$\beta_2$-integrin IgG antibody (LeukoSite); Anti-LFA-1 is a murine anti CD18 F(ab').sub.2 (Pasteur-Merieux/Immunotech); CAT-152 is a human anti-TGF-$\beta_2$ antibody (Cambridge Ab Tech); and Corsevin M is a chimeric anti-Factor VII antibody (Centocor). The above-listed immunoreactive reagents, as well as any other immunoreactive reagents, may be administered according to any regimen known to those of skill in the art, including the regimens recommended by the suppliers of the immunoreactive reagents.

A subject combination therapy can involve: administration of an immunomodulatory composition of the present disclosure and one or more cytokines. For example, in some embodiments, a subject method involves: a) administration of an immunomodulatory composition of the present disclosure; and b) administration of one or more cytokines. The HKCC and the one or more cytokines can be in the same formulation or in separate formulations. The HKCC and the one or more cytokines can be administered simultaneously, or at different times. Suitable cytokines include, without limitation, interleukins, transforming growth factors (TGFs), fibroblast growth factors (FGFs), platelet derived growth factors (PDGFs), epidermal growth factors (EGFs), colony stimulating factors (CSFs), connective tissue activated peptides (CTAPs), osteogenic factors, and biologically active analogs, fragments, and derivatives of such growth factors. Suitable cytokines include B/T-cell differentiation factors, B/T-cell growth factors, mitogenic cytokines, chemotactic cytokines, colony stimulating factors, angiogenesis factors, IFN-$\alpha$, IFN-$\beta$, IFN-$\gamma$, IL1, IL2, IL3, IL4, IL5, IL6, IL7, IL8, IL9, IL10, IL11, IL12, IL13, IL14, IL15, IL16, IL17, IL18, IL22, etc., leptin, myostatin, macrophage stimulating protein, platelet-derived growth factor, tumor necrosis factor (TNF)-alpha (TNF-$\alpha$), TNF-$\beta$, nerve growth factor (NGF), CD40L, CD137L/4-1BBL, human lymphotoxin-$\beta$, G-CSF, M-CSF, GM-CSF, platelet-derived growth factor (PDGF), IL-1a, IL1-$\beta$, IP-10, PF4, GRO, 9E3, erythropoietin, endostatin, angiostatin, vascular endothelial growth factor (VEGF) or any fragments or combinations thereof. Other cytokines include members of the transforming growth factor (TGF) supergene family include the beta transforming growth factors (for example TGF-$\beta$1, TGF-$\beta$2, TGF-$\beta$3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); hematopoietic growth factors (Flt3); pituitary growth hormones or derivatives; growth hormones, neuroactive hormones, Inhibins (for example, Inhibin A, Inhibin B); differentiation factors (for example, GDF-1); and Activins (for example, Activin A, Activin B, Activin AB).

A subject combination therapy can involve: administration of an immunomodulatory composition of the present disclosure and one or more therapeutic agents such as anti-angiogenic agents (e.g., in methods for the treatment of solid tumors and for the treatment and prevention of metastases) and anti-hormonal agents (particularly in methods for the treatment of hormone-dependent cancers such as breast cancer and prostate cancer).

In one embodiment, an immunomodulatory composition of the present disclosure is administered in combination with one or more anti-angiogenic agents. Such agents include, without limitation, angiostatin, thalidomide, kringle 5, endostatin, Serpin (Serine Protease Inhibitor) anti-thrombin, 29 kDa N-terminal and a 40 kDa C-terminal proteolytic fragments of fibronectin, 16 kDa proteolytic fragment of prolactin, 7.8 kDa proteolytic fragment of platelet factor-4, a 13-amino acid peptide corresponding to a fragment of platelet factor-4 (Maione et al., 1990, Cancer Res. 51:2077-2083), a 14-amino acid peptide corresponding to a fragment of collagen I (Tolma et al., 1993, J. Cell Biol. 122:497-511), a 19 amino acid peptide corresponding to a fragment of Thrombospondin I (Tolsma et al., 1993, J. Cell Biol. 122: 497-511), a 20-amino acid peptide corresponding to a fragment of SPARC (Sage et al., 1995, J. Cell. Biochem. 57:1329-1334), or any fragments, family members, or variants thereof, including pharmaceutically acceptable salts thereof.

Other peptides that inhibit angiogenesis and correspond to fragments of laminin, fibronectin, procollagen, and EGF have also been described (see, e.g., Cao, 1998, Prog Mol Subcell Biol. 20:161-176). Monoclonal antibodies and cyclic pentapeptides, which block certain integrins that bind RGD proteins (i.e., possess the peptide motif Arg-Gly-Asp), have been demonstrated to have anti-vascularization activities (Brooks et al., 1994, Science 264:569-571; Hammes et al., 1996, Nature Medicine 2:529-533). Moreover, inhibition of the urokinase plasminogen activator receptor by receptor antagonists inhibits angiogenesis, tumor growth and metastasis (Min et al., 1996, Cancer Res. 56: 2428-33; Crowley et al., 1993, Proc Natl Acad Sci. 90:5021-25).

In another embodiment, a combination therapy of the present disclosure comprises administering an immunomodulatory composition of the present disclosure together with a hormonal treatment modality. Such treatment modalities include the administration of hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), and antiandrogens (e.g., cyproterone acetate).

In another embodiment, an immunomodulatory composition of the present disclosure is used in association with a treatment modality that utilizes polynucleotide compounds, such as antisense polynucleotides, ribozymes, RNA interference molecules, triple helix polynucleotides and the like.

In certain embodiments, an immunomodulatory composition of the present disclosure is administered in combination with an immunoregulatory agent. In some embodiments, the immunomodulatory composition is formulated with the immunoregulatory agent. An "immunoregulatory agent" is a substance that suppresses, masks, or enhances the immune system of the subject to whom it is administered. Exemplary agents are those that suppress cytokine production, downregulate or suppress self-antigen expression, or mask the MHC antigens. Examples of such agents include 2-amino-6-aryl-5-substituted pyrimidines (see, U.S. Pat. No. 4,665,077), azathioprine (or cyclophosphamide, if there is an adverse reaction to azathioprine); bromocryptine; glutaraldehyde (which masks the MHC antigens, as described in U.S. Pat. No. 4,120,649); anti-idiotypic antibodies for MHC antigens and MHC fragments; cyclosporin A; steroids such as glucocorticosteroids, e.g., prednisone, methylprednisolone, and dexamethasone; cytokine or cytokine receptor antagonists including anti-interferon-γ, -β, or α antibodies; anti-tumor necrosis factor-a antibodies; anti-tumor necrosis factor-.beta. antibodies; anti-interleukin-2 antibodies and anti-IL-2 receptor antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain; streptokinase; TGF-β; streptodomase; FK506; RS-61443; deoxyspergualin; and rapamycin. Examples of cytokines include, but are not limited to lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α; mullerian-inhibiting substance; mouse gonadotropin-associated peptide; inhibin; activin; vascular endothelial growth factor; integrin; thrombopoietin (TPO); nerve growth factors such as NGF-α; platelet-growth factor; transforming growth factors (TGFs) such as TGF-α and TGF-β; insulin-like growth factor-I and -II; erythropoietin (EPO); osteoinductive factors; interferons; colony stimulating factors (CSFs) such as macrophage-CSF (M-CSF); granulocyte-macrophage-CgP (GM-CSP); and granulocyte-CSF (G-CSF); interleukins (ILs) such as IL-1, IL-1a, IL-2, IL-3, IL-4, IL-5, IL-6, IL-7, IL-8, IL-9, IL-11, IL-12, IL-15; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

In certain embodiments, an immunomodulatory composition of the present disclosure is administered in combination therapy with one or more immunomodulatory agents, e.g., a cytokine. Suitable cytokines include, but are not limited to, interleukin-1 (IL-1), IL-2, IL-3, IL-12, IL-15, IL-18, G-CSF, GM-CSF, thrombopoietin, and γ interferon.

In certain embodiments, an immunomodulatory composition of the present disclosure is administered in combination with a compound that enhances monocyte or macrophase function. In certain embodiments, a compound that enhances monocyte or macrophage function (e.g., at least about 25%, 50%, 75%, 85%, 90%, 9% or more) can be used in conjunction with an immunomodulatory composition of the present disclosure. Such compounds are known in the art and include, without limitation, cytokines such as interleukins (e.g., IL-12), and interferons (e.g., alpha or gamma interferon). In certain embodiments, the compound that enhances monocyte or macrophage function is formulated with an immunomodulatory composition of the present disclosure and is thus administered concurrently with the immunomodulatory composition of the present disclosure. In other embodiments, the compound that enhances monocyte or macrophage function is administered separately from the immunomodulatory composition of the present disclosure and can be administered concurrently (within a period of hours of each other), during the same course of therapy, or sequentially with the immunomodulatory composition of the present disclosure. In some embodiments, the compound that enhances monocyte or macrophage function is administered to a human subject. In one embodiment, the human subject has a blood leukocyte, monocyte, neutrophil, lymphocyte, and/or basophil count that is within the normal range for humans. Normal ranges for human blood leukocytes (total) are about 3.5-10.5 ($10^9$/L). Normal ranges for human blood neutrophils are about 1.7-7.0 ($10^9$/L), monocytes is about 0.3-0.9 ($10^9$/L), lymphocytes is about 0.9-2.9 ($10^9$/L) basophils is about 0-0.3 ($10^9$/L), and eosinophils is about 0.05-0.5 ($10^9$/L). In other embodiments, the human subject has a blood leukocyte count that is less than the normal range for humans, for example at least about 0.01, 0.05, 0.1, 0.2, 0.3, 0.4, 0.5, 0.6, 0.7, or 0.8 ($10^9$/L) leukocytes.

Methods of Enhancing an Anti-Bacterial Immune Response

The present disclosure provides methods of enhancing an immune response to a bacterium or a substance produced by a bacterium, the method comprising administering to an individual in need thereof an effective amount of an immunomodulatory composition of the present disclosure. In some cases, a method of the present disclosure of enhancing an immune response to a bacterium or a substance produced by a bacterium comprises administering to an individual in need thereof an effective amount of an immunomodulatory composition of the present disclosure, where the immunomodulatory composition comprises a bacterial antigen (other than an antigen of HKCC). Suitable bacterial antigens are described above.

In some cases, a method of the present disclosure of enhancing an immune response to a bacterium, or a substance produced by a bacterium, is effective to reduce the number of bacteria (e.g., pathogenic bacteria) in the individual by at least about 25%, at least about 50%, at least about 75%, or at least about 99%, compared to a pre-treatment number of pathogenic bacteria in the individual, or to an extent that the pathogenic bacterium cannot be detected in the individual (e.g., in a biological sample obtained from the individual).

In some cases, a method of the present disclosure of enhancing an immune response to a bacterium, or a substance produced by a bacterium, is effective to induce or enhance an immune response to a pathogenic bacterium. Pathogenic bacteria include, e.g., Gram positive bacteria, Gram negative bacteria, mycobacteria, etc. Non-limiting examples of pathogenic bacteria include Mycobacteria, *Streptococcus, Staphylococcus, Pseudomonas, Salmonella, Neisseria,* and *Listeria*. In some cases, the bacteria is *Neisseria gonorrhea, M. tuberculosis, M. leprae, Listeria monocytogenes, Streptococcus pneumoniae, S. pyogenes, S. agalactiae, S. viridans, S. faecalis, S. aureus, S. epidermis,* or S. *Bovis*.

Other examples of pathogenic bacteria contemplated include, but are not limited to, Gram positive bacteria (e.g., *Listeria, Bacillus* such as *Bacillus anthracis, Erysipelothrix* species), Gram negative bacteria (e.g., *Bartonella, Brucella, Burkholderia, Campylobacter, Enterobacter, Escherichia, Francisella, Hemophilus, Klebsiella, Morganella, Proteus, Providencia, Pseudomonas, Salmonella, Serratia, Shigella, Vibrio,* and *Yersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, *Pneumococcus* species, *Staphylococcus* species, *Neisseria* species.

Additional non-limiting examples of specific infectious bacteria include *Citrobacter, Helicobacter pylori, Borelia burgdorferi, Legionella pneumophila, Mycobacteria avium, M. intracellulare, M. kansaii, M. gordonae, M. africanum, Staphylococcus aureus, Neisseria meningitidis, Haemophilus influenzae, Bacillus anthracis, Yersinia pestis, Corynebacterium diphtheriae, Erysipelothrix rhusiopathiae, Clostridium perfringens, Clostridium tetani, Enterobacter aerogenes, Klebsiella pneumoniae, Pasteurella multocida, Fusobacterium nucleatum, Streptobacillus moniliformis, Treponema pallidium, Treponema pertenue, Leptospira, Rickettsia, Porphyromonas gingivalis*, and *Actinomyces israelli*.

In some cases, a method of the present disclosure of enhancing an immune response to a bacterium, or a substance produced by a bacterium, comprises administering an immunomodulatory composition to an individual in need thereof, and further comprising administering to the individual an effective amount of an anti-bacterial or an anti-mycobacterial agent. Anti-bacterial and anti-mycobacterial agents are known in the art and include, e.g., beta-lactam antibiotics, tetracyclines, streptomycin, chloramphenicol, neomycin, gramicidin, bacitracin, sulfonamides, nitrofurazone, nalidixic acid, rifampicin, fluoroquinolones, isoniazid, pyrazinamide, vancomycin, methicillin etc.

Suitable anti-bacterial agents include, e g, Aminoglycosides such as Amikacin, Apramycin, Arbekacin, Bambermycins, Butirosin, Dibekacin, Dihdrostreptomycin, Fortimicin(s), Gentamicin, Ispamicin, Kanamycin, Micronomicin, Neomycin, Neomycin Undecylenate, Netilmicin, Paromomycin, Ribostamycin, Sisomicin, Spectinomycin, Streptomycin, Streptonicozid and Tobramycin; Ansamycins such as Rifamide, Rifampin, Rifamycin and Rifaximin; β-lactams such as Carbapenems such as Imipenem; Cephalosporins such as Cefactor, Cefadroxil, Cefamandole, Cefatrizine, Cefazedone, Cefazolin, Cefixime, Cefinenoxime, Cefodizime, Cefonicid, Cefoperazone, Ceforanide, Cefotaxime, Cefotiam, Cefpimizole, Cefpirimide, Cefpodoxime Proxetil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine and Pivcefalexin; Cephamycins such as Cefbuperazone, Cefmetazole, Cefminox, Cefetan and Cefoxitin; Monobactams such as Aztreonam, Carumonam and Tigemonam; Oxacephems such as Flomoxef and Moxolactam; Penicillins such as Amidinocillin, Amdinocillin Pivoxil, Amoxicillin, Ampicillan, Apalcillin, Aspoxicillin, Azidocillan, Azlocillan, Bacampicillin, Benzylpenicillinic Acid, Benzylpenicillin Sodium, Carbenicillin, Carfecillin Sodium, Carindacillin, Clometocillin, Cloxacillin, Cyclacillin, Dicloxacillin, Diphenicillin Sodium, Epicillin, Fenbenicillin, Floxicillin, Hetacillin, Lenampicillin, Metampicillin, Methicillin Sodium, Mezlocillin, Nafcillin Sodium, Oxacillin, Penamecillin, Penethamate Hydriodide, Penicillin G Benethamine, Penicillin G Benzathine, Penicillin G Benzhydrylamine, Penicillin G Calcium, Penicillin G Hydrabamine, Penicillin G Potassium, Penicillin G Procaine, Penicillen N, Penicillin O, Penicillin V, Penicillin V Benzathine, Penicillin V Hydrabamine, Penimepicycline, Phenethicillin Potassium, Piperacillin, Pivapicillin, Propicillin, Quinacillin, Sulbenicillin, Talampicillin, Temocillin and Ticarcillin; Lincosamides such as Clindamycin and Lincomycin; Macrolides such as Azithromycin, Carbomycin, Clarithromycin, Erythromycin, Erythromycin Acistrate, Erythromycin Estolate, Erythromycin Glucoheptonate, Erythromycin Lactobionate, Erythromycin Propionate, Erythromycin Stearate, Josamycin, Leucomycins, Midecamycins, Miokamycin, Oleandomycin, Primycin, Rokitamycin, Rosaramicin, Roxithromycin, Spiramycin and Troleandomycin; Polypeptides such as Amphomycin, Bacitracin, Capreomycin, Colistin, Enduracidin, Enviomycin, Fusafungine, Gramicidin(s), Gramicidin S, Mikamycin, Polymyxin, Polymyxin B-Methanesulfonic Acid, Pristinamycin, Ristocetin, Teicoplanin, Thiostrepton, Tuberactinomycin, Tyrocidine, Tyrothricin, Vancomycin, Viomycin, Viomycin Pantothenate, Virginiamycin and Zinc Bacitracin; Tetracyclines such as Apicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Senociclin and Tetracycline; Cycloserine; Mupirocin; and Tuberin. Suitable anti-bacterial agents include antibodies specific for a bacterium.

Methods of Enhancing an Anti-Viral Immune Response

The present disclosure provides methods of enhancing an immune response to a virus, the method comprising administering to an individual in need thereof an effective amount of an immunomodulatory composition of the present disclosure. In some cases, a method of the present disclosure of enhancing an immune response to a virus comprises administering to an individual in need thereof an effective amount of an immunomodulatory composition of the present disclosure, where the immunomodulatory composition comprises a viral antigen. Suitable viral antigens are described above.

In some cases, a method of the present disclosure of enhancing an immune response to a virus is effective to reduce the number of viruses (e.g., pathogenic viruses) in the individual by at least about 25%, at least about 50%, at least about 75%, or at least about 99%, or to an extent that the pathogenic virus cannot be detected in the individual (e.g., in a biological sample obtained from the individual).

For example, in some cases, a method of the present disclosure of enhancing an immune response to a virus is effective to reduce the viral load in the individual by at least about 25%, at least about 50%, at least about 75%, or at least about 99%, or to an extent that the pathogenic virus cannot be detected in the individual (e.g., in a biological sample obtained from the individual). In some cases, a method of the present disclosure of enhancing an immune response to a virus is effective to reduce the number of genome copies of the virus in the individual by at least about 25%, at least about 50%, at least about 75%, or at least about 99%, compared to a pre-treatment number of genome copies of the virus in the individual, or to an extent that no genome copies of the virus can be detected in the individual (e.g., in a biological sample obtained from the individual).

In some cases, a method of the present disclosure of enhancing an immune response to a virus induces or increases an immune response to a pathogenic virus. Pathogenic viruses include, but are not limited to, herpes viruses (HSV-1, HSV-2, VZV, EBV, CMV, HHV-6, HHV-8), influenza viruses (Flu A, B), hepatitis viruses (HepA, HepB, HepC, HepD, HepE), human immunodeficiency viruses (HIV-1, HIV-2), respiratory syncytial viruses, measles viruses, rhinoviruses, adenoviruses, SARS viruses, papillomaviruses, orthopoxviruses, West Nile viruses, and a dengue viruses. Pathogenic viruses include members of the Flaviviridae family of viruses. Pathogenic viruses include a flavivirus selected from the group consisting of dengue, Kunjin, Japanese encephalitits, West Nile, and yellow fever virus. Pathogenic viruses include lymphocytic choriomenignitis virus, hepatitis B virus, Epstein Barr virus, and human immunodeficiency virus. Pathogenic viruses include, but are not limited to: Retroviridae (e.g. human immunodeficiency viruses, such as HIV-1, also referred to as LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronaviridae (e.g. coronaviruses); Rhabdoviridae (e.g. vesicular stomatitis viruses, rabies viruses); Filoviridae (e.g. ebola-like viruses; Marburg virus); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arenaviridae (hemorrhagic fever viruses); Reoviridae (e.g. reoviruses, orbiviurses and rotaviruses); Bornaviridae; Hepadnaviridae (Hepatitis B virus); Parvoviridae (parvoviruses); Papovaviridae (papilloma viruses, polyoma viruses); Adenoviridae (e.g., adenoviruses); Herpesviridae (herpes simplex virus (HSV) 1 and 2), varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the etiological agents of Spongiform encephalopathies, the agent of delta hepatitis, thought to be a defective satellite of hepatitis B virus), the agents of non-A, non-B hepatitis (class 1, internally transmitted; class 2, parenterally transmitted, i.e., Hepatitis C Virus); Norwalk and related viruses; and astroviruses.

In some cases, a method of the present disclosure of enhancing an immune response to a virus, comprises administering an immunomodulatory composition to an individual in need thereof, and further comprising administering to the individual an effective amount of at least one additional therapeutic agent, e.g., an anti-viral agent.

Anti-viral agents are known in the art and include, e.g., an anti-HCV agent such as ribavirin and its analogues; glycosidase inhibitors; glucosidase inhibitors; IRES (internal ribosomal entry site), p7, entry, fusion, helicase, assembly, egress, NS2, NS3, NS4, NS5a and NS5B inhibitors; inosine monophosphate dehydrogenase inhibitors; cyclophilin inhibitors; metalloprotease inhibitors; anti-HCV nucleos(t)ide and non-nucleoside RNA polymerase inhibitors etc.; an anti-HIV agent; anti-HBV agent; and the like.

In some embodiments, the at least one additional therapeutic agent is an interferon (e.g., interferon-alpha, interferon-beta, interferon-gamma, interferon-lambda, interferon-tau, interferon-omega, etc.). In some embodiments, the at least one additional therapeutic agent is IFN-α. In some embodiments, the at least one additional therapeutic agent is IFN-β.

Suitable additional anti-viral agents for treating an HCV infection include, but are not limited to, ribavirin and its prodrugs such as viramidine, telaprevir, sofosbuvir, boceprevir, ciluprevir, simeprevir, danoprevir, vaniprevir, MK-5172, MK-0608, 2'-C-methyl-7-deaza adenosine, 2'-C-methyl-adenosines, BI201335, narlaprevir, asunaprevir, GS-9256, GS-9451, ABT-450, IDX-320, ACH-1625, Valopicitabine, mericitabine, R1626, PSI-938, INX-189, BILN1941, BI-207127, VCH222, VX-135, ANA598, ANA773, ABT-072, ABT-333, HCV-796, GS-9190, Daclatasvir, BMS-824393, BMS-791325, PPI-461, GS-5885, alisporivir (Debio-025), NIM-811, SCY-635, nitazoxanide, clemizole, miravirasen, celgosivir, BCX-5191, GSK-2336805, anti-PD-1 antibodies (CT-011), bavituximab (anti-phosphatidyl serine Mab), therapeutic vaccine (GI-5005, IC-41, TG-4040) prophylactic vaccine (such as HCV E1/E2/MF-59), and the prodrugs thereof. Suitable additional therapeutic agents include, e.g., therapeutic agents for the treatment of an hepatitis B virus infection include, but are not limited to lamivudine, adefovir, entecavir, telbuvudine, tenofovir and the prodrugs thereof.

For example, suitable additional anti-viral agents for treating an HCV infection include weekly injections of pegylated IFN-α combined with twice-daily oral doses of ribavirin (1-β-D-ribofuranosyl-1H-1,2,4-triazole-3-carboxamide).

Suitable additional therapeutic agents include, e.g., therapeutic agents for the treatment of an immunodeficiency virus infection, or for the treatment of a disorder that may accompany an immunodeficiency virus infection (e.g., a bacterial infection, a fungal infection, and the like). Suitable additional therapeutic agents include, e.g., beta-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), cyanovirin-N, microvirin, fuzeon, anti-receptor antibodies (e.g., for rhinoviruses), nevirapine, cidofovir (Vistide™), trisodium phosphonoformate (Foscarnet™), famcyclovir, pencyclovir, valacyclovir, nucleic acid/replication inhibitors, interferon, zidovudine (AZT, Retrovir™), didanosine (dideoxyinosine, ddI, Videx™), stavudine (d4T, Zerit™), zalcitabine (dideoxycytosine, ddC, Hivid™), nevirapine (Viramune™), lamivudine (Epivir™, 3TC), protease inhibitors, saquinavir (Invirase™, Fortovase™), ritonavir (Norvir™), nelfinavir (Viracept™), efavirenz (Sustiva™), abacavir (Ziagen™), amprenavir (Agenerase™) indinavir (Crixivan™), ganciclovir, AzDU, delavirdine (Rescriptor™), kaletra, trizivir, rifampin, clathiromycin, erythropoietin, colony stimulating factors (G-CSF and GM-CSF), non-nucleoside reverse transcriptase inhibitors, nucleoside inhibitors, viral entry inhibitors, fusion inhibitors, integrase inhibitors, adriamycin, fluorouracil, methotrexate, asparaginase and combinations thereof. Additional suitable therapeutic agents for HIV include integrase and fusion inhibitors such as Raltegravir, Elvitegravir, Enfuvirtide, Maraviroc etc.

In some embodiments, the at least one additional therapeutic agent is a neuraminidase inhibitor, e.g., where the influenza virus is influenza A or influenza B. Suitable neuraminidase inhibitors include, e.g., oseltamivir (ethyl (3R,4R,5S)-5-amino-4-acetamido-3-(pentan-3-yloxy)cyclohex-1-ene-1-carboxylate; Tamiflu™), zanamivir (2R,3R,4S)-4-[(diaminomethylidene)amino]-3-acetamido-2-[(1R,2R-1,2,3-trihydroxypropyl]-3,4-dihydro-2H-pyran-6-carboxylic acid; Relenza™), and peramivir (1S,2S,3S,4R)-3-[(1S)-1-acetanaido-2-ethyl-butyl]-4-(diaminomethylideneamino)-2-hydroxy-cyclopentane-1-carboxylic acid). In some embodiments, the at least one additional therapeutic agent is an M2 blocker, e.g., blocks a viral ion channel (M2 protein). The antiviral drugs amantadine and rimantadine are M2 blockers, and can be used in subject method.

Suitable additional therapeutic agents, e.g., for the treatment of an HSV-1 or an HSV-2 infection include, but are not limited to, acyclovir (Zovirax), valganciclovir, famciclovir, valacyclovir (Valtrex), ganciclovir (Cytovene), cidofovir (Vistide), antisense oligonucleotide fomivirsen (Vitravene), foscarnet (Foscavir), penciclovir, idoxuridine, vidarabine, and trifluridine.

In some embodiments, the one or more different therapeutic agent is selected antiviral agents that target two or more different viruses; e.g., an HIV inhibitor, HBV inhibitor, HCV inhibitor, herpes virus inhibitor, influenza virus inhibitor, RNA inhibitor, interfering RNA (RNAi) inhibitor, natural products etc. In some cases, a method of the present disclosure of treating a viral infection comprises administering an immunomodulatory composition to an individual in need thereof, and further comprising administering to the individual an effective amount of at least one additional therapeutic agent, e.g., a monoclonal antibody or antibody products directed against viral antigens, where suitable monoclonal antibodies include but are not limited to HBIg, antibodies against influenza virus strains, anti-hepatitis A virus antibody, SYNAGIS (anti-RSV Mab), anti-rabies antibody, ostavir (anti-HBV Mab), Pro542 (anti-HIV gp120), Potovir (anti-CMV Mab), anti-PD-1 antibodies (CT-011), bavituximab (anti-phosphatidyl serine Mab) etc.

Methods of Enhancing an Immune Response to a Parasitic Infection

The present disclosure provides methods of enhancing an immune response to a microbial parasite (e.g., a pathogenic protozoan; a helminth; etc.), the method comprising administering to an individual in need thereof an effective amount of an immunomodulatory composition of the present disclosure. In some cases, a method of the present disclosure of enhancing an immune response to a microbial parasite comprises administering to an individual in need thereof an effective amount of an immunomodulatory composition of the present disclosure, where the immunomodulatory composition comprises an antigen derived from a microbial parasite (e.g., a protozoan antigen; a helminth antigen). Suitable microbial parasite antigens are described above.

In some cases, a method of the present disclosure of enhancing an immune response to a microbial parasite is effective to reduce the number of microbial parasites (e.g., pathogenic protozoa; pathogenic helminths) in the individual by at least about 25%, at least about 50%, at least about 75%, or at least about 99%, compared to a pre-treatment number of microbial parasite in the individual, or to an extent that the microbial parasite cannot be detected in the individual (e.g., in a biological sample obtained from the individual).

In some cases, a method of the present disclosure of enhancing an immune response to a microbial parasite comprises administering an immunomodulatory composition to an individual in need thereof, and further comprising administering to the individual an effective amount of a least one additional therapeutic agent. Anti-parasitic agents are known in the art and include, e.g., chloroquine, etc. For example, anti-malarial agents include, e.g., quinine, chloroquine, atovaquone, proguanil, primaquine, amodiaquine, mefloquine, piperaquine, artemisinin, methylene blue, pyrimethamine, sulfadoxine, artemether-lumefantrine, dapsone-chlorproguanil, artesunate, quinidine, clopidol, pyridine/pyridinol analogs, 4(1H)-quinolone analogs, dihydroartemisinin, a mixture of atovaquone and proguanil, an endoperoxide, and an acridone. Anti-parasitic agents include antibodies specific for the parasite.

In some cases, a method of the present disclosure of enhancing an immune response to a microbial parasite induces or increases an immune response to a microbial parasite such as *Plasmodium* spp., *Toxoplasma gondii*, *Babesia* spp., *Trichinella spiralis*, *Entamoeba histolytica*, *Giardia lamblia*, *Enterocytozoon bieneusi*, *Naegleria*, *Acanthamoeba*, *Trypanosoma rhodesiense* and *Trypanosoma gambiense*, *Isospora* spp., *Cryptosporidium* spp, *Eimeria* spp., *Neospora* spp., *Sarcocystis* spp., and *Schistosoma* spp.

In some cases, a method of the present disclosure of enhancing an immune response to a protozoan parasite induces or increases an immune response to a protozoan parasite such as *Giardia*; a *plasmodium* species (e.g., *Plasmodium falciparum*); *Toxoplasma gondii*; a *cryptosporidium*; a *Trichomonas* species; a trypanosome (e.g., *Trypanosoma cruzi*); or *Leishmania*.

Methods of Enhancing an Immune Response to a Pathogenic Fungus

The present disclosure provides methods of enhancing an immune response to a pathogenic fungus, the method comprising administering to an individual in need thereof an effective amount of an immunomodulatory composition of the present disclosure. In some cases, a method of the present disclosure of enhancing an immune response to a pathogenic fungus comprises administering to an individual in need thereof an effective amount of an immunomodulatory composition of the present disclosure, where the immunomodulatory composition comprises an antigen derived from a pathogenic fungus. Suitable fungal antigens are described above.

In some cases, a method of the present disclosure of enhancing an immune response to a pathogenic fungus is effective to reduce the number of fungal bodies in the individual by at least about 25%, at least about 50%, at least about 75%, or at least about 99%, compared to a pre-treatment number of fungal bodies in the individual, or to an extent that the pathogenic fungus cannot be detected in the individual (e.g., in a biological sample obtained from the individual).

In some cases, a method of the present disclosure of enhancing an immune response to a pathogenic fungus induces or increases an immune response to a fungus such as *Candida* spp. including *C. albicans*, *Aspergillus* spp., *Cryptococcus* spp. including *C. neoformans*, *Blastomyces* sp., *Pneumocytes* spp., or *Coccidioides* spp.

In some cases, a method of the present disclosure of enhancing an immune response to a pathogenic fungus comprises administering an immunomodulatory composition to an individual in need thereof, and further comprising administering to the individual an effective amount of a least one additional therapeutic agent. Anti-fungal agents are known in the art and include, e.g., flucanazole, 5-fluorocytosine, etc.

Suitable anti-fungal agents include, e.g., Polyenes such as Amphotericin-B (including various formulations of Amphotericin-B), Candicidin, Dermostatin, Filipin, Fungichromin, Hachimycin, Hamycin, Lucensomycin, Mepartricin, Natamycin, Nystatin, Pecilocin and Perimycin; and others such as Azaserine, Griseofulvin, Oligomycins, Neomycin Undecylenate, Pyrrolnitrin, Siccanin, Tubercidin and Viridin; Allylamines such as Naftifine and Terbinafine; Imidazoles such as Bifonazole, Butoconazole, Chlordantoin, Chlormidazole, Cloconazole, Clotrimazole, Econazole, Enilconazole, Fenticonazole, Isoconazole, Ketoconazole, Miconazole, Omoconazole, Oxiconazole, Nitrate, Sulconazole and Tioconazole; Triazoles such as Fluconazole, Itraconazole and Terconazole; and other others such as Acrisorcin, Amorolfine, Biphenamine, Bromosalicylchloranilide, Buclosamide, Calcium Propionate, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Tolciclate, Tolindate, Tolnaftate, Tricetin, Ujothion, Undecylenic Acid and Zinc Propionate.

Methods of Treating an Allergic Disease

The present disclosure provides methods of treating an allergic disease in an individual, the method comprising administering to the individual an effective amount of an immunomodulatory composition of the present disclosure. In some cases, a method of the present disclosure of treating an allergic disease comprises administering to an individual in need thereof an effective amount of an immunomodulatory composition of the present disclosure, where the immunomodulatory composition comprises an allergen. Suitable allergens are described above.

In some cases, a subject a method of the present disclosure of treating an allergic disease is effective to shift an immune response from a Th2 immune response to a Th1 immune response and/or regulate an immune response. In some cases, a subject a method of the present disclosure of treating an allergic disease is effective to decrease one or more of: a) the level of IgE in an individual; b) the level of allergen-specific IgE in an individual; c) the number of mast cells in the individual; d) the level of histamine in the individual; e) the level of a Th2-associated cytokine in the individual; f) a Th2 immune response; and g) the level of IL-4 in the individual, compared to a pre-treatment level.

In some cases, a method of the present disclosure of treating an allergic disease comprises administering an immunomodulatory composition to an individual in need thereof, and further comprising administering to the individual an effective amount of at least one additional therapeutic agent. Suitable additional therapeutic agents include, e.g., anti-histamines, steroids (e.g., corticosteroids), prostaglandin inducers, anti-inflammatory agents, leukotriene antagonists, 1L-4 muteins, soluble 1L-4 receptors, immunosuppressants (such as tolerizing peptide vaccine), anti-IL-4 antibodies, IL-4 antagonists, anti-IL-5 antibodies, soluble IL-13 receptor-Fc fusion proteins, anti-1L-9 antibodies, CCR3 antagonists, CCR5 antagonists, VLA-4 inhibitors, and downregulators of IgE. Suitable steroids include, but are not limited to, beclomethasone, fluticasone, tramcinolone, budesonide, corticosteroids and budesonide.

Methods of Treating Cancer

The present disclosure provides methods of treating cancer in an individual, the method comprising administering to the individual an effective amount of an immunomodulatory composition of the present disclosure. In some cases, a method of the present disclosure for treating cancer involves treating cancer located in a tissue, treating cancer located an organ, or treating a metastatically spread cancer. In some cases, a method of the present disclosure of treating cancer comprises administering to an individual in need thereof an effective amount of an immunomodulatory composition of the present disclosure, where the immunomodulatory composition comprises an tumor-associated antigen. Suitable tumor-associated antigens are described above.

In some cases, a method of the present disclosure of treating cancer is suitable for treating a cancer selected from leukemia, acute leukemia, acute lymphocytic leukemia, acute myelocytic leukemia, myeloblastic, promyelocytic, myelomonocytic, monocytic, erythroleukemia, chronic leukemia, chronic myelocytic, (granulocytic) leukemia, chronic lymphocytic leukemia, Polycythemia vera, lymphoma, Hodgkin's disease, non-Hodgkin's disease, Multiple myeloma, Waldenstrom's macroglobulinemia, Heavy chain disease, solid tumors, sarcomas and carcinomas, fibrosarcoma, myxosarcoma, liposarcoma, chondrosarcoma, osteogenic sarcoma, neuroblastoma sarcoma, chordoma, angiosarcoma, endotheliosarcoma, lymphangiosarcoma, lymphangioendotheliosarcoma, synovioma, mesothelioma, Ewing's tumor, brain tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, reproductive tract cancer, colorectal cancer, vulvar cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, keratoacanthoma, and neuroblastomaretinoblastoma, Kaposi sarcoma, cutaneous lymphoma and metastases.

In some cases, a subject a method of the present disclosure of treating a cancer is effective to reduce the number of cancer cells in an individual by at least about 25%, at least about 50%, at least about 75%, or at least about 99% compared to a pre-treatment number of cancer cells, or to an extent that the cancer cannot be detected in the individual (e.g., in a biological sample obtained from the individual).

In some cases, a subject a method of the present disclosure of treating a cancer is effective to increase survival and inhibit tumor growth in an individual. For example, in some cases, a subject a method of the present disclosure of treating a cancer is effective to increase survival by at least about 5%, at least about 10%, at least about 20%, at least about 25%, or more than 25%, compared to survival in the absence of treatment with a method of the present disclosure.

In some cases, a method of the present disclosure of treating a cancer comprises administering an immunomodulatory composition to an individual in need thereof, and further comprising administering to the individual an effective amount of a least one additional therapeutic agent, e.g., a cancer chemotherapeutic agent.

Chemotherapeutic agents are compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (Vinca) alkaloids, hypoxic agents, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatin, gemcitabine, cyclocytidine, guanazole, inosine glycodialdehyde, EICAR, ribavirin, tiazofurin, defroxamine and pyrazoloimidazole.

Suitable natural products and their derivatives, (e.g., *vinca* alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, camptothecin etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; antivascular flavonoids; and the like. Other agents include minerals, nutrients, vitamins, supplements, anti-oxidants, and anti-inflammatory treatments and modalities.

Other anti-proliferative cytotoxic agents are navelbene, CPT-11, anastrazole, letrazole, capecitabine, reloxafine, cyclophosphamide, folic acid, retinoic acid, ifosamide, and droloxafine. Other suitable anti-proliferative agents include siRNA, interfering RNA (RNAi), and anti-sense RNA.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation; therefore, compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Biological response modifiers suitable for use in connection with the methods of the present disclosure include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) interferon-α.; (7) interferon-γ; (8) colony-stimulating factors; (9) inhibitors of angiogenesis; (10) antagonists of tumor necrosis factor; and (11) BRAF inhibitors.

In some cases, a method of the present disclosure of treating a cancer comprises administering an immunomodulatory composition to an individual in need thereof, and further comprising administering to the individual an effective amount of at least one additional therapeutic agent, e.g., a monoclonal antibody directed against cancer antigens, where suitable monoclonal antibodies include, but are not limited to, trastuzumab (Herceptin), bevacizumab (Avastin™), rituximab (Rituxan), Oregovomab, Lambrolizumab, Ipilimumab, pertuzumab, ranibizumab (Lucentis™), Cetuximab$^R$, Camptosar$^R$, Erbitux, Brevarex, Ovarex, Pentorex etc.; antibody directed against negative receptors such as PD1 and CTLA-4; antibody directed against co-stimulatory receptors e.g., CD134 and CD137; CDP-860 (anti-CD18), antibody directed against cytokines such as IL-10 and TGF-b, and the like.

In some embodiments, the one or more different therapeutic agent is selected from different categories of anticancer agents described herein.

In some cases, a method of the present disclosure of treating a cancer comprises enhancing recovery of an individual undergoing or having undergone cancer therapy e.g., chemotherapy, radiation therapy, laser therapy, therapeutic vaccine therapy, surgical resection etc. In some cases, a method of the present disclosure of treating cancer comprises, in addition to administering an immunogenic composition of the present disclosure, administering live, killed or attenuated microbial pathogens such as bacterial cells (e.g., *S. pyogenes, S. aureus*), or viruses (e.g., pox viruses, herpes viruses, measles viruses, vaccinia viruses, rotaviruses, oncolytic viruses etc.).

In some cases, a method of the present disclosure of treating a cancer comprises administering an immunomodulatory composition to an individual in need thereof, and further comprising administering to the individual an effective amount of at least one additional vaccine (e.g., BCG vaccine, measles vaccine, rotavirus vaccine etc.).

Methods of Treating an Autoimmune Disorder

The present disclosure provides methods of treating an autoimmune disorder in an individual, the method comprising administering to the individual an effective amount of an immunomodulatory composition of the present disclosure. Autoimmune conditions account for many autoimmune disorders such as rheumatoid arthritis, asthma, type 1 diabetes, systemic lupus erythrymetosus (SLE), atherosclerosis, autoimmune hepatitis, celiac disease, autoimmune hemolytic anemia, etc. By modulating innate and adaptive immune mechanisms through the immunomodulatory composition of the present disclosure, autoimmune disorders can be treated. In some cases, a method of the present disclosure of treating an autoimmune disorder comprises administering to an individual in need thereof an effective amount of an immunomodulatory composition of the present disclosure, where the immunomodulatory composition comprises an autoantigen. Suitable autoantigens are described above.

In some cases, a subject a method of the present disclosure of treating an autoimmune disorder is effective to reduce the number and/or activity of self-reactive T cells in an individual by at least about 25%, at least about 50%, at least about 75%, or at least about 99% compared to a pre-treatment number and/or activity of self-reactive T cells, or to an extent that self-reactive T cells cannot be detected in the individual (e.g., in a biological sample obtained from the individual).

In some cases, a subject a method of the present disclosure of treating an autoimmune disorder is effective to reduce the level of autoantibodies in an individual by at least about 25%, at least about 50%, at least about 75%, or at least about 99% compared to a pre-treatment level of autoantibodies, or to an extent that autoantibodies cannot be detected in the individual (e.g., in a biological sample obtained from the individual).

In some cases, a method of the present disclosure of treating an autoimmune disorder comprises administering an immunomodulatory composition to an individual in need thereof, and further comprising administering to the individual an effective amount of a least one additional therapeutic agent. Examples of therapeutic agents that can be used to treat autoimmune disorders include, but are not limited to, anti-inflammatory agents; immunosuppressive agents (e.g., corticosteroids (e.g., prednisone, cortisol, methylprednisolone, etc.)), cyclosporin A); cytotoxic agents (e.g., 6-mercaptopurine, azathioprine, methotrexate, alkylating agents); danazol; colchisine; levamisole; and the like.

Methods of Treating Diseases Comprising an Immune Dysregulation

The present disclosure provides methods of modulating and/or regulating an immune dysfunction in an individual, the method comprising administering to the individual an effective amount of an immunomodulatory composition of the present disclosure. Immune dysfunction conditions account for many diseases such as rheumatoid arthritis, diabetes, psoriasis, systemic lupus erythematosus, graft-versus-host disease (GVHD), colitis, Crohn's disease, Alopecia areata, asthma, allergic rhinitis, conjunctivitis, transplant rejection, Hashimoto's thyroiditis, inflammatory bowel diseases, cardiovascular diseases, obesity, wound healing, burn recovery, aging, etc. By modulating innate and adaptive immune mechanisms through the immunomodulatory composition of the present disclosure, immune dysfunction disorders can be prevented and/or treated.

In some cases, a method of the present disclosure of treating an immune dysfunction disorder comprises administering an immunomodulatory composition to an individual in need thereof, and further comprising administering to the individual an effective amount of at least one additional therapeutic agent.

In some cases, the method comprising administering to an individual in need thereof an effective amount of an immunomodulatory composition of the present disclosure in a vaccine including an antigen that will modulate the dysfunctional immune response to a disease related antigen.

Methods of Treating Neurological Disorders

The present disclosure provides methods of modulating and/or regulating an inflammatory response, the method comprising administering to an individual in need thereof an effective amount of an immunomodulatory composition of the present disclosure. Inflammatory conditions account for many neurological disorders such as Alzheimer's, schizophrenia, multiple sclerosis, Parkinson's disease, autism, Amyotrophic Lateral Sclerosis (ALS), Cerebral malaria disorders etc. By modulating innate and adaptive immune mechanisms through the immunomodulatory composition of the present disclosure, neurological disorders can be treated.

In some cases, a method of the present disclosure of treating a neurological disorder comprises administering an immunomodulatory composition to an individual in need thereof, and further comprising administering to the individual an effective amount of at least one additional therapeutic agent.

In some cases, the method comprising administering to an individual in need thereof an effective amount of an immunomodulatory composition of the present disclosure in a vaccine including an antigen that will elicit an immune response to a disease related protein such as the amyloid plaques characteristics of Alzheimer or Creutzfeldt-Jacob disease (CJD).

Methods of Preventing or Treating Immunosuppression and Infections Following Stroke and Other Traumatic Brain Injuries The present disclosure provides methods of preventing or limiting infections following strokes and other brain injuries comprising administering an immunomodulatory composition of the present disclosure to an individual in need thereof. Various forms of brain trauma, including stroke, lead to long-term systemic immune suppression, resulting in higher infection and mortality rates. Further, hepatic invarant NKT cells have been shown to be important to ameliorarte systemic immunosuppression. The present disclosure represents a strategy to prevent systemic immunosuppression and infections in these patients through activation of NK, NKT and other immune cells.

In some cases, a method of the present disclosure of treating a stroke or brain trauma disorder comprises administering an immunomodulatory composition to an individual in need thereof, and further comprising administering to the individual an effective amount of at least one additional therapeutic agent.

Methods of Treating Addiction with Addictive Substances

The present disclosure provides methods of inducing antibody responses against addictive substances such as such as nicotine, cocaine, heroin, etc. The methods generally involve administering to an individual in need thereof an effective amount of an immunomodulatory composition of the present disclosure. In some cases, a method of the present disclosure of inducing an immune response to an addictive substance comprises administering to an individual in need thereof an effective amount of an immunomodulatory composition of the present disclosure, where the immunomodulatory composition comprises the addictive substance (e.g., nicotine, cocaine, heroin, etc.). The intent is to immunize patients with the vaccine comprising of the immunomodulatory composition of the disclosure as a part of the vaccination; if the patient uses cocaine after vaccination, the antibody will inhibit the reinforcing activity of cocaine and decrease the likelihood of continued addiction.

In some cases, a method of the present disclosure of treating an addiction comprises administering an immunomodulatory composition to an individual in need thereof, and further comprising administering to the individual an effective amount of at least one additional therapeutic agent.

Methods of Enhancing the Effectiveness of an Existing Vaccine

The present disclosure provides methods of enhancing and/or regulating an immune response to an existing vaccine, the method comprising administering to an individual in need thereof an effective amount of an immunomodulatory composition of the present disclosure. In some cases, a method of the present disclosure may allow reducing the dose of a vaccine, modulating the route and scheduling of a vaccine, and increasing protection in individuals with impaired immune responses. In some cases, a method of the present disclosure of enhancing and/or regulating an immune response to a vaccine comprises administering to an individual in need thereof an effective amount of an immunomodulatory composition of the present disclosure, where the immunomodulatory composition comprises an existing vaccine. Some non-limiting suitable vaccines are BCG, HBV vaccine Fenderix, Hepatitis A vaccine, Influenza vaccines (trivalent and tetravalent vaccines, Flumist, Nasovac), Rotavirus vaccine (Rota Teq, Rotarix), polio vaccine (trivalent, bivalent, monovalent vaccines), Diphtheria-tetanus vaccine, *S. typhi* (Vivotif, Ty21A), *S. pneumoneae* vaccine, *E. coli* vaccine, Pertussis vaccine, HPV vaccine Gardisil, measles vaccine, MMR vaccine, Meningococcal vaccine, *Vibrio cholerae* (Orochol), cholera (Dukoral) and other known vaccines.

Methods of Enhancing the Efficacy and/or Reducing the Toxicity of a Therapeutic Treatment The present disclosure also provides methods for enhancing the efficacy and/or reducing the toxicity of a therapeutic treatment, preferably treatment with an anti-infective or antiviral drug, anticancer, other immunostimulatory/modulatory compounds or a surgical treatment by administering an effective amount of an immunomodulatory composition of the present disclosure to an individual, cells or tissues preferably the amount needed to elicit and/or regulate an immune response.

In some cases, a method of the present disclosure of enhancing efficacy and reducing toxicity comprises administering an immunomodulatory composition to an individual in need thereof, and further comprising administering to the individual an effective amount of at least one additional therapeutic agent.

Methods of Increasing Antigen Presentation on Dendritic Cells

The present disclosure provides a method of enhancing antigen presentation on a dendritic cell, the method comprising: a) contacting dendritic cells (DCs) obtained from an individual with a composition comprising: i) heat-killed *Caulobacter crescentus*; and ii) an antigen. The DCs are contacted with the HKCC and the antigen is in vitro. Contacting DCs with the antigen and the HKCC enhances antigen presentation of the antigen on the DCs, thereby generating a population of antigen-presenting DCs. In some cases, the antigen can be contacted with DCs using methods such as diffusion, electroporation, active transport, liposome fusion, phagocytosis, sonication etc. In some cases, the method further comprises administering the antigen-presenting DCs to the individual from whom the DCs were obtained. In some cases, the method further comprises administering the antigen-presenting DCs combined with antibodies, chemotherapeutic agents, or cytokines to the individual from whom the DCs were obtained. Administering an antigen-presenting DC to an individual can treat a disease in the individual.

Suitable antigens are described above. In some cases, a composition comprising HKCC and antigen is contacted with DCs; and the HKCC-antigen-DC mixture is incubated for a period of time of from about 30 minutes to about 48 hours, thereby generating a population of antigen-presenting DCs. A subject method can increase the proportion of DCs that are antigen-presenting DCs by at least about 25%, at least about 50%, at least about 75%, at least about 2-fold, at least about 5-fold, at least about 10-fold, at least about 25-fold, at least about 50-fold, at least about 100-fold, or more than 100-fold, compared to the proportion of DCs in the starting population that are antigen-presenting DCs.

Methods of Activating Effector Immune Cells

The present disclosure provides a method of activating effector lymphocytes such as NK, NKT, T cells, and B cells, the method comprising: a) contacting effector cells (NK, NKT, T cells, and/or B cells) obtained from an individual with a composition comprising: i) heat-killed *Caulobacter crescentus*; and/or ii) an antigen in the presence or absence of antigen presenting cells. Contacting effector lymphocytes and the HKCC enhances their activation, thereby generating a population of activated effector lymphocytes. In some cases, naïve T cells can be primed in vitro/ex vivo against a given antigen, comprising contacting naïve T cells with professional antigen presenting cells, an antigen and immunomodulatory composition of the present disclosure under suitable conditions and sufficient time to activate the naïve T cells. In some cases, the method further comprises administering the activated effector lymphocytes to the individual from whom the cells were obtained, to prevent and/or treat a disease in a host. In some cases, the method further comprises administering the activated effector lymphocytes combined with antibodies, chemotherapeutic agents, or cytokines to the individual from whom the cells were obtained, to prevent and/or treat a disease in a host.

Methods of Treating an Infection with an Intracellular Pathogen

The present disclosure provides methods of preventing and/or treating infections with intracellular pathogens (e.g., viruses, mycobacteria, bacteria, parasites etc.) in an individual, the method comprising administering to the individual an effective amount of an immunomodulatory composition of the present disclosure.

In some cases, a method of the present disclosure of treating an intracellular pathogen comprises administering to an individual in need thereof, and further comprising administering to the individual an effective amount of at least one additional therapeutic agent.

Methods of Enhancing Immune Responses in Cell Culture for Research, Diagnosis and/or Therapeutic Purposes The present disclosure provides a method of activating various TLRs, NLRs, DCs and/or effector lymphocytes such as NK, NKT, T and B cells, the method comprising: a) contacting effector cells (NK, NKT, T and B cells) obtained from an individual with a composition comprising: i) heat-killed *Caulobacter crescentus*; and/or ii) an antigen in the presence or absence of antigen presenting cells. Contacting effector lymphocytes and the HKCC enhances their activation, thereby generating a population of activated effector lymphocytes. In some cases, the method comprises of diagnosing a disease state by identifying and expanding specific antigen reactive T cells and/or B cells. In some cases, the method comprises of identifying and expanding specific antigen reactive T cells and/or B cells in vitro for research purposes. In some cases the method comprises of administering the activated effector lymphocytes to the individual from whom the cells were obtained, to prevent and/or treat a disease in a host. In some cases, the method comprises of activating TLRs or NLRs for research and/or diagnostic purposes.

Methods of Inducing Proliferation and Differentiation of Stem Cells

The present disclosure provides a method of inducing proliferation, differentiation of stem cells and restoration of homeostasis in an individual, the method comprising administering to the individual an effective amount of an immunomodulatory composition of the present disclosure. The present disclosure provides a method of modifying stem cells, the method comprising contacting the stem cells with a composition comprising heat-killed *Caulobacter crescentus*, wherein said contacting generates a population of expanded and/or differentiated stem cells.

The present disclosure also provides a method of inducing proliferation and/or differentiation of stem cells, the method comprising contacting stem cells obtained from an individual with an immunomodulatory composition of the present disclosure, e.g., an immunomodulatory composition comprising heat-killed *Caulobacter crescentus*. Contacting the stem cells with the HKCC leads to their proliferation and differentiation, thereby generating a population of expanded and differentiated cells. The population of expanded and differentiated cells can then be administered to the individual from whom the stem cells were obtained.

In some embodiments, a method of the present disclosure of inducing proliferation and/or differentiation of stem cells comprises: a) obtaining stem cells from an individual; b) contacting the stem cells in vitro with HKCC, thereby generating a population of expanded and differentiated cells; and c) administering the population of expanded and differentiated cells to the individual.

In some embodiments, a method of the present disclosure of inducing proliferation and/or differentiation of stem cells in an individual comprises administering to the individual an effective amount of an immunomodulatory composition of the present disclosure. In some cases, an effective amount of an immunomodulatory composition of the present disclosure is an amount that is effective, when administered in a single dose or in multiple doses, to induce proliferation and/or differentiation of hematpoietic stem cells, and restore homeostasis. For example, in some cases, an effective amount of an immunomodulatory composition of the present disclosure is an amount that is effective, when administered in a single dose or in multiple doses, to induce proliferation and/or differentiation of hematpoietic stem cells, and restore homeostasis in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the individual in the absence of treatment with the immunomodulatory composition.

Formulations, Dosages, and Routes of Administration

An immunomodulatory composition of the present disclosure can include one or more pharmaceutically acceptable excipients; and can be formulated in any of a variety of ways, that may depend, e.g., on the route of administration. Pharmaceutically acceptable excipients are known to those skilled in the art, and have been amply described in a variety of publications, including, for example, A. Gennaro (1995) "Remington: The Science and Practice of Pharmacy", 19th edition, Lippincott, Williams, & Wilkins. Suitable excipient vehicles include, for example, water, saline, dextrose, glycerol, ethanol, inert proteins, hydrophillic polymers, amino acids, fatty acids, surfactants, non-ionic surfactants, carbohydrates, dextrins, polyols, chelating agents, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985; Remington: The Science and Practice of Pharmacy, A. R. Gennaro, (2000) Lippincott, Williams & Wilkins.

An immunomodulatory composition can be incorporated into a variety of formulations for therapeutic administration. More particularly, an immunomodulatory composition can be formulated into pharmaceutical compositions by combination with appropriate, pharmaceutically acceptable carriers, salts, preservatives, buffering agents, or diluents, and may be formulated into preparations in solid, semi-solid, liquid, lyophilized or gaseous forms, such as tablets, capsules, powders, granules, ointments, solutions, suppositories, injections, skin patches, inhalants and aerosols. In other embodiments, the formulation comprises a colloidal delivery system that includes e.g., liposomes, nano-particles, nano-emulsions, nano capsules, microspheres and polymers.

In pharmaceutical dosage forms, an immunomodulatory composition may be administered alone or in appropriate association, as well as in combination, with other pharmaceutically active compounds. An immunomodulatory composition, an antigen, adjuvant and/or therapeutic drug can be administered concurrently, simultaneously, sequentially or at different times, at the same or different sites, and via different routes. The following methods and excipients are merely exemplary and are in no way limiting.

For oral preparations, an immunomodulatory composition can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An immunomodulatory composition can be formulated into liquid preparations for administration by dissolving, suspending or emulsifying the composition in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

An immunomodulatory composition can be utilized in aerosol formulation to be administered via inhalation. The immunomodulatory compositions of the present disclosure can be formulated into pressurized acceptable propellants such as dichlorodifluoromethane, propane, nitrogen and the like.

Furthermore, an immunomodulatory composition can be made into suppositories by mixing with a variety of bases such as emulsifying bases or water-soluble bases. An immunomodulatory composition can be administered rectally via a suppository. The suppository can include vehicles such as cocoa butter, carbowaxes and polyethylene glycols, which melt at body temperature, yet are solidified at room temperature.

An immunomodulatory composition of the present disclosure can also be administered in the form of liposomes or liposomal polymeric gels. Liposomes can be given by a variety of routes, oral, nasal, parenteral, trans-dermal, inhalation etc. As is known in the art, liposomes are derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to an immunomodulatory composition of the present disclosure, one or more of a stabilizer, a preservative, an excipients, and the like. Exemplary lipids are the phospholipids and the phosphatidylcholines (lecithins), both natural and synthetic. Liposomes can be in a size range of from less than 100 nm to several microns. Methods to form liposomes are known in the art. for example, Prescott, Ed., *Methods in Cell Biology*, Volume XIV, Academic Press, New York, N.Y. (1976), p. 33 et seq.

Unit dosage forms for oral or rectal administration such as syrups, elixirs, emulsions, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise an immunomodulatory composition as a solution in sterile water, normal saline or another pharmaceutically acceptable carrier.

A subject immunomodulatory composition can be formulated for topical administration. Topical administration includes administration to the skin or mucosa, including surfaces of the lung eye, nose, and ear. Suitable topical preparations include, e.g., skin patch preparation, transdermal patch preparation, micro arrays, cream, lotion, gel preparations, powder, ointment, paste, intranasal drops or gels.

Ointments are semi-solid preparations, which are typically based on petrolatum or other petroleum derivatives. Suitable ointments include oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (WIO) emulsions or oil-in-water (OIW) emulsions, and include, for example, cetyl alcohol, glyceryl monostearate, lanolin and stearic acid. Exemplary water-soluble ointment bases are prepared from polyethylene glycols of varying molecular weight.

Lotions are preparations to be applied to the skin surface without friction, and are typically liquid or semi liquid preparations in which solid particles, including the active agent, are present in a water or alcohol base. Lotions are usually suspensions of solids, and preferably, for the present purpose, comprise a liquid oily emulsion of the oil-in-water type. Lotions can be used for treating large body areas, because of the ease of applying a more fluid composition. Lotions may contain suspending agents to produce better dispersions as well as compounds useful for localizing and holding the active agent in contact with the skin, e.g., methyl cellulose, sodium carboxymethyl-cellulose, or the like. An example of a lotion formulation for use in conjunction with the present invention contains propylene glycol mixed with a hydrophilic petrolatum such as that which may be obtained under the trademark Aquaphor® from Beiersdorf, Inc. (Norwalk, Coon.).

Suitable creams can be viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil so phase in volume, and generally contains a humectant. The emulsifier in a cream formulation, as explained in Remington, supra, is generally a nonionic, anionic, cationic or amphoteric surfactant.

Gels formulations can be used. Gels are semisolid, suspension-/type systems. Single-phase gels contain organic macromolecules distributed substantially uniformly throughout the carrier liquid, which can be aqueous, but may also contain an alcohol and, optionally, an oil.

A topical formulation may also be delivered to the skin using conventional "transdermal"-type patches, wherein the agent (immunomodulatory composition) is contained within a laminated structure that serves as a delivery device to be affixed to the skin. In such a structure, the immunomodulatory composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysioxanes, polyisobutylenes, polyacrylates, polyurethanes, and the like. The particular polymeric adhesive selected will depend on the particular immunomodulatory composition, vehicle, etc., i.e., the adhesive must be compatible with all components of the drug-containing composition. In an alternative embodiment, the immunomodulatory composition-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

The term "unit dosage form," as used herein, refers to physically discrete units suitable as unitary dosages for human and animal subjects, each unit containing a predetermined quantity of an active agent (e.g., HKCC; antigen; etc.) calculated in an amount sufficient to produce the desired effect in association with a pharmaceutically acceptable diluent, carrier or vehicle. The specifications for the active agents depend on the particular compound employed and the effect to be achieved, and the pharmacodynamics associated with each compound in the host.

Other modes of administration will also find use. For instance, an immunomodulatory composition can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), or about 1% to about 2%.

Intranasal formulations will usually include vehicles that neither cause irritation to the nasal mucosa nor significantly disturb ciliary function. Diluents such as water, aqueous saline or other known substances can be employed. The nasal formulations may also contain preservatives such as, but not limited to, chlorobutanol and benzalkonium chloride. A surfactant may be present to enhance absorption of the subject proteins by the nasal mucosa.

An immunomodulatory composition can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985; Remington: The Science and Practice of Pharmacy, A. R. Gennaro, (2000) Lippincott, Williams & Wilkins. The composition or formulation to be administered will, in any event, contain a quantity of an active agent (e.g., HKCC; antigen; etc.) adequate to achieve the desired state in the subject being treated.

The pharmaceutically acceptable excipients, such as vehicles, adjuvants, salts, carriers or diluents, are readily available to the public. Moreover, pharmaceutically acceptable auxiliary substances, such as pH adjusting and buffering agents, tonicity adjusting agents, stabilizers, emulsifying agents, surfactants, preservatives, amino acids, fatty acids, wetting agents and the like, are readily available to the public.

Oral Formulations

In some embodiments, an immunomodulatory composition is formulated for oral delivery to an individual in need of such an immunomodulatory composition.

For oral delivery, a subject formulation comprising an immunomodulatory composition will in some embodiments include an enteric-soluble coating material. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™, and shellac.

Suitable oral formulations also include an immunomodulatory composition, formulated with any of the following: microgranules (see, e.g., U.S. Pat. No. 6,458,398); biodegradable macromers (see, e.g., U.S. Pat. No. 6,703,037); biodegradable hydrogels (see, e.g., Graham and McNeill (1989) Biomaterials 5:27-36); biodegradable particulate vectors (see, e.g., U.S. Pat. No. 5,736,371); bioabsorbable lactone polymers (see, e.g., U.S. Pat. No. 5,631,015); slow release protein polymers (see, e.g., U.S. Pat. No. 6,699,504; Pelias Technologies, Inc.); a poly(lactide-co-glycolide/polyethylene glycol block copolymer (see, e.g., U.S. Pat. No. 6,630,155; Atrix Laboratories, Inc.); a composition comprising a biocompatible polymer and particles of metal cation-stabilized agent dispersed within the polymer (see, e.g., U.S. Pat. No. 6,379,701; Alkermes Controlled Therapeutics, Inc.); and microspheres (see, e.g., U.S. Pat. No. 6,303,148; Octoplus, B.V.).

Suitable oral formulations also include an immunomodulatory composition formulated with any of the following: a carrier such as Emisphere® (Emisphere Technologies, Inc.); TIMERx, a hydrophilic matrix combining xanthan and locust bean gums which, in the presence of dextrose, form a strong binder gel in water (Penwest); Geminex™ (Penwest); Procise™ (GlaxoSmithKline); SAVIT™ (Mistral Pharma Inc.); RingCap™ (Alza Corp.); Smartrix® (Smartrix Technologies, Inc.); SQZgel™ (MacroMed, Inc.); Geomatrix™ (Skye Pharma, Inc.); Oros® Tri-layer (Alza Corporation); and the like.

Also suitable for use are formulations such as those described in U.S. Pat. No. 6,296,842 (Alkermes Controlled Therapeutics, Inc.); U.S. Pat. No. 6,187,330 (Scion, Inc.); and the like.

Also suitable for use herein are formulations comprising an intestinal absorption enhancing agent. Suitable intestinal absorption enhancers include, but are not limited to, calcium chelators (e.g., citrate, ethylenediamine tetracetic acid); surfactants (e.g., sodium dodecyl sulfate, bile salts, palmitoylcarnitine, and sodium salts of fatty acids); toxins (e.g., zonula occludens toxin); and the like.

Suitable oral formulations also include an immunomodulatory composition, formulated as a food supplement (e.g. nutraceuticals, yogurt, bars, drinks, prebiotics, symbiotics, paraprobiotics) etc.

Controlled Release Formulations

In some embodiments, an immunomodulatory composition is formulated in a controlled release formulation.

Controlled release can be taken to mean any one of a number of extended release dosage forms. The following terms may be considered to be substantially equivalent to controlled release, for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, *Extended-Release Dosage Forms,* 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technologies: Methods, Theory and Applications,* 1980 (CRC Press, Inc.).

There are a number of controlled release drug formulations that are developed for oral administration. These include, but are not limited to, osmotic pressure-controlled gastrointestinal delivery systems; hydrodynamic pressure-controlled gastrointestinal delivery systems;

membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems may be found in Yie W. Chien, *Novel Drug Delivery Systems,* 1992 (Marcel Dekker, Inc.). Some of these formulations will now be discussed in more detail.

Enteric coatings are applied to tablets to prevent the release of active agents in the stomach either to reduce the risk of unpleasant side effects or to maintain the stability of the drug which might otherwise be subject to degradation of expose to the gastric environment. Most polymers that are used for this purpose are polyacids that function by virtue or the fact that their solubility in aqueous medium is pH-dependent, and they require conditions with a pH higher than normally encountered in the stomach.

One exemplary type of oral controlled release structure is enteric coating of a solid or liquid dosage form. The enteric coatings are designed to disintegrate in intestinal fluid for ready absorption. Delay of absorption of the active agent that is incorporated into a formulation with an enteric coating is dependent on the rate of transfer through the gastrointestinal tract, and so the rate of gastric emptying is an important factor. Some investigators have reported that a multiple-unit type dosage form, such as granules, may be superior to a single-unit type.

Suitable enteric coating agents include, but are not limited to, hydroxypropylmethylcellulose phthalate, methacryclic acid-methacrylic acid ester copolymer, polyvinyl acetate-phthalate and cellulose acetate phthalate.

Another type of useful oral controlled release structure is a solid dispersion. A solid dispersion may be defined as a dispersion of one or more active ingredients in an inert carrier or matrix in the solid state prepared by the melting (fusion), solvent, or melting-solvent method.

Examples of carriers useful in solid dispersions include, but are not limited to, water-soluble polymers such as polyethylene glycol, polyvinylpyraolidone, and hydroxypropylmethylcellulose. Alternative carriers include phosphatidylcholine. Phosphatidylcholine is an amphoteric but water-insoluble lipid, which may improve the solubility of otherwise insoluble active agents in an amorphous state in phosphatidylcholine solid dispersions.

Other carriers include polyoxyethylene hydrogenated castor oil. An immunomodulatory composition can be included in a solid dispersion system with an enteric polymer such as hydroxypropylmethylcellulose phthalate and carboxymethylethylcellulose, and a non-enteric polymer, hydroxypropylmethylcellulose. Another solid dispersion dosage form includes incorporation of the drug of interest (e.g., an active agent) with ethyl cellulose and stearic acid in different ratios.

There are various methods commonly known for preparing solid dispersions. These include, but are not limited to, the melting method, the solvent method and the melting-solvent method.

Injectable microspheres are another controlled release dosage form. Injectable micro spheres may be prepared by non-aqueous phase separation techniques, and spray-drying techniques. Microspheres may be prepared using polylactic acid or copoly(lactic/glycolic acid).

Other controlled release technologies that may be used include, but are not limited to, SODAS (Spheroidal Oral Drug Absorption System), INDAS (Insoluble Drug Absorption System), IPDAS (Intestinal Protective Drug Absorption System), MODAS (Multiporous Oral Drug Absorption System), EFVAS (Effervescent Drug Absorption System), PRODAS (Programmable Oral Drug Absorption System), and DUREDAS (Dual Release Drug Absorption System) available from Elan Pharmaceutical Technologies. SODAS are multi particulate dosage forms utilizing controlled release beads. INDAS are a family of drug delivery technologies designed to increase the solubility of poorly soluble drugs. IPDAS are multi particulate tablet formation utilizing a combination of high density controlled release beads and an immediate release granulate. MODAS are controlled release single unit dosage forms. Each tablet consists of an inner core surrounded by a semipermeable multiparous membrane that controls the rate of drug release. EFVAS is an effervescent drug absorption system. PRODAS is a family of multi particulate formulations utilizing combinations of immediate release and controlled release mini-tablets. DUREDAS is a bilayer tablet formulation providing dual release rates within the one dosage form. Although these dosage forms are known to one of skill, certain of these dosage forms will now be discussed in more detail.

An immunomodulatory composition of the present disclosure can be incorporated into any one of the aforementioned controlled released dosage forms, or other conventional dosage forms. The amount of active agent contained in each dose can be adjusted, to meet the needs of the individual patient, and the indication. One of skill in the art and reading this disclosure will readily recognize how to adjust the level of an active agent and the release rates in a controlled release formulation, in order to optimize delivery of an active agent and its bioavailability.

Inhalational Formulations

An immunomodulatory composition of the present disclosure will in some embodiments be administered to a patient by means of a pharmaceutical delivery system for the inhalation route. The immunomodulatory composition may be formulated in a form suitable for administration by inhalation. The inhalational route of administration provides the advantage that the inhaled drug can bypass the blood-brain barrier. The pharmaceutical delivery system is one that is suitable for respiratory therapy by delivery of an active agent to mucosal linings of the bronchi. A system that depends on the power of a compressed gas to expel the immunomodulatory composition from a container can also be used. An aerosol or pressurized package can be employed for this purpose.

As used herein, the term "aerosol" is used in its conventional sense as referring to very fine liquid or solid particles carries by a propellant gas under pressure to a site of therapeutic application. When a pharmaceutical aerosol is employed, the aerosol contains the therapeutically active compound (e.g., active agent), which can be dissolved, suspended, or emulsified in a mixture of a fluid carrier and a propellant. The aerosol can be in the form of a solution, suspension, emulsion, powder, or semi-solid preparation. Aerosols can be used for administration as fine, solid particles or as liquid mists via the respiratory tract of a patient. Various types of propellants known to one of skill in the art can be utilized. Suitable propellants include, but are not limited to, hydrocarbons or other suitable gas. In the case of the pressurized aerosol, the dosage unit may be determined by providing a value to deliver a metered amount.

An immunomodulatory composition can also be formulated for delivery with a nebulizer, which is an instrument that generates very fine liquid particles of substantially uniform size in a gas. For example, a liquid containing the immunomodulatory composition is dispersed as droplets. The small droplets can be carried by a current of air through an outlet tube of the nebulizer. The resulting mist penetrates into the respiratory tract of the patient.

There are several different types of inhalation methodologies which can be employed in connection with an immunomodulatory composition of the present disclosure. An immunomodulatory composition can be formulated with low boiling point propellants. Such formulations are generally administered by conventional meter dose inhalers (MDI's). Alternatively, immunomodulatory composition can be formulated in aqueous or ethanolic solutions and delivered by conventional nebulizers. In some embodiments, such solution formulations are aerosolized using devices and systems such as disclosed within U.S. Pat. Nos. 5,497,763; 5,544,646; 5,718,222; and 5,660,166. An immunomodulatory composition can be formulated into dry powder formulations. Such formulations can be administered by simply inhaling the dry powder formulation after creating an aerosol mist of the powder. Technology for carrying such out is described within U.S. Pat. No. 5,775,320 issued Jul. 7, 1998 and U.S. Pat. No. 5,740,794 issued Apr. 21, 1998.

An immunomodulatory composition of the present disclosure will in some embodiments be formulated for vaginal delivery. A subject immunomodulatory composition for intravaginal administration can be formulated as an intravaginal bioadhesive tablet, intravaginal bioadhesive microparticle, intravaginal cream, intravaginal lotion, intravaginal foam, intravaginal ointment, intravaginal paste, intravaginal solution, or intravaginal gel.

A subject immunomodulatory composition will in some embodiments be formulated for rectal delivery. A subject formulation for intrarectal administration comprises a subject immunomodulatory composition formulated as an intrarectal bioadhesive tablet, intrarectal bioadhesive microparticle, intrarectal cream, intrarectal lotion, intrarectal foam, intrarectal ointment, intrarectal paste, intrarectal solution, or intrarectal gel. An immunomodulatory composition of the present disclosure can be formulated with agents that improve adhesion to mucosal membranes such as mucoadhesives, bioadhesives, particles, microspheres or liposomes.

A subject immunomodulatory composition can include one or more of an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, poly(ethylene glycol), sucrose or starch), a disintegrator (e.g., starch, carboxymethylcellulose, hydroxypropyl starch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol).

Tablets comprising an immunomodulatory composition may be coated with a suitable film-forming agent, e.g., hydroxypropylmethyl cellulose, hydroxypropyl cellulose or ethyl cellulose, to which a suitable excipient may optionally be added, e.g., a softener such as glycerol, propylene glycol, diethylphthalate, or glycerol triacetate; a filler such as sucrose, sorbitol, xylitol, glucose, or lactose; a colorant such as titanium hydroxide; and the like.

Dosages

The dosage of an immunomodulatory composition of the present disclosure can vary, depending on factors such as the clinical goals to be achieved, the age of the individual being treated, the physical status of the individual being treated, etc.

An immunomodulatory composition of the present disclosure can comprise HKCC in an amount of from about $10^3$ HKCC per unit dosage form to about $10^{20}$ HKCC per unit dosage form. For example, an immunomodulatory composition of the present disclosure can comprise HKCC in an amount of from about $10^3$ HKCC per unit dosage form to about $10^4$ HKCC per unit dosage form, from about $10^4$ HKCC per unit dosage form to about $10^5$ HKCC per unit dosage form, from about $10^5$ HKCC per unit dosage form to about $10^6$ HKCC per unit dosage form, from about $10^6$ HKCC per unit dosage form to about $10^7$ HKCC per ml, from about $10^8$ HKCC per unit dosage form to about $10^9$ HKCC per unit dosage form, from about $10^9$ HKCC per ml to about $10^{10}$ HKCC per unit dosage form, from about $10^{15}$ HKCC per unit dosage form to about $10^{20}$ HKCC per unit dosage form, or more than $10^{20}$ HKCC per unit dosage form.

For example, an immunomodulatory composition of the present disclosure can comprise HKCC in an amount of from about $10^3$ HKCC per nil to about $10^{20}$ HKCC per ml. For example, an immunomodulatory composition of the present disclosure can comprise HKCC in an amount of from about $10^3$ HKCC per ml to about $10^4$ HKCC per ml, from about $10^4$ HKCC per ml to about $10^5$ HKCC per ml, from about $10^5$ HKCC per ml to about $10^6$ HKCC per ml, from about $10^6$ HKCC per ml to about $0^7$ HKCC per ml, from about $10^8$ HKCC per ml to about $10^9$ HKCC per ml, from about $10^9$ HKCC per ml to about $10^{10}$ HKCC per ml, from about $10^{15}$ HKCC per ml to about $10^{20}$ HKCC per ml, or more than $10^{20}$ HKCC per ml.

An immunomodulatory composition of the present disclosure can comprise HKCC in an amount of from about $10^2$ to about $10^{20}$ colony forming units (cfu) per unit dosage form; for example, an immunomodulatory composition of the present disclosure can comprise HKCC in an amount of from about $10^2$ to about $10^3$ from about $10^3$ to about $10^5$, from about $10^5$ to about $10^7$, from about $10^7$ to about $10^9$, from about $10^9$ to about $10^{11}$, from about $10^{11}$ to about $10^{13}$, from about $10^{13}$ to about $10^{15}$, from about $10^{15}$ to about $10^{18}$, or from about $10^{18}$ to about $10^{20}$, cfu per unit dosage form. A unit dosage form can be an amount that is administered in a single dose; for example, a unit dosage form can be 0.5 ml, 1.0 ml, or other volume suitable for administration in a single dose.

An immunomodulatory composition of the present disclosure can comprise HKCC in an amount of from about $10^2$ to about $10^{20}$ cfu per ml; for example, an immunomodulatory composition of the present disclosure can comprise HKCC in an amount of from about $10^2$ to about $10^3$ from about $10^3$ to about $10^5$, from about $10^5$ to about $10^7$, from about $10^7$ to about $10^9$, from about $10^9$ to about $10^{11}$, from about $10^{11}$ to about $10^{13}$, from about $10^{13}$ to about $10^{15}$, from about $10^{15}$ to about $10^{18}$, or from about $10^{18}$ to about $10^{20}$, cfu per ml.

In some embodiments, multiple doses of an immunomodulatory composition of the present disclosure are administered. The frequency of administration of an immunomodulatory composition of the present disclosure can vary depending on any of a variety of factors, e.g., severity of the symptoms, etc. For example, in some embodiments, an immunomodulatory composition of the present disclosure is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of an immunomodulatory composition of the present disclosure, e.g., the period of time over which an immunomodulatory composition of the present disclosure is administered, can vary, depending on any of a variety of factors, e.g., patient response, etc. For example, an immunomodulatory composition of the present disclosure can be administered over a period of time ranging from about one hour to one day, from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Where an immunomodulatory composition comprises an antigen, the dosage of antigen is selected as an amount which is effective and modulates an immune response without significant adverse side effects. Such amount can vary, depending, e.g., upon which specific antigen is employed, the route of administration, etc. Where an immunomodulatory composition comprises an antigen, the dosage of antigen can range from 1 ng per unit dosage form to about 100 mg per unit dosage form, e.g., from about 1 ng to about 25 ng, from about 25 ng to about 50 ng, from about 50 ng to about 100 ng, from about 100 ng to about 250 ng, from about 250 ng to about 500 ng, from about 500 ng to about 750 ng, from about 750 ng to about 1 µg, from about 1 µg to about 25 µg, from about 25 µg to about 50 µg, from about 50 µg to about 100 µg, from about 100 µg to about 250 µg, from about 250 µg to about 500 µg, from about 500 µg to about 750 µg, from about 750 µg to about 1 mg, from about 1 mg to about 25 mg, from about 25 mg to about 50 mg, or from about 50 mg to about 100 mg, per unit dosage form.

Routes of Administration

An immunomodulatory composition of the present disclosure is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, subcutaneous, intradermal, intranodal, percutaneous, transdermal, intratumoral, topical application, intravenous, intravesicular, rectal, nasal, oral and other enteral and parenteral routes of administration. Routes of administration may be combined, if desired, or adjusted depending upon the agent and/or the desired effect. The composition can be administered in a single dose or in multiple doses.

An immunomodulatory composition of the present disclosure can be administered to a host using any available conventional methods and routes suitable for delivery of conventional drugs, including systemic or localized routes. In general, routes of administration contemplated include, but are not necessarily limited to, enteral, parenteral, or inhalational routes.

Parenteral routes of administration other than inhalation administration include, but are not necessarily limited to, topical, transdermal, subcutaneous, intramuscular, intradermal, intralymphatic, intraorbital, intracapsular, intraspinal, intrasternal, intracranial, intravesicular, and intravenous routes, i.e., any route of administration other than through the alimentary canal. Parenteral administration can be carried to effect systemic or local delivery of the immunomodulatory composition. Where systemic delivery is desired, administration typically involves invasive or systemically absorbed topical or mucosal administration of pharmaceutical preparations.

An immunomodulatory composition of the present disclosure can also be delivered to the subject by enteral administration. Enteral routes of administration include, but are not necessarily limited to, oral and rectal (e.g., using a suppository) delivery.

An immunomodulatory composition of the present disclosure can also be delivered to the subject via a mucosal route of delivery. Mucosal routes of delivery include nasal, buccal, sublingual, vaginal, ocular, and rectal routes of administration.

In certain embodiments, an immunomodulatory composition of the present disclosure is administered to a subject via a combination of different routes in the order indicated below:

i. systemic, mucosal;
  ii. systemic, systemic, mucosal, mucosal;
  iii. systemic, mucosal, systemic;
  iv. mucosal, mucosal, systemic, systemic;
  v. mucosal, systemic, systemic;
  vi. mucosal, systemic, mucosal, for example.

When an immunomodulatory composition of the present disclosure is administered systemically or mucosally more than once, the two or more systemic or mucosal administrations may be by the same systemic (for example, two intramuscular injections) or mucosal route (two IN/SL administrations) or different (for example, one intramuscular injection and one intravenous injection; one IN administration and one SL administration).

An immunomodulatory composition of the present disclosure is administered to an individual using any available method, delivery or device such as vaccine patches, needles, microneedles (hollow or solid), drop, syrup, tablets, capsules, pipette, dose-spray pumps, nasal dropper, inhalation devices, liquid or dry powder, suspensions or solutions, spray devices, Accuspray™, thermoresponsive gels, jet injectors, Nasovak™, Bespak™, ointment, lotions, suppositories, gels etc.

Individuals Suitable for Treatment

Individuals suitable for treatment using a method of the present disclosure include humans; non-human mammals; fish; and birds. In any of the above embodiments discussed below, the individual being treated using a subject method can be a non-human mammal such as livestock (e.g., pigs, sheep, goats, tattles, equine, caprine, ovine, bovine, etc.); a mammalian pet (e.g., cats; dogs; horses; etc.); a bird such as chicken, hens, turkeys, geese, quail, ducks etc.; or other animals such as fish.

In any of the above embodiments discussed below, the individual being treated using a subject method is a human of from about one month to about 6 months, from about 6 months to about 1 year, or from about 1 year to about 5 years of age. In any of the above embodiments discussed below, the individual being treated using a subject method is a human of from about 5 years to about 12 years, from about 13 years to about 18 years, or from about 18 years to about 25 years of age. In any of the above embodiments discussed below, the individual being treated using a subject method is a human of from about 25 years to about 50 years, from about 50 years to about 75 years of age, or older than 75 years of age. In any of the above embodiments discussed below, the individual being treated using a subject method is a human who is immunocompromised.

In some embodiments, the individual has a viral disease, or is at risk of contracting a viral disease. In some cases, the disease is a viral disease selected from the group consisting of, but not limited to, viral disease caused by hepatitis B, hepatitis C, rotavirus, human immunodeficiency virus, human T-cell lymphotropic virus, DNA viruses such as parvoviruses, adeno viruses, papovaviruses (e.g., papilloma virus, polyoma viruses, and SV40), herpes viruses (e.g., herpes simplex type I (HSV-I), herpes simplex type II (HSV-II), and Epstein-Barr virus), poxviruses (e.g., variola (smallpox) and vaccinia virus); and RNA viruses, such as retroviruses [e.g. human immunodeficiency virus type I (HIV-I), human immunodeficiency virus type II (HIV-II), human T-cell lymphotropic virus type I (HTLV-I), human T-cell lymphotropic virus type II (HTLV-II)], orthomyxoviruses (e.g., influenza viruses), paramyxoviruses (e.g., measles virus, mumps virus, respiratory syncytial virus), rhabdoviruses (e.g., rabies virus), Sendai virus, picornaviruses (e.g., poliomyelitis virus, coxsackieviruses, rhinoviruses), reoviruses (e.g., rotavirus, colorado tick fever virus), togaviruses (e.g., rubella virus (German measles), Japanese encephalitis virus and Semliki forest virus), arboviruses, calciviruses (e.g., hepatitis E virus), flaviviruses (e.g., yellow fever virus, dengue virus), coronaviruses, filoviruses (e.g., Ebola and Marburg viruses) and Bunyaviruses (e.g., Hanta virus, California encephalitis virus).

In some embodiments, the individual has a bacterial infection, or is a risk of contracting a bacterial infection. In some embodiments, the individual has a mycobacterial infection, or is at risk of contracting a mycobacterial infection. In some embodiments, the individual is infected with, or is at risk of becoming infected with, a pathogenic bacterium. Pathogenic bacteria include, e.g., Gram positive bacteria, Gram negative bacteria, mycobacteria, etc. Non-limiting examples of pathogenic bacteria include Mycobacteria (e.g., *M. tuberculosis, M. avium* complex), *Streptococcus, Staphylococcus, Pseudomonas, Salmonella, Neisseria*, and *Listeria*. In some cases, the bacteria is *Neisseria gonorrhea, M. tuberculosis, M. leprae, Listeria monocytogenes, Streptococcus pneumoniae, S. pyogenes, S. agalactiae, S. viridans, S. faecalis,* or *S. bovis*. Other examples of pathogenic bacteria contemplated include, but are not limited to, Gram positive bacteria (e.g., *Listeria, Bacillus* such as *Bacillus anthracis, Erysipelothrix* species), Gram negative bacteria (e.g., *Bartonella, Brucella, Campylobacter, Enterobacter, Escherichia, Francisella, Hemophilus, Klebsiella, Morganella, Proteus, Providencia, Pseudomonas, Salmonella, Serratia, Shigella, Vibrio,* and *Yersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, *Pneumococcus* species, *Staphylococcus* species, *Neisseria* species.

In some embodiments, the individual has a neoplastic disease, where a neoplastic disease includes, but is not limited to, leukemia, acute leukemia, acute lymphocytic leukemia, acute myelocytic leukemia, myeloblastic, promyelocytic, myelomonocytic, monocytic, erythroleukemia, chronic leukemia, chronic myelocytic, (granulocytic) leukemia, chronic lymphocytic leukemia, Polycythemia vera, lymphoma, Hodgkin's disease, non-Hodgkin's disease, Multiple myeloma, Waldenstrom's macroglobulinemia, Heavy chain disease, solid tumors, sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, and neuroblastomaretinoblastoma.

In some cases, the individual has, or is at risk of contracting, a parasitic disease. Parasitic diseases that can be treated or prevented by the methods of the present disclosure include, but are not limited to, amebiasis, malaria, leishmania, coccidia, giardiasis, cryptosporidiosis, toxoplasmosis, trypanosomiasis, schistosomiasis, and filariasis.

In some cases, the individual has, or is at risk of contracting, a fungal disease. Fungal diseases that can be treated or prevented by the methods of the present disclosure include, but are not limited to *Candida* spp. including *C. albicans, Aspergillus* spp., *Cryptococcus* spp. including *C. neoformans, Blastomyces* sp., *Pneumocytes* spp., or *Coccidioides* spp.

In some cases, the individual has, or is at risk of contracting, a worm infection, a fluke infection, etc. Also encompassed are infections by various worms, such as but not limited to ascariasis, ancylostomiasis, trichuriasis, strongyloidiasis, toxoccariasis, trichinosis, onchocerciasis filaria, and dirofilariasis. Also encompassed are infections by various flukes, such as but not limited to schistosomiasis, paragonimiasis, and clonorchiasis.

In some embodiments, the individual has an autoimmune disorder or an immune dysfunction, or is at risk of developing an autoimmune disorder or an immune dysfunction. In some cases, the disease is selected from the group consisting of, but not limited to, allergy, rheumatoid arthritis, asthma, diabetes, systemic lupus erythrymetosus (SLE), Grave's disease, atherosclerosis, multiple sclerosis, schizophrenia, Alzheimer's, depression, hypopituitarism, neurodegenerative disorders, cardiovascular diseases, obesity etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); i.n., intranasal(ly); i.v., intravenous(ly); s.c., subcutaneous(ly); and the like.

EXAMPLES

Materials and Methods

The following materials and methods were used in the Examples described below.

Materials

AIM V serum-free media was obtained from the Life Technologies (Burlington, Ontario, Canada). Nylon wool was purchased from Robbins Scientific (Sunnyvale, Calif.), made into 10 ml columns, and autoclaved to make it sterile. Ficoll-Paque was obtained from Pharmacia Biotech, (Quebec, Canada). Anti-CD3 (OKT3) antibody was used as purified antibody obtained from culture supernatant of clones purchased from the American Type Culture Collection (ATCC) (Rockville, Md.). PHA was obtained from Sigma Chemical Company. Cytokine kits were purchased from eBioscience (San Diego, Calif.). Poly 1:C, monophosphoryl lipid A (MPL) were purchased from Sigma Chemical company. Ribavirin was purchased from TRC (Toronto, Canada). Telaprevir was bought from LGM Pharma (TN, USA). Peginterferon was obtained University of Alberta Hospital pharmacy. Wild-type, lipopolysaccharide (LPS)-negative, S-layer negative and recombinant H5-HA *Caulobacter crescentus* were grown at room temperature (22-27° C.) in the incubator, and heat-killed at 60-80° C. for 30-60 minutes. HEK 293 cells expressing human TLRs or NLRs were purchased from Invivogen (San Diego, Calif.).

Methods

PBMCs and DCs

Peripheral blood mononuclear cells (PBMCs) were obtained from normal human donors using Ficoll-Paque. T cells were purified using nylon wool columns. Briefly, 0.75 g of nylon wool was loaded on a 10 ml syringe. The columns were pre-incubated with media for 25 min. and $10^8$ PBMCs were loaded on the top. After a 45-min. incubation at 37° C., non-adherent T cells were eluted with warm AIM V media (37° C.). To obtain dendritic cells (DCs), adherent PBMCs were cultured with recombinant GM-CSF and IL-4 for 5-6 days in RPMI media, using procedures well established in the literature.

Proliferation Assay

PBMCs or enriched T cells were cultured in AIM V media in 96-well flat bottom plate at $2\times10^5$ cells per well in the presence or absence of mitogens (OKT3, 1 µg/ml; or phytohemagglutinin (PHA), 5 µg/ml; or allogeneic irradiated PBMCs $2\times10^5$/well). Test compounds were added at various concentrations (from 0.00001-100 µg/ml). Stock solutions of test compounds were made at 10 mg/ml in dimethylsulfoxide (DMSO) and equivalent amount of DMSO was added to stimulated cultures to obtain the media control. The plates were incubated for 4-5 days at 37° C. in humidified 5% $CO_2$, pulsed for final 12-18 hours with 1 µCi/well $^3$H-thymidine in 50 µl AIM V media. The contents of the well were harvested onto glass fiber filters using a multiple automated sample harvester, and the $^3$H-thymidine incorporation was determined by liquid scintillation counter and represented as counts per minute (CPM) incorporated/well. Each group was set up in 3-5 replicate wells and the data was calculated with mean CPMs of the replicates. Percent control was calculated as 100×CPM with the compound/CPM without the compound.

Release of Cytokines

Human PBMCs as purified above were cultured in 24 well plates in AIM V media at $2\times10^6$/well/2 ml with or without 0.5 µg phytohemagglutinin (PHA)/well. Test compounds were all added at 10 µg/ml, with an equivalent amount of DMSO added in control wells. The plates were incubated for 3 days at 37° C. in humidified 5% $CO_2$ incubator and culture supernatant (1.6 ml) was collected for cytokine analysis by enzyme-linked immunosorbent assay (ELISA). As the negative control, non-stimulated cell supernatant was used. The supernatant was tested for cytokines IL-2, IL-10, IL-17A, IL-22, IL-12, IL-6, IFN-7, IFN-α TNF-α, and granulocyte-macrophage colony stimulating factor (GM-CSF) using R & D Systems (Minneapolis, Minn.) or eBioscience ELISA kits using manufacturer's protocol. Each assay was done in duplicate. In the initial tests, the positive and negative control wells (without test compounds) were tested in titrating concentrations to determine the dilution of the sups that lies well within the detection range of standard cytokine concentrations. This was performed with each experiment independently and allowed the experiment to be conducted at a dilution range where the standard curve was a straight line and the secreted cytokines in experimental groups could be accurately quantitated. Final cytokine concentration was then determined taking the dilution factor into consideration. Percent of control amount of cytokines was calculated as 100×pg/ml cytokine in the presence of test compounds/pg/ml cytokine in the absence of test compounds.

Activation of Human PBMCs and In Vitro Antiviral Activity

Human PBMCs ($2\times10^6$/ml) from individual normal healthy donors were incubated with HKCC ($10^5$-$10^7$/ml) in AIM V media for 24 h at 37° C. in an incubator, followed by collection of supernatants. The supernatant was then used at various concentrations (300, 450 or 500 µl for total 1 ml of media) to determine anti-HCV activity as follows. Briefly, $1\times10^5$ HCV 1a replicon containing Huh-7 cells per well were plated in 24-well plates in DMEM media supplemented with fetal bovine serum (10%) and selection antibiotic G418. On the next day, replicon cells were incubated at 37° C. with various volumes of supernatants, indicated drugs, with or without telaprevir or ribavirin. The cells were incubated for five days. After the 5-day incubation period, cells were used for RNA determination. Total cellular RNA was extracted using an RNAeasy-96 kit (Qiagen, Valencia, Calif.), cDNA was synthesized using iScript cDNA synthesis kit (BioRAD, CA) and the copy number of HCV RNA was determined using a quantitative polymerase chain reaction (PCR) (Q-PCR) assay using probes (BioRAD, CA). β-Actin was used to normalize the HCV RNA copy numbers. The primers used for PCR assays were: HCV UTR F: 5'-CTG TCT TCA CGC AGA AAG CG-3' (SEQ ID NO:1); HCV UTR R: 5'-CAC TCG CAA GCA CCC TAT CA-3' (SEQ ID NO:2); β-actin F: 5'-CGA TGC AGA AGG AGA TCA CTG-3' (SEQ ID NO:3); β-actin R: 5'-CGA TCC ACA CGG AGT ACT TG-3' (SEQ ID NO:4). The % inhibition or HCV RNA copy number/$10^6$ cells shown are the averages of 3 replicates and the standard deviations were within 10%. Similarly, the supernatants collected with HKCC treatment of PBMCs can be effective against the HCV 1b genotype and multiple genotypes (2a, 2b, 3a, 4a, 5a etc.) of HCV.

Inhibition of *Mycobacterium*

To determine the intracellular inhibition of Mtb and *M. avium*, human monocytic cell line (THP-1) was infected with *M. avium* or Mtb H37Ra using published procedures, followed by two treatments (on days 0 and 4) with supernatants (50%) collected from human PBMCs treated for 24 hrs with HKCC or PBS in 24 well plates. Supernatants collected from three different donor PBMCs stimulated with HKCC were tested as donors #1, #2 and #3. In controls clarithromycin, rifampicin or HKCC were added directly to infected THP-1 cells. Five days after second treatment, THP-1 were collected, lysed and plated on 7H11 agar plates to determine bacterial CFUs.

Adjuvants

*Caulobacter crescentus* was grown at 25-30° C. in liquid PYE medium (0.2% peptone, 0.1% yeast extract supplemented with 1 ml/L of 20% $MgSO_4$ and 10% $CaCl_2$) containing 2 µg/ml chloramphenicol. The bacterial cell concentration was determined as $3.0 \times 10^9$ CFU/ml/1 optical density (O.D.) at 600 nm. The purity of bacterial cultures was examined by phase-contrast microscopy and by plating the bacterial cultures on PYE containing solid agar plates. Wild-type *Caulobacter crescentus* was suspended in PBS and heat killed at 80° C. for 30-60 minutes in a water bath, and is referred to as HKCC.

Monophosphoryl lipid A (MPL) was purchased from Sigma (USA). An aqueous formulation containing MPL at a 4:1 molar ratio was prepared as per manufacturer's instructions, aliquoted and stored at 4° C. Polyarginine hydrochloride was purchased from Sigma (USA). IFA was purchased from Pierce Biotech (USA).

Antigens/Peptides

Seasonal trivalent influenza vaccine Vaxigrip$^R$ (2009-2010 season) containing viral antigens from A/California/7/2009 (H1N1), A/Perth/16/2009 (H3N2) and B/Brisbane/60/2008 was purchased from Sanofi Pasteur (Canada). Recombinant HBV core was purchased from United States Biologicals (MA, USA). Recombinant HCV proteins (NS3, NS3+NS4) were from Chiron Corp. The peptides and lipopeptides were custom synthesized by a Genscript Inc (NJ, USA). The HCV NS3 peptides (1127-46, 1187-1206, 1248-71, 1367-86, 1487-1506, 1507-26, 1547-66, 1607-26, 1621-40, 1637-57), Influenza M2e peptide (SLLTEVETPIRNEWGCRCNDSSD; SEQ ID NO:5), Mtb Ag85B peptides (68-88, 93-112, 126-142, 143-167, 199-218, 240-251, 257-273) and malaria Spf66 peptide were used unmodified or modified at carboxyl terminal by the addition of a lysine-palmitoyl or lysine-dipalmitoyl group. All peptides/lipopeptides were prepared at 10 mg/ml as stock solutions in DMSO and stored frozen. The stocks were diluted with phosphate-buffered saline (PBS) as required. Recombinant adenovector containing HCV-NS3 were prepared according to published procedures.

Mice 6-8 Weeks old C57BL/6 or BALB/c, male or female mice were purchased from Charles River Breeding Laboratories. All animal experimental protocols used in this study were approved by the University of Alberta Animal Care and Use Committee for Health Sciences, and conducted in accordance with the guidelines of the University of Alberta, Edmonton, Canada.

Viruses, Bacteria, and Tumor Cell Lines

For the surrogate vaccinia-HCV model, the Western Reserve (WR) strain of vaccinia virus (VV) ($1 \times 10^7$ pfu/mouse) containing HCV NS3-NS5 region of the HCV BK strain (genotype 1b) [rVV-(NS3-NS5)] was used to challenge female C57Bl/6 mice intraperitoneally. The virus was grown in BHK-cells. The titer of virus was determined by plaque assay on BHK-cells and was stored at −80 C.° until use.

In the influenza infection models, the mouse adapted influenza strain of H1N1 (A/PR8/34) was used intranasally to challenge mice. The viruses were grown in MDCK cells. The virus was quantified using a cellular ELISA protocol detecting the intracellular influenza nucleoprotein (NP). Briefly, MDCK cells were plated at $1 \times 10^4$/well in 96 well tissue culture plate and allowed to adhere for 24 hours. Biological sample or stock of the influenza virus prepared was added on MDCK monolayer and incubated for 2 hrs. At this time, plates were washed and cultured for further 36-72 hrs, with the last 8 hrs in the presence of Brefeldin A. The cells were then fixed using formaldehyde and treated with anti-NP antibody and saponin solution. The intracellular bound anti-NP antibody was detected by using Goat anti mouse-biotin labeled antibody which was then detected by Sreptavidin.

In the tuberculosis model, *Mycobacterium tuberculosis* (Mtb) H37Ra ($0.5 \times 10^6$ cfu/mouse) was used intravenously to infect BALB/c female mice. The mice were housed in a specific pathogen-free facility.

For the tumor challenge experiments EL-4 (a C57Bl/6 mouse derived T cell lymphoma cell line) and B16 (a C57Bl/6 mouse derived melanoma cell line) (ATCC) were used.

Immunization(s)/Treatments of Mice and Sample Collections

The mice were administered once, twice or thrice with a mixture of peptide/lipopeptide/protein antigens with heat-killed (80° C. for 30-60 min.) *Caulobacter crescentus* (HKCC) in PBS using routes as stated in different figures.

In prophylactic experiments, HKCC was administered with or without antigens to mice intranasally, subcutaneously or orally as described in detail in each figure.

In therapeutic experiments, pre-challenged mice were administered with HKCC with or without antigens intranasally, subcutaneously, intramuscularly, or orally as described in detail in each figure.

The amount of antigens and adjuvant are described in figure legends. Untreated mice were given equivalent volume of PBS or saline corresponding to the experimental group. After euthanization of mice at specific times, blood, spleen, inguinal lymph nodes, nasal washes, lung washes etc. were collected.

Isolation of Splenic T Cells

At specific times after immunization, the mice were euthanized to obtain splenocytes. The spleens were pooled from 3-5 mice and ground to a single cell suspension and filtered through a Falcon 100 µm nylon cell strainer. After centrifugation, the cell pellet was resuspended in 2 ml of sterile distilled water and briefly vortexed. Immediately, 2×PBS were added and after a brief vortex the volume was made to 25 ml with 1×PBS. The tube was centrifuged and the cell pellet was resuspended in 10 ml of complete RPMI. It was again filtered through a Falcon 100 µm nylon cell strainer and centrifuged. The cell pellet was resuspended in 2 ml of media and passed through an equilibrated nylon wool column. The column was washed after 45 min of incubation at 37° C. and the flow through contained the splenic T cells. These T cells were taken for the experiment (~90% CD3+ T cells).

T Cell Proliferation Assay

Proliferative responses of splenic T cells were measured in triplicate cultures in 96-well flat-bottomed microliter plates. A total of $4\times10^5$ spleen T cells from immunized mice and $4\times10^5$ antigen-presenting cells (APCs) (spleen cells from control syngeneic mice irradiated with 18 Gy) were mixed with different concentrations (0.5-10 μg/mL) of either recombinant NS3 protein (c33c, aa 1192-1457 NS3), truncated polyprotein (c200, NS3-NS4, aa 1192-1931) or control superoxide dismutase (SOD) were cultured in RPMI medium (with 10% fetal bovine serum (FBS)) at 37° C. (5% $CO_2$) for 4 days. In experiments with different exemplary antigens, relative peptide or proteins were used at concentrations described in each figure.

The cells were pulsed with 0.5 μCi/well [$^3$H]-thymidine (Amersham) for 12-18 h and harvested on filter papers (Perkin Elmer). The levels of [$^3$H]-thymidine incorporated into the DNA of proliferating cells were counted in a Microbeta Trilux liquid scintillation counter (Perkin Elmer). Proliferation is represented as the mean cpm±SE (standard error) of triplicate cultures.

ELISpot Assay for GrB Producing CD8+ T Cells

Enzyme-linked immunosorbent spot (ELISPOT) assay kits were obtained from R&D Systems and manufacturer's instructions were followed for the ELISpot assay. Briefly, 96-well nitrocellulose plates were coated with a capture anti-mouse Granzyme B (GrB) antibody overnight at 2-8° C., followed by washing the plates for 2-3 times with PBS. After blocking with the blocking buffer at room temp for 2 hrs, the buffer was aspirated and mouse splenocytes activated for 3 days as described in T cell proliferation assay in the presence or absence of antigens were added at $1-5\times10^5$/well in RPMI media. The plates were incubated at 37° C. for overnight, followed by washing with PBS for 4 times. Plates were then added with detection antibody and incubated overnight at 2-8° C., followed by the addition of Streptavidin-alkaline phosphatase (AP) and incubation for 2 hrs at room temperature. Color was developed by adding chromogen 5-bromo-4-chloro-1H-idol-3-yl/nitro blue tetrazolium (BCIP/NBT) for 5-15 minutes. Plates were rinsed with distilled water and dried before enumerating the number of spots/well using an ELISPOT reader Biosys.

Evaluation of Antibody Responses

The levels of antibodies (IgG, IgG1, IgG2a, IgA) in serum, lung and nasal washes were determined using enzyme-linked immunosorbent assays (ELISAs). Briefly, 96-well nitrocellulose (Nunc) plates were coated with relevant antigen (such as OVA, influenza, Hepatitis B surface antigen (HBsAg), HBV core antigen, whole cell lysate from EL-4 or B16) and incubated overnight at 4° C. The plates were blocked with PBS containing normal mouse serum, followed by incubating with the experimental samples at different dilutions for 2 hrs at room temperature. After washing the plates for 4 times, Anti mouse Ig isotype antibodies conjugated with Alkaline phosphatase (AP) were added, followed by incubation for 2 hrs. After washing the plates, PNPP substrate was added and color development was read on Fluostar ELISA reader at 405 nm wavelength. All reagents for antibody detection were obtained from Southern Biotech (Birmingham, Ala.).

Flow Cytometry Analysis of Surface Markers, Intracellular Granzyme B and Foxp3.

A total of $5\times10^5$ cells from immunized mice were taken for intracellular and extracellular staining with multicolor fluorescently-labeled mAbs (concentrations according to manufacturer's instructions). The cells were incubated with Fc mouse-serum (Sigma) to prevent non-specific binding and washed with fluorescence-activated cell sorter (FACS)-buffer (2% fetal bovine serum in 1× phosphate-buffered saline (PBS). After incubation for 30 minutes with anti-mouse CD3e-FITC, CD4-PECy-5, CD25-PE-Cy7, CD8a-APC-Cy7, anti-PD-1-PerCP eFluore 710, anti-CD49b-Alexafluor-700 (for BALB/c and C57bl/6 mice) or anti-NK1.1 (for C57bl/6 mice), anti-CD11c, anti-CD19, anti-CD11b, anti-CD40, anti-CD69, anti-CD25 etc. (eBioscience) for extracellular markers at 4° C., the cells were washed twice and fixed in fixative solution (1% paraformaldehyde in FACS-buffer) for 5 minutes. After washing twice, the cells were incubated with cold permeabilization buffer (FACS-buffer+0.3% Saponin (Sigma)+5% normal human serum in PBS) for 5 minutes followed by addition of anti-GrB-PE (Caltag Laboratories, Burlingame, Calif.) and anti-Foxp3-APC (eBioscience) and further incubated for 30 minutes at 4° C. The cells were washed once with FACS-buffer containing 1 Saponin and fixed. They were read in FACS-Canto and analyzed using FACS-DIVA software (Becton Dickinson, Mountain View, Calif.). Each marker was gated based on its respective isotype-matched control monoclonal antibodies. Similar staining methodology was used with human DCs to determine various activation markers (CD11c, CD80, CD86, DEC-205 etc.) (eBioscience) in flow cytometry experiments.

Mouse Cytokine ELISA

Cytokines secreted in the supernatant of proliferating co-cultures, or mouse serum samples were measured using sandwich ELISA kits following the manufacturer's protocol (eBioscience, CA, USA) for the presence of IL-10, IL-12, GM-CSF, IL-17A, IFN-γ, IFN-α, IFN-β, IL-2, TGF-β and IL-4. A dilution of 1:2 to 1:50 was used for the samples with the standards ranging from 5 to 2000 pg/ml. Finally the ELISA plates were read and the concentrations were calculated with an automated ELISA plate reader (Fluostar Optima, BMG Labtech).

Quantitation of Vaccinia Virus Expressing HCV Genes in Ovaries by Plaque Assay

Mice were sacrificed 5 days post infection. Pairs of ovaries from individual mouse were harvested and homogenized in 1 ml DMEM. They were treated with 3 repeats of thaw freeze cycle, sonicated and centrifuged at 3500 rpm for 15 min, the supernatant were stored at −80 C.°, until used for plaque assay or virus nucleic acid isolation. To determine virus titer, 10-fold dilutions of supernatant were plated onto BHK-21 cells in 6 well plates. After 90 min of incubation at 37 C.° in 5% $CO_2$ and then 2.5% DMEM was applied. The plates were incubated for 48 hours at 37 C.° in 5% $CO_2$. The cells were then stained with 0.1% crystal violet in 20% ethanol and the number of plaques was enumerated.

CFU Assay to Determine Mtb Load in Various Organs

Three weeks after H37Ra infection, mice were euthanized and lung, liver and spleen were removed aseptically and individually homogenized. CFU counts per 10% organ were determined on 7H11 selective agar plates purchased from BD Biosciences. The plates were incubated at 37° C. in ambient air for up to 3-4 weeks prior to counting the colonies.

Results

The following examples are intended to illustrate rather than limit the scope of the invention.

The adjuvant and immunotherapeutic effects of HKCC were tested with various types of vaccines in different models and indications via systemic and mucosal routes as follows.

Figure 1:
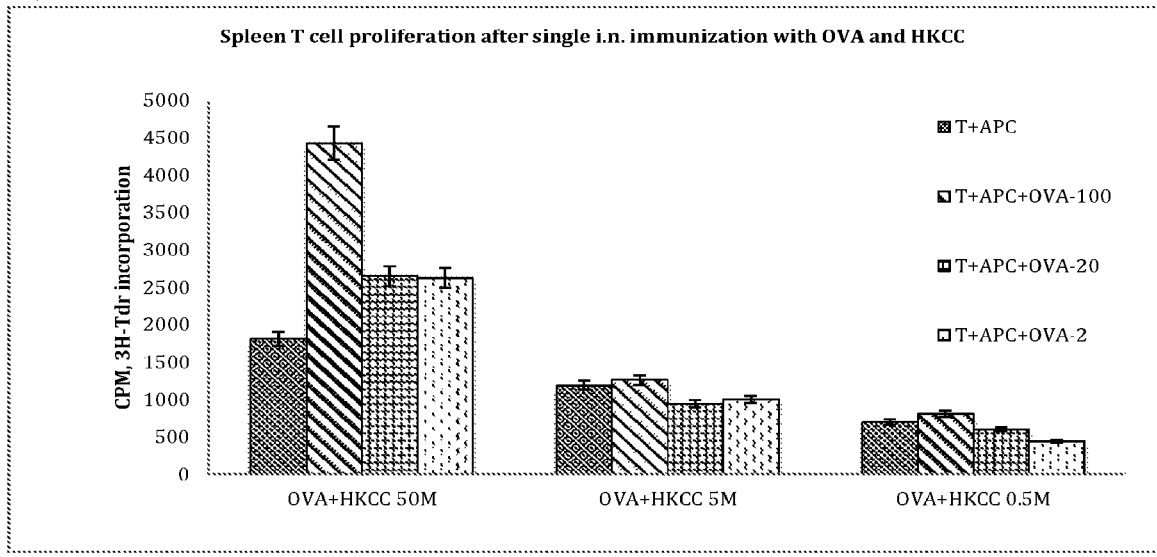
FIG. 1 depicts the effect of heat-killed *Caulobacter crescentus* (HKCC) as a mucosal adjuvant to induce T cell responses against OVA. HKCC at $50 \times 10^6$ CFU/mouse induces higher antigen specific T cell responses following single intranasal immunization of C57/b16 male mice with a mixture of OVA antigen (50 μg/mouse) than lower doses (0.5-$5 \times 10^6$ CFU/mouse). Mice were euthanized 2 wks after immunization. Values are the mean of triplicates with ±SD.

Example 1: Heat-Killed *Caulobacier crescenius* (HKCC) as a Mucosal Adjuvant The effect of HKCC on an immune response against a whole protein antigen was investigated using ovalbumin (OVA) upon intranasal immunization. C57/b16 male mice were immunized once intranasally with a mixture of OVA antigen (50 µg/mouse) and HKCC at three different doses (0.5-50×$10^6$ colony forming units (CFU)/mouse, indicated as 0.5M, 5 M and 50 M, respectively). The mice were euthanized 8 days after single immunization and OVA specific T cell proliferation response was examined using 3H-Tdr incorporation assay (FIG. 1).

The results obtained indicate that HKCC induces T cell responses against OVA upon single intranasal (mucosal) administration. Dose response study suggests that HKCC at 50×$10^6$ CFU/mouse induces higher antigen specific T cell responses following single intranasal immunization as compared to the lower doses (0.5-5×$10^6$ CFU/mouse) (FIG. 1).

Example 2: Effect of Live *Caulobacter crescentus* (CC) and HKCC on Antigen-Specific Immune Responses Against Ovalbumin (OVA)

The effect of live and heat-killed CC for the induction of OVA-specific cellular and humoral immune responses in vivo was determined. Groups of five C57/b16 mice were immunized by the subcutaneous (s.c.) route at the base of the tail twice on days 0 and 14, or once with live CC or HKCC at 50×$10^6$ CFU/mouse and OVA antigen (20 µg/mouse) in 100 µl total volume/mouse. Mice were euthanized 8 days after one immunization or 2 weeks (wks) after two immunizations. T cell proliferative responses against OVA antigen were determined from T cells obtained from spleen and lymph nodes (FIG. 2A, 2B, 2D). Antigen specific GrB producing CTLs were quantified (ELISPOT assay) using splenocytes (FIG. 2C). Serum antibody (IgG and IgG1) responses was measured using ELISA (FIG. 2E).

Example 3: HKCC as an Adjuvant for Therapeutic HBV Vaccine to Induce Cellular and Humoral Immune Responses C57/b16 male mice were immunized twice (at 14 days intervals) with a mixture of recombinant HBV core antigen (5 µg/mouse) and HKCC (50×$10^6$ CFU/mouse) by intranasal route. Mice were euthanized 1 week and 3 weeks after second immunization. Spleen, blood, lung washes were collected and used to determine cellular and humoral immune responses against HBV core antigen. Splenocytes obtained from mice immunized with HBV core and HKCC showed much higher T cell proliferation, IFN-gamma and IL-12 production and Granzyme B (GrB)-producing CTLs compared to HBV core alone immunization (FIG. 3A-F). In addition, systemic IgG and IgG2a, as well as mucosal (lung) IgG and IgA against HBV core antigen were induced to greater extent in mice immunized with HBV core plus HKCC compared to HBV core antigen only both in the short and the long-term (1 vs. 3 week post 2nd immunization) (FIG. 3G-L).

These results demonstrate that HKCC induced strong and long-lasting antigen specific T cell (CD4+, CD8+) and antibody responses against the conserved HBV core antigen in an animal model as shown in FIG. 3A-L. These studies suggest that HKCC can adequately induce both cellular and humoral immune responses against HBV antigen and could be used as therapeutic vaccine regimen. Also, these results suggest that a needle-free nasal immunization with an antigen using HKCC as an adjuvant could be an effective approach of vaccination.

Example 4: HKCC Exhibits Potent Adjuvant Activity Enhancing HCV Derived NS3 Specific T Cell Responses In the case of HCV infection, failure to generate and maintain an effective cellular immune response in the acute phase is likely responsible for the high rate of chronicity. A vaccine that can induce efficient T cell responses against conserved antigens of HCV or an immunotherapeutic approach that can induce broad and effective anti-HCV immunity would be beneficial for the prevention and/or treatment of HCV infections.

Figure 4:
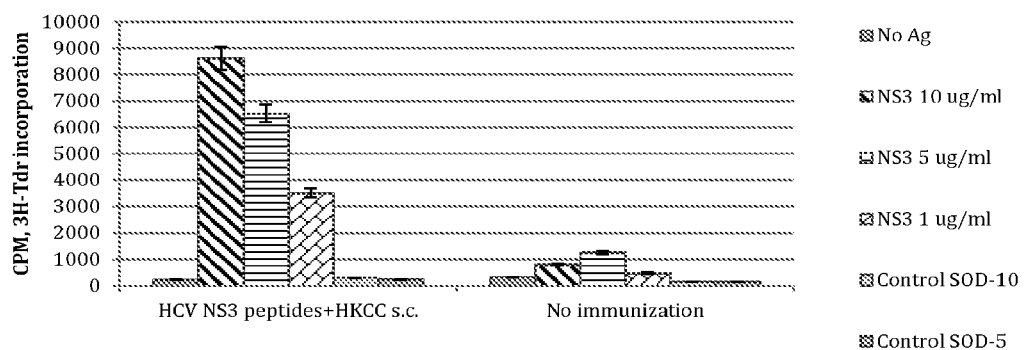
FIG. 4 illustrates that HKCC exhibits potent adjuvant activity enhancing HCV derived NS3 specific T cell responses. C57Bl/6 female mice were immunized twice (at 10 day intervals) with a mixture of 10 lipopeptides (NS3 1248-71, 1621-40, 1127-46, 1187-1206, 1367-86, 1487-1506, 1507-26, 1547-66, 1607-26, 1637-57, 2.5 μg each peptide/mouse) and HKCC ($50 \times 10^6$ CFU/mouse) s.c. The mice were euthanized 15 days after second immunization. HCV antigen specific T cell responses of spleen from immunized vs. unimmunized mice are shown. Values are the mean of triplicates with ±SD.
Figure 11G:
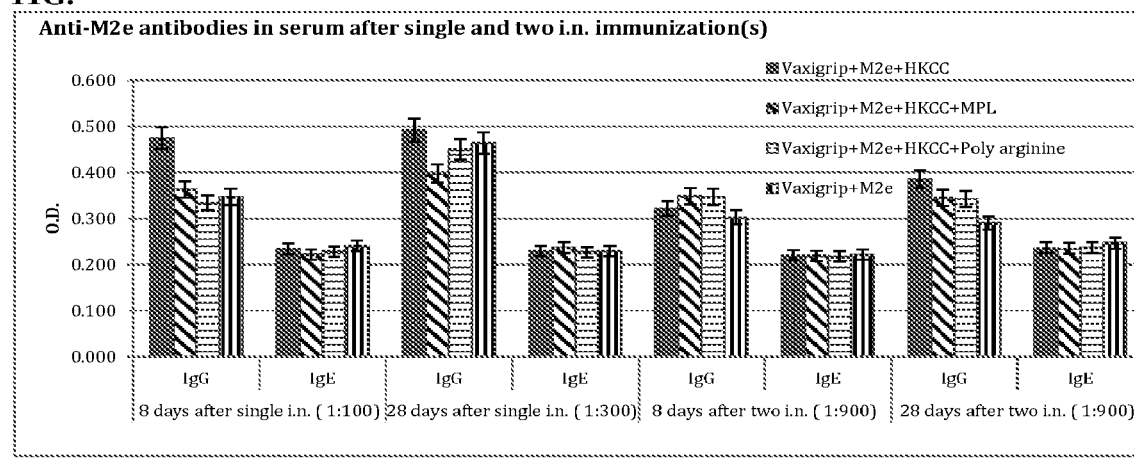

In order to determine if HKCC could be used as an adjuvant for HCV vaccine, C57Bl/6 female mice were immunized subcutaneously twice (at 10 day intervals) with a mixture of 10 different lipopeptides (NS3 1248-71, 1621-40, 1127-46, 1187-1206, 1367-86, 1487-1506, 1507-26, 1547-66, 1607-26, 1637-57, 2.5 µg each peptide/mouse) and HKCC (50×$10^6$ CFU/mouse). The mice were euthanized 15 days after second immunization. The spleens of immunized mice were isolated and examined for antigen specific proliferative responses against recombinant NS3 antigen or control antigen SOD (FIG. 4). The results demonstrated that HKCC adjuvant greatly enhances HCV antigen specific T cells when compared to unimmunized mice. Mice immunized with NS3 peptides only, did not show NS3 specific T cell responses and were comparable to unimmunized groups. These results also suggest the applicability of HKCC adjuvant for peptide-specific subunit vaccines.

Example 5: HKCC as an Adjuvant for Subunit Vaccine for Tuberculosis: Reduction of Mycobacterial Load in Lungs, Liver and Spleen In order to determine if HKCC could be used as an adjuvant to induce mycobacterial antigen specific immune responses which could lead to anti-mycobacterial immunity and reduction in bacterial load, groups of five mice were immunized twice subcutaneously at 12-day intervals with a mixture of 7 monolipopeptides derived from Ag 85B (68-88, 93-112, 126-142, 143-167, 199-218, 240-251, 257-273, 5 µg each peptide/mouse) and HKCC (50×$10^6$ CFU/mouse). The immunized mice were challenged intravenously with 0.5× $10^6$ cfu/mouse Mth H37Ra six weeks after second immunization. Infected mice were euthanized three weeks after Mtb challenge. Lungs, liver and spleen were collected from individual mice and used for CFU assay to determine bacterial load in these organs (FIG. 5A-C). The CFU data obtained from five individual mice demonstrated that pre-immunization with Mtb Ag85B derived peptides along with HKCC partially protects mice from getting Mtb infection and/or leads to much lower bacterial loads in lungs, liver and spleen, compared to unimmunized mice (FIG. 5A-C). Mice immunized with Ag85B peptides only, did not show a reduction in the bacterial loads compared to unimmunized groups (data not shown). These results demonstrated that HKCC as an adjuvant to a subunit vaccine can provide efficient protection against bacterial infection and/or reduces bacterial load upon infection (FIG. 5A-C). Further, HKCC represents a novel potent immunostimulator in providing systemic protection against lung, liver and spleen infection from Mtb upon immunization with peptide-based antigens of a mycobacterial protein. Similarly, HKCC can provide strong protection when combined with other immunostimulatory proteins produced and/or secreted by the TB bacterium.

Example 6: HKCC as an Adjuvant for Tumor Vaccine: Reduction of EL-4 Tumors after Single s.c. Immunization Whole tumor cell vaccines are interesting candidates for cancer vaccines as they could provide protection mediated by multiple antigens' specific T cells and B cells as opposed to single antigen or subunit based vaccines. However, these strategies are limited due to insufficient immunity induced in response to whole tumor cells. In order to examine if HKCC can bolster immune responses to whole tumor cells, groups of five C57Bl6 mice were immunized once subcutaneously with a mixture of irradiated EL-4 cells ($1\times10^6$/mouse) and HKCC ($50\times10^6$ CFU/mouse). The immunized mice were challenged with $0.25\times10^6$ EL-4 cells/mouse in 100 µl PBS subcutaneously in the lower left flank eight days after the immunization. Tumor growth was measured for 28 days after challenge using digital calipers in two perpendicular directions, and mice were humanely euthanized. Tumor area were calculated as length×width (in mm). The results showed that administration of irradiated tumor cells with adjuvant HKCC generated significant protective effect against a solid tumor in vaccinated mice with robust systemic tumor specific T cell and antibody responses (FIG. 6A-D). In addition, HKCC as an adjuvant in a whole irradiated tumor cell vaccine inhibits tumor progression (FIG. 6A, B).

Example 7: HKCC as an Adjuvant for Lung Cancer Vaccine: Reduction in Lung Metastases after Single s.c. Immunization To examine if HKCC can bolster immune responses to whole tumor cells in a metastatic lung cancer model, groups of five C57Bl6 mice were immunized once subcutaneously with a mixture of irradiated B16 cells ($1\times10^6$/mouse) and HKCC ($50\times10^6$ CFU/mouse). The immunized mice were challenged with $0.4\times10^6$ B16 cells/mouse in 50 µl PBS intravenously in the tail vein eight days after immunization. Mice were humanely euthanized 12 days after tumor challenge. The lungs and serum were collected. Lung nodules were examined by pictures taken and weight of lungs were determined (FIG. 7A, B). Further, sera were tested for the presence of IgG specific against B16 cell lysate (FIG. 7C). The results obtained demonstrated that HKCC adjuvanted whole irradiated tumor cell vaccine (whole irradiated tumor cell in a formulation with HKCC as an adjuvant) inhibits metastatic lung cancer progression and induce tumor specific antibody responses (FIG. 7A-C).

Example 8: Antitumor Activity of HKCC Against B16 Melanoma Lung Metastasis after Subcutaneous Treatments In a cancer or tumor bearing individuals, usually the presence of specific tumor antigens lead to priming of antigen specific immune responses, however, they are not effective in providing protection from tumor progression due to several mechanisms regulating and/or inhibiting these immune responses. To determine if treatment with HKCC as an immunomodulator could provide reduction in cancer progression, groups of four C57Bl6 mice were challenged with $0.4\times10^6$ B16 cells/mouse in 100 µl PBS intravenously in the tail vein. Starting from day 3 post challenge with B16 melanoma cancer cells, HKCC ($50\times10^6$ cfu/mouse) was administered twice subcutaneously at one week interval. Three days after the last treatment, mice were euthanized. Lungs and serum were collected. The results obtained demonstrate that immunotherapy with HKCC alone leads to marked reduction in metastatic lung cancer progression (FIG. 8A), normalization of lung weights (FIG. 8B), and induction of tumor specific systemic IgG responses (FIG. 8C). No metastasis of B16 cells was seen in other organs. In addition, B cells, DCs, NK and NKT cells were activated and/or increased significantly in spleens and lungs in treated mice compared to untreated B16 tumor bearing mice (data not shown). Further to increasing effective immunity in tumor bearing mice, HKCC therapy also modulated the percentage of Tregs in both lungs and spleens. Therefore, HKCC therapy results in marked inhibition of lung cancer in a highly aggressive metastatic mouse model of cancer.

Although this example was based on cancer immunotherapy with HKCC alone, there are other immunotherapeutics and anticancer agents which could be combined with HKCC to further increase the antitumor effect. The present disclosure represents HKCC as an attractive therapeutic treatment for a range of cancers at a particular site or a metastasis.

Example 9: Antitumor Activity of HKCC Against a Solid Tumor

To examine whether HKCC can bolster immunity in such a way that it prevents and/or inhibits tumors from growing in the body, an immunotherapy model was used. Groups of five C57Bl6 mice were challenged with $0.25\times10^6$ EL-4 cells/mouse in 100 µl PBS s.c. in the lower left flank. Six days after, mice were treated once weekly subcutaneously for three times with HKCC ($50\times10^6$ CFU/mouse) or PBS control. Tumor growth was measured for 28 days after challenge using digital calipers in two perpendicular directions, and mice were humanely euthanized. Tumor area were calculated as length×width (in mm). Strikingly, treatment with HKCC resulted in significant reduction in tumor progression (FIG. 9A). In addition to decreasing tumor burden, HKCC therapy led to decreased PD-1 expression on CD4+, CD8+ and NKT cells (FIG. 9B), suggesting that immunotherapy with HKCC alone may function through modulating immune mechanisms. These studies suggest that HKCC can be used as immunotherapy to prevent, treat or ameliorate metastasis or recurrence or inhibit the growth or proliferation of a variety of cancer cells or tumors in the specific organ or tissue of an individual improving patient survival rates. Further, HKCC treatment may also be undertaken to rid the body of residual tumor after chemo, radiation or surgical treatments etc.

Example 10: Effect of Live CC and HKCC: HKCC Induces Robust Antigen-Specific Cellular (CD4+ and CD8+ T Cells) Immune Responses Against TIV (Seasonal) Influenza Vaccine Upon Single Mucosal (i.n.) Immunization with a Low Dose of Antigen The current seasonal influenza vaccine is assumed to work through inducing antibody responses against specific variants of influenza antigens HA and NA. However, literature suggests heterologous protection in certain instances possibly through induction of cellular immune responses and humoral responses against conserved regions of HA present in the current trivalent vaccine (TIV). Therefore, we examined whether HKCC can allow strong cellular immunity to be induced in mice immunized with HKCC and influenza TIV vaccine. Further, we sought to examine the effects of live vs. heat-killed CC to function as an efficient adjuvant inducing cellular immunity against influenza vaccine. Groups of five C57/b16 mice were immunized by the intranasal route with live CC or HKCC at 50×10$^6$ CFU/mouse with Vaxigrip (1.6 µg/mouse) in 30 µl total volume/mouse. In the control no adjuvant group, Vaxigrip (1.8 µg/mouse) alone was administered subcutaneously. Mice were euthanized 8 days after immunization. Intriguingly, the results obtained demonstrated that HKCC stimulates robust cell mediated CD4+ and CD8+ T cell immunity (proliferation and GrB production) against seasonal flu vaccine (Vaxigrip) as compared to live CC or no adjuvant group (FIG. 10A,B). Therefore, the HKCC adjuvanted vaxigrip (vaxigrip in a formulation with HKCC as an adjuvant) was superior to non-adjuvanted vaxigrip or live CC adjuvanted vaxigrip in inducing cellular immune responses. In contrast, T cell response to a mitogen ConA was similar in all three groups (FIG. 10A).

These results indicate that intranasal co-administration of HKCC with a licensed trivalent vaccine (vaxigrip) containing a mixture of hemagglutinin and neuraminidase antigens from H1, H3 and B strains of influenza virus significantly increase antigen-specific CD4+ T cells as well as GrB producing cytotoxic T cell responses in mice within 8 days of single immunization. Interestingly, only mice vaccinated intranasally with HKCC produced dramatic cellular immune responses compared with those of mice immunized intranasally with live CC or vaxigrip alone. CD8+ T cells are critical in controlling and eliminating respiratory infections, especially those caused by highly pathogenic strains of influenza viruses. CD8+ T cells specific for conserved or cross-reactive epitopes have been shown to mediate heterosubtype cell-mediated immunity against influenza strains that differ in HA serotypes. Importantly, T cell responses generated upon intranasal immunization of mice with HA and NA containing proteins admixed with HKCC, unlike vaxigrip, conferred significant protection against intranasal challenge with a heterologous strain of influenza virus as described in FIG. 14. Thus, HKCC induces broadly cross-reactive T cell immunity and would improve the efficacy of a commercially available influenza vaccine.

Example 11: HKCC Induces Long-Lasting Humoral and Cellular Antigen-Specific Cellular Immune Responses Against Co-Administration of Multiple Antigens of Influenza Upon Mucosal (i.n.) Immunizations with Low Doses of Antigens The shortcomings with current influenza vaccine are due to the induction of virus variant specific antibody responses, leading to a necessity of changing and updating the vaccine preparation for every influenza strain. A universal vaccine targeting multiple and conserved antigens of influenza and inducing both cellular and humoral immunity against these antigens will be an important step forward towards the development of an universal influenza vaccine. Therefore, we examined if HKCC could be used as an efficient adjuvant with multiple influenza antigens (M2e, and HA and NA containing Vaxigrip) to induce both humoral and cellular immune responses against these antigens.

Groups of five C57/b16 male mice were immunized with a mixture of seasonal TIV influenza vaccine (Vaxigrip 1.8 µg/mouse), M2e-monolipo peptide (20 µg/mouse) and HKCC (50×10$^6$ CFU/mouse) once or twice intranasally (at 21 days interval). Also, HKCC was used in combination with other adjuvants e.g., MPL (a TLR-4 agonist) (5 µg/mouse) or a polymeric compound e.g., poly-L-arginine hydrochloride (100 µg/mouse). Sera samples were collected 8 and 28 days after both single and two immunizations and mice were euthanized 8 days or 28 days after two immunizations.

The results showed that HKCC induces early, robust and long-lasting antigen specific T cell and antibody responses following one or two intranasal immunization(s) against both TIV and M2e antigens (FIG. 11A-G). Importantly, HKCC as an adjuvant in nasal vaccination induced antigen specific IgA in nasal and lung lavages of the mice (FIG. 11B-E). No IgE were developed against any antigens at both early and later time points. Intriguingly, the adjuvant effect of HKCC was further potentiated by the addition of MPL as well as poly-L arginine (FIG. 11A-G).

These results show that HKCC can induce robust humoral and cellular immune responses against a weakly immunogenic antigen, and combining with other adjuvants or molecules can further improve the immunogenicity of weak antigens. M2e, the ectodomain of the M2 protein found on the surface of influenza A viruses, is the most highly conserved surface protein of the virus. The admixing of HKCC induces robust immune responses against M2e as well as HA and NA (present in vaxigrip), and provides potential for a universal vaccine candidate for influenza. Also, HKCC and its combination with other adjuvants/molecules can allow the generation of strong cellular and humoral immunity simultaneously against multiple antigens even in a single vaccination. These studies further demonstrate that HKCC can provide enhanced antigen-specific immune responses when combined with other immunopotentiators to increase the immunogenicity and reduction of dose of antigens.

Example 12: HKCC Mediated PRR Signaling

Figure 12:
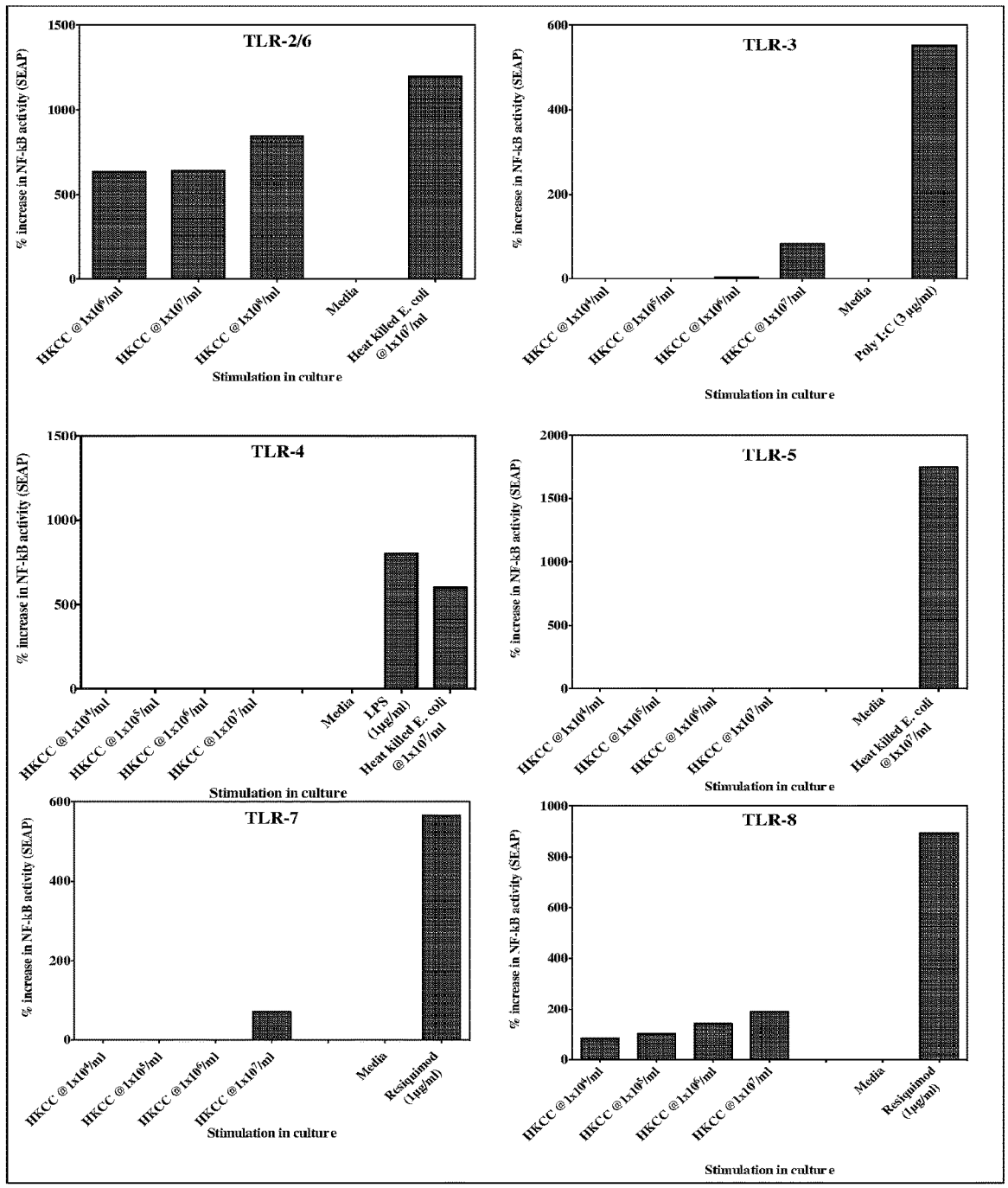
FIG. 12 depicts the effect of HKCC on activating TLRs and NLRs mediated signaling. The activity of HKCC (at concentrations $10^4$-$10^8$ cfu/ml) on various TLRs and NLRs was assessed with human embryonic kidney cells (HEK 293) expressing individual TLR or NLR (Invivogen) using the secretory embryonic alkaline phosphatase (SEAP) reporter gene that is linked to NF-kB activation in response to TLR or NLR stimulation. The SEAP activity was measured using Quanti-blue substrate.
Figure 12:
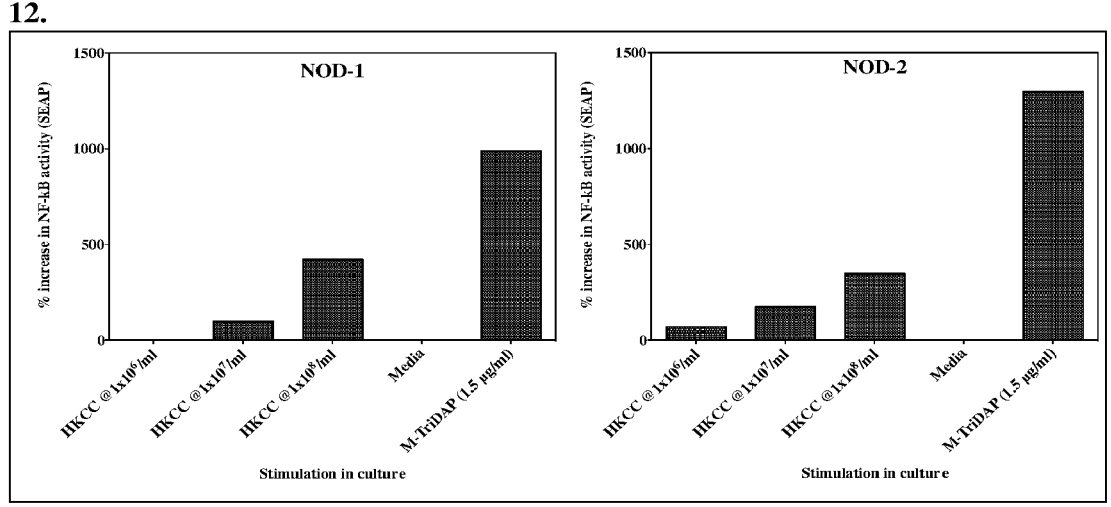

Evaluation of the ability of HKCC to stimulate various innate pathogen recognition receptors (PRRs) (TLR2/6, 3, 4, 5, 7, 8, NOD-1 and NOD-2) was performed using HEK293 cells stably expressing individual TLR or NLR. The cell lines were incubated for 24 hrs at 37° C. with HKCC at different concentrations ($10^4$-$10^8$ cfu/ml) and TLR/NLR specific ligands (LPS, heat killed E. coli, resiquimod, FSL-1, poly I:C, M-triDAP) as controls. NF-κB activation was determined by measuring the SEAP secreted in to the cell culture media using Quanti blue reporter assay (using reagents and protocols provided by Invivogen). Surprisingly, the results indicate that HKCC does not activate TLR-4 and TLR-5 signaling, but activates TLR-2/6, 3, 7, 8, NOD-1 and NOD-2 (FIG. 12).

In addition to innate and adaptive immune cells, mammalian pluripotent stem cells (CD34$^+$ progenitors) also express various TLRs such as TLR 2/6, 7, 8, 9. Therefore, HKCC can stimulate TLRs on stem cells to induce their proliferation, differentiation and restoration of homeostasis.

Figure 13:
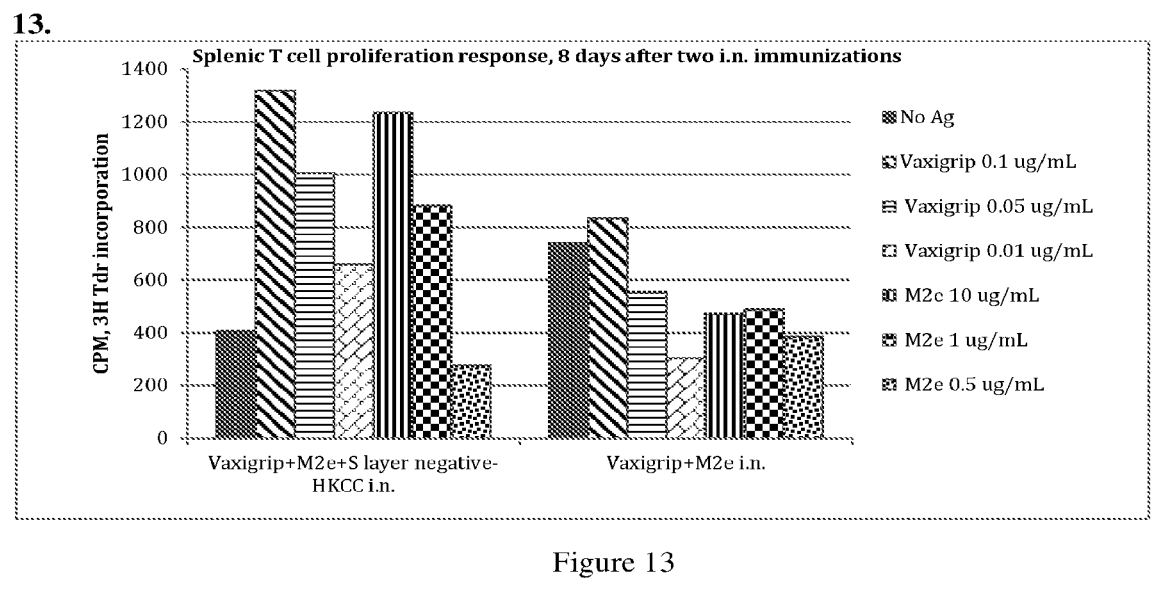

Example 13: S-Layer Negative HKCC Induces Antigen-Specific T Cell Response Against Multiple Antigens of Influenza Upon Mucosal (i.n.) Immunization To determine the role of surface S protein of CC in providing adjuvant effects, we used S-layer negative HKCC as an adjuvant in this experiment. C57/b16 male mice were given two intranasal immunizations at 21 day interval with a mixture of seasonal TIV influenza vaccine (Vaxigrip 1.8 µg/mouse), M2e-monolipo peptide (20 µg/mouse) and S-layer negative HKCC ($50 \times 10^6$ CFU/mouse). Mice were euthanized 8 days after the second immunization and T cell proliferative responses were examined in vitro against Vaxigrip and M2e antigens (FIG. 13). Interestingly the S-layer negative HKCC also provided a bolstering effect on T cell response against both of the influenza antigens, similar to those obtained using wild-type HKCC, suggesting that the S layer of CC is not essential in its activity as an adjuvant.

Example 14: Enhancement of Spectrum of Protection of Seasonal Flu TIV Vaccine (Vaxigrip) Upon Single Mucosal or s.c. Immunization: Protection from Heterologous Virus Infection Groups of three BALB/c female mice were immunized by the intranasal (1.8 µg/mouse Vaxigrip) or subcutaneous (3.6 µg/mouse Vaxigrip) routes with HKCC ($50 \times 10^6$ CFU/mouse) in 30 and 100 µl total volume/mouse, respectively. In the control no adjuvant group, Vaxigrip (3.6 µg/mouse) alone was administered subcutaneously. Eight days after immunization, mice were challenged intranasally with 30 µl/mouse of stock of H1N1 (PR8) virus and daily weights of individual mouse were recorded. Four days after infection, mice were euthanized and viral titers were determined in lung homogenates. Bronchoalveolar lavage (BAL) was also collected to determine cytokine and infiltrating immune cells. Interestingly, HKCC as an adjuvant in a seasonal flu vaccine (vaxigrip) provided protection from heterologous viral (H1N1) infection as well as protection from weight loss and enhanced infiltration of innate (DCs, NK, NKT) and adaptive immune cells (CD4 and CD8 T cells) and IL-2 production in the lungs upon single i.n. or s.c. immunization as compared to Vaxigrip alone or unimmunized groups (FIG. 14A-D). These results suggest that HKCC as an adjuvant in a influenza vaccine can provide cross-protection against unmatched viruses. These results demonstrate effect of HKCC combined with HA and NA proteins as a mucosal and parenteral adjuvant for induction of adaptive and innate immune responses, and cytokine, and protection against heterologous influenza virus. Thus, HKCC has potential to increase the breadth of protective hetero-subtypic immunity of HA and NA containing existing influenza vaccines. These results also show that single i.n. or s.c. vaccination with commonly available influenza vaccine in combination with HKCC strongly improves the efficacy of a commercially available influenza vaccine.

Although this example was based on influenza TIV vaccine, there are other influenza vaccines such as live attenuated influenza virus vaccine and tetravalent vaccine, which could be used in a similar manner. Therefore, the present disclosure represents attractive target for a range of influenza vaccines.

Example 15: Single Subcutaneous Immunization of a Poorly Immunogenic Antigen (M2e) Adjuvanted with WT-HKCC or LPS-Negative HKCC Protect from Weight-Loss after Influenza Virus Infection To determine the role of lipopolysaccharide (LPS) of CC in providing adjuvant effects, we used LPS negative HKCC as an adjuvant in this experiment. Groups of five BALB/c female mice were immunized once subcutaneously with M2e peptide or lipopeptide (25 µg/mouse) and WT HKCC or LPS-negative HKCC ($50 \times 10^6$ CFU/mouse) in 100 µl total volume/mouse at the base of the tail. Eight days after immunization, mice were challenged intranasally with 30 µl/mouse of stock of H1N1 (PR8) virus and daily weights of individual mouse were recorded. Four days after infection, mice were euthanized and BAL was collected to determine infiltrating cells. Immunization with both WT-HKCC or LPS-negative HKCC adjuvanted M2e (M2e in a formulation with HKCC as an adjuvant) partially protected mice from weight loss due to influenza infection and enhanced infiltration of innate and adaptive immune cells ($CD11c^+$ DCs, $CD11c^+CD40^+$ DCs, NKT, $CD3^+CD4^+$ T cells, and $CD3^+CD8^+$ T cells) in the lungs as compared to unimmunized group (FIG. 15A,B). These results demonstrate that HKCC as well as $LPS^-$ HKCC are potent inducer of innate and adaptive immune responses and provide protection from influenza virus infection. This experiment clearly suggested that LPS molecule of CC is not an essential component for the adjuvant activity of HKCC.

M2e is the most highly conserved surface protein of influenza viruses, therefore, HKCC adjuvanted M2e vaccine is expected to be effective against highly pathogenic strains of influenza such as H5N1, H7N9 etc. Several findings suggest the protective role of cellular (CD4+ and CD8+ T cells) and innate immune responses in other RNA viruses such as Dengue virus (DENV). Therefore, HKCC adjuvanted vaccines by inducing cellular immune responses may offer protection against other RNA viruses such as Dengue virus, West Nile virus, Japanese encephalitis virus, Yellow fever virus etc.

Example 16: Prophylactic Immunotherapy: Viral (H1N1) Protection Upon Pre-Treatment (24 hr Before Infection) with HKCC by Parenteral or Mucosal Route To determine if HKCC by virtue of its immunomodulatory activity can activate immune responses such that an individual is protected from getting an infection, we performed prophylactic treatment experiment with HKCC only given by various routes. Groups of five BALB/c female mice were treated with HKCC ($50 \times 10^6$ cfu/mouse) by subcutaneous (100 µl volume/mouse at the base of the tail), intranasal (30 µl total/mouse) or oral route (100 µl volume/mouse). Twenty four hours after treatment, mice were challenged intranasally with 30 µl/mouse of stock of H1N1 (PR8) virus and daily weights of individual mouse were recorded. Two and five days after infection, mice were euthanized and BAL and lung samples were collected. In this experiment, prophylactic treatment with HKCC protected mice from weight loss due to influenza infection, reduced viral load, enhanced infiltration of innate and adaptive immune cells and induction of IL-2, IFN-g, IL-17A cytokines in the lungs (FIG. 16A-D).

Significant amount of IL-2 and appreciable levels of IFN-γ and IL-17A were detected in the lungs of mice treated with HKCC as compared to untreated mice after influenza infection. Also, cytotoxic T lymphocytes, NK, NKT and DCs were detected in BAL in the HKCC treated mice without any inflammation in the lungs. These data suggest that HKCC is a potent inducer of TH1, TH17, NK, NKT and CD8 T cell responses and useful in the treatment of viral infections. Altogether, this study demonstrates that HKCC is a safe and effective immunotherapeutic agent that can provide antiviral therapeutic effect by all s.c., i.n. and oral routes against influenza and other respiratory viruses such as RSV, SARS etc. Generation of adaptive and innate immune responses to fight an established influenza infection is very important to combat influenza in the elderly. IL-17A producing T cells have been shown to be protective by others in influenza infection, implying the importance of TH17 response in immunity against pathogens.

Example 17: Antiviral Activity of HKCC Against H1N1 Infection: Immunotherapeutic Effect To determine if HKCC by virtue of its immunomodulatory activity, can be used as an immunotherapeutic agent to treat and/or ameliorate an infection, we performed immunotherapy experiment where mice were treated with HKCC alone 24 hrs after infection with influenza virus. Groups of five BALB/c female mice were challenged intranasally with 30 µl/mouse of stock of H1N1 (PR8). Twenty-four hours after the infection, mice were treated with HKCC ($50\times10^6$ cfu/mouse) subcutaneously (100 µl volume/mouse at the base of the tail), intranasally (30 µl total/mouse) or orally (100 µl volume/mouse, once or thrice). Five days after infection, mice were euthanized and lungs were collected to determine viral titers. The administration of HKCC in mice infected with H1N1 reduced viral (H1N1) load using subcutaneous, intranasal and oral routes (FIG. 17). These studies suggest that HKCC can be used effectively in a therapeutic regimen for the treatment of diseases by various routes. These results also demonstrate that HKCC could be used to treat other RNA and/or respiratory viruses.

Example 18: Antiviral Activity: HKCC Induces Cytokines from Human PBMCs which can Inhibit HCV Replication Alone and in Combination with Other Antiviral Drugs in Huh-7 Replicon Containing Cells Single treatment of Huh-7-1a replicon containing cells with supernatants from HKCC treated PBMCs from different individual donors for five days resulted in sustained reduction of viral RNA without affecting the cellular RNA (FIG. 18A,B). There was no significant difference in HCV levels with untreated PBMCs' supernatant. The supernatant was also tested to assess the potential use of HKCC in combination therapies with other anti-HCV chemotherapeutic agents telaprevir and ribavirin. The results obtained demonstrate that combination treatment of replicon cells with HKCC and inhibitors targeting HCV protease or other pathways lead to synergistic antiviral effects (FIG. 18B). As control for non-specific effects, HKCC was also tested directly to HCV replicon cells where it did not have any effect on HCV replication. These data suggest that HKCC's activity is due to the induction of antiviral cytokines and thus it can be used to treat HCV infection of different genotypes, IFN-α non-responder HCV, drug-resistant HCV and other hard to treat HCV populations including patients with co-infections and cancers.

Although this example was based on activity against HCV, there are other viruses and microorganisms that can be inhibited by soluble factors produced by PBMCs stimulated with HKCC alone and/or in combination with other chemo and immunotherapeutics. Therefore, the methods of the present disclosure represent an attractive treatment for a range of infections.

Example 19: Intracellular Activity: HKCC Induces Cytokines from Human PBMCs which can Inhibit Intracellular Bacterial Replication Human monocytic cell line (THP-1) was infected with *M. avium* or Mtb H37Ra, followed by two treatments (on days 0 and 4) with supernatants (50%) collected from human PBMCs treated for 24 hrs with HKCC or PBS. HKCC efficiently inhibits intracellular mycobacterial growth in a host-immune dependent manner as compared to supernatants collected from PBS treated human PBMCs (FIG. 19). These data provide supportive evidence that HKCC has strong potential to efficiently inhibit growth of other intracellular pathogens such as mycobacteria, lysteria, *leishmania*, intracellular $G^+$ and $G^-$ bacteria and malaria parasites etc.

Example 20: HKCC is Effective in Combination with Chemotherapeutic Drug in Reducing Bacterial Burden Groups of 5 BALB/c female mice were challenged with H37Ra ($0.5\times10^6$ cfu/mouse) intravenously. Five days post infection, mice were treated with HKCC (s.c.), and INH (oral) or PBS using a schedule shown in the FIG. 20. HKCC in combination with first-line tuberculosis drug INH provides enhanced antimycobacterial effects in a Mtb infected mouse model than INH alone. Significantly higher reduction in mycobacterial loads was observed in lungs, liver and spleen as compared to INH and no treatment groups (FIG. 20). Thus, HKCC can be combined with an antimicrobial agent to achieve more complete inhibition of a pathogen, shorten the treatment duration, reduce the dose of chemotherapeutic agents and also treat drug resistant strains of pathogens, as an immunotherapeutic.

Example 21: HKCC Elicits Potent Adjuvant Activity Enhancing Malaria Derived Antigen Spf66-Specific T Cell Responses To determine if HKCC could be used as an adjuvant for Malaria vaccine, male C57/b16 mice were immunized subcutaneously twice (at 12 days interval) with HKCC ($50\times10^6$/mouse)+Spf66 peptide (20 ug/mouse), Spf66 peptide (20 ug/mouse) alone or PBS. Mice were euthanized eight days after second immunization. The spleens of immunized mice were isolated and examined for antigen specific proliferative responses. The results demonstrated that HKCC adjuvant enhances malaria antigen-specific T cells when compared to peptide alone or unimmunized mice (FIG. 21). There is evidence that human and murine T cells, induced against a variety of malaria antigens, can control parasite growth in vitro and in vivo. The results obtained show that HKCC can induce malaria antigen-specific T cell responses and therefore could be used as an effective adjuvant to modulate and/or augment protective immune responses elicited by malaria vaccines.

Example 22: HKCC Induces Antigen Specific T Cell Responses Against M2e Upon Oral Immunization and Viral Challenge To determine the role of HKCC as an oral adjuvant, groups of five BALB/c female mice were immunized twice orally (at 12 days interval) with M2e lipopeptide (50 µg/mouse)+HKCC ($50\times10^6$ CFU/mouse), M2e lipopeptide (50 µg/mouse) alone or PBS in 200 µl total volume/mouse. Twelve days after immunizations, mice were challenged intranasally with 30 µl/mouse of stock of H1N1 (PR8) virus. Four days after infection mice were euthanized. Spleens and BALs were collected. Oral immunization with HKCC induced antigen specific proliferation and activation of CTLs in splenocytes and enhanced infiltration of activated CTLs in BALs as compared to M2e alone or PBS immunized groups (FIG. 22). These results demonstrate that HKCC is a potent oral adjuvant and can enhance the immunogenicity of poorly immunogenic antigens. CD8+ T cells are critical in controlling and eliminating respiratory infections, especially those caused by highly pathogenic strains of influenza viruses. Importantly, T cell responses were generated upon oral immunization of mice with M2e admixed with HKCC in BALs and spleens of the immunized mice.

Example 23: Recombinant Adenoviral Vector Containing HCV-NS3 Induces Antigen Specific T Cell Responses HKCC admixed with recombinant adeno-NS3 enhanced antigen specific responses against NS3 as compared to recombinant-NS3 or PBS immunized groups (FIG. 23). Female C57b/6 mice (n=5/group) were immunized twice (at 14 days interval) intramuscularly with $2\times10^7$ PFU/mouse adenoviral vector (rAd-NS3), rAd-NS3+HKCC, or PBS. Eight days after second immunization, mice were euthanized. The proliferation of spleen T cells was determined against HCV NS3 antigen and mixture of 15-aa peptides from NS3. This study demonstrates that recombinant-vector based vaccines combined with HKCC resulted in improvement of the immunogenicity of the vector-based vaccine. These data indicate that HKCC can be used as an adjuvant with vector-based vaccines.

Examples 24: HKCC Mixed with IFA Elicits Strong T Cell Responses Following Single Subcutaneous Immunization with a Low Dose of Antigen (Vaxigrip) and Challenge with Heterologous (H1N1) Influenza Virus Groups of five BALB/c female mice were immunized by the subcutaneous route with
HKCC at $50\times10^6$ CFU/mouse, IFA (20 µl) and Vaxigrip (0.5 µg/mouse) in 100 µl total volume/mouse. In the control no adjuvant group, Vaxigrip (0.5 µg/mouse) alone was administered subcutaneously. Mice were challenged with H1N1 intranasally 8 days after immunization and euthanized 3 days after infection. Intriguingly, the results obtained demonstrated that HKCC with low doses of antigen and IFA stimulates robust T cell immunity (proliferation) against seasonal flu vaccine (Vaxigrip) as compared to no adjuvant group (FIG. 24). Therefore, the HKCC adjuvanted vaxigrip (vaxigrip in an oil-in-water formulation with HKCC as an adjuvant) was superior to non-adjuvanted vaxigrip in inducing cellular immune responses after heterologous viral challenge.

Example 25: Recombinant HKCC Containing Hemagglutinin Protein from Influenza Virus (H5-HKCC) after Intranasal Immunization Induces Influenza Antigens' Specific T Proliferative Responses Groups of five BALB/c female mice were immunized with recombinant H5-HKCC or wild-type HKCC ($50\times10^6$ cfu/ml) twice intranasally (at 8 days interval) and challenged with H1N1 influenza 12 days after second immunization. Mice were euthanized 3 days after infection. H5-HKCC induced influenza virus antigens' specific T cell responses, which was higher than immunization with wild-type HKCC (FIG. 25).

These results show that genetically modified HKCC expressing a heterologous polypeptide of a pathogen associated antigen (H5 of influenza virus) can induce cellular immune responses against influenza antigens upon immunization by mucosal route.

Example 26: Effect of Live CC and/or HKCC: HKCC Induces Robust Antigen-Specific Humoral Immune Responses Against Co-Administration of Multiple Antigens of Influenza Upon Single s.c. Immunization and Challenge with Heterologous Influenza Virus It was examined whether HKCC could be used as an efficient adjuvant with multiple influenza antigens (M2e, and HA and NA containing Vaxigrip) to induce antigen specific humoral immune responses against multiple antigen within a short period of time. Groups of five BALB/s female mice were immunized with a mixture of seasonal TIV influenza vaccine (Vaxigrip 1.0 µg/mouse), M2e-monolipo peptide (20 µg/mouse) and HKCC ($50\times10^6$ CFU/mouse); Vaxigrip (1.0 µg/mouse), M2e-monolipo peptide (20 µg/mouse) and live CC ($50\times10^6$ CFU/mouse); Vaxigrip (1.0 µg/mouse), M2e-monolipo peptide (20 µg/mouse); or PBS once subcutaneously. Mice were challenged intranasally with H1N1 influenza virus eight days after immunization. Sera samples were collected 4 days after infection (11 days after single immunization) and examined for antibodies against Vaxigrip and M2e (FIG. 26).

The results showed that HKCC induces early and robust antigen specific antibody (IgG, IgG1, IgG2a and IgG3) responses following single subcutaneous immunization against both Vaxigrip and M2e antigens, as compared to no adjuvant or no immunization groups (FIG. 26). In contrast, immunization of antigens with live CC led to an overall reduction in all of the antibodies measured as compared to immunization with antigens without adjuvant (FIG. 26). These results indicate that coadministration of HKCC with a licensed trivalent vaccine containing a mixture of HA and NA, and a conserved antigen M2e, as a universal vaccine, induces strong antigen specific antibody responses in mice within 11 days of immunization and heterologus virus infection.

Example 27: In Vitro Induction of IFN-α by Human PBMCs Stimulated with HKCC

TABLE 1

| | IFN-α (pg/ml) |
|---|---|
| Saline | 0 |
| HKCC $1 \times 10^5$ CFU/ml | 13 (Donor #1) |
| HKCC $1 \times 10^6$ CFU/ml | 9 (Donor #2) |
| HKCC $1 \times 10^7$ CFU/ml | 9 (Donor #3) |

Human PBMCs ($4\times10^6$/well) were treated with HKCC ($1\times10^5$, $1\times10^6$ and $1\times10^7$ CFU/ml), for 24 hours. Supernatants were collected and assayed for IFN-α by ELISA. The data are presented in Table 1. Data are representative of three experiments from three different individual donors. These results indicate that HKCC induces IFN-α response from human PBMCs. There are emerging clinical evidence that interferons are useful and viable treatments for a variety of viral infections such as HBV, HCV, influenza, SARS, Dengue, rhinoviruses, HPV, HIV, pox viruses etc. Clinical benefits of type 1 interferons alone and in combination with chemotherapeutics have also been observed in various cancers (melanoma, renal cell carcinoma, multiple myeloma, leukemia, AIDS related Kaposi's sarcoma). Therefore, HKCC could be used to treat various viral diseases and cancers.

Example 28: In Vitro Induction of IL-12 by Human PBMCs Stimulated with HKCC

TABLE 2

| | IL-12 (pg/ml) |
|---|---|
| Saline | 0 |
| HKCC $1 \times 10^5$ CFU/ml | 250 |
| HKCC $1 \times 10^6$ CFU/ml | 750 |
| LPS (1 µg/ml) | 2160 |

IL-12 can promote IFN-gamma production and enhance the proliferation and cytotoxicity of CTLs. It also induces an anti-angiogenic program and provides costimulatory and anti-apoptotic signals that regulate the activity of effector-memory T cells. Therefore, the induction of IL-12 by human PBMCs upon stimulation by HKCC was examined. Human PBMCs ($4 \times 10^6$/well) were treated with HKCC ($1 \times 10^5$ and $1 \times 10^6$ CFU/ml), for 24 hours. Supernatants were collected and assayed for IL-12 by ELISA. The data are presented in Table 2. Data are representative of three experiments from three different individual donors. Results show that HKCC is capable of activating human PBMCs in a dose dependent manner and stimulating the production of IL-12 in vitro, suggesting the activation of innate immune cells. The ability of HKCC to induce IL-12 secretion is also a good measure of its adjuvant potential inducing TH1 immune responses.

Example 29: In Vitro Induction of Cytokines (pg/ml) from Human PBMCs Upon Stimulation with HKCC

TABLE 3

| | IFN-γ | TNF-α | IL-2 | IL-6 | IL-10 | IL-17A | IL-22 |
|---|---|---|---|---|---|---|---|
| PBS | 0.0 | 0.0 | 0.0 | 0.0 | 0.0 | 0.0 | 0.0 |
| HKCC $1 \times 10^6$ CFU/ml | 135 | 41 | 35 | 1500 | 40 | 290 | 20 |
| HKCC $1 \times 10^7$ CFU/ml | 420 | 54 | 41 | 1500 | 66 | 310 | 199 |
| HKCC $5 \times 10^7$ CFU/ml | 1500 | 125 | 37 | 2000 | 183 | 392 | 228 |

Human PBMCs ($4 \times 10^6$/well) were treated with HKCC ($1 \times 10^6$, $1 \times 10^7$ and $5 \times 10^7$ CFU/ml), for 96 hours. Supernatants were collected and assayed for cytokines by ELISA. The data are presented in Table 3. Data are representative of three experiments from three different individual donors. These results indicate that HKCC induces regulated levels of diverse range multifunctional cytokines from human PBMCs, which could be produced by various innate and/or adaptive immune cells present in PBMCs and which have been associated with protection in several diseases in human subjects.

Example 30: In Vivo Induction of IL-12 in Lungs Upon i.n. And Oral Administration of HKCC in Mice

TABLE 4

| | IL-12 (pg/ml) |
|---|---|
| Saline | 0 |
| HKCC $50 \times 10^6$ CFU/mouse i.n. | 20 |
| HKCC $50 \times 10^6$ CFU/mouse oral | 170 |

Recombinant IL-12 alone or combined with chemotherapy and/or monoclonal antibodies has been demonstrated to be effective in murine models and human clinical trials of breast cancer, metastatic melanoma, merkel cell carcinoma, cutaneous T cell lymphoma etc. Sequential use of paclitaxel and IL-12 has been shown to reduce tumor burden in mice. To determine whether HKCC can cause in vivo immune stimulation, HKCC or PBS was administered to C57bl/6 mice by intranasal and oral routes at $50 \times 10^6$ pfu/mouse dose and lung washes were collected after 5 hrs. The production of IL-12 was determined by ELISA. The data are presented in Table 4. HKCC induced the production of IL-12 in lungs upon intranasal and oral administration in mice in vivo experiments. IL-12 levels were strong and higher in mice that received HKCC orally than those receiving HKCC intranasally. Mice that received PBS had no IL-12 detected. This data confirms our in vitro studies with human PBMCs and demonstrates that HKCC by both mucosal routes activates innate immunity.

Example 31: In Vivo Induction of IFN-Beta in Serum and Lungs Upon Single Subcutaneous, i.n. or Oral Administration of HKCC in Mice

TABLE 6

| | IFN-beta in serum (pg/ml) |
|---|---|
| Saline | 67 |
| HKCC $50 \times 10^6$ CFU/mouse s.c. | 127.5 |

TABLE 7

| | IFN-beta in lungs (pg/ml) |
|---|---|
| Saline | 20 |
| HKCC $50 \times 10^6$ CFU/mouse i.n. | 70 |
| HKCC $50 \times 10^6$ CFU/mouse oral | 80 |

The ability of HKCC to induce type 1 interferon was assessed in vivo. C57bl/6 mice were administered once with HKCC ($50 \times 106$ cfu/ml) by s.c., oral and i.n. routes. Serum and lung washes were collected at 5 hrs after HKCC administration and IFN-beta was determined by ELISA. The data are presented in Tables 6 and 7. Significant levels of IFN-beta were detected in the serum and lungs of mice treated with HKCC by s.c., i.n., and oral routes, compared to PBS group. Type 1 interferons have widespread potential as therapeutic agents for the treatment of viral infections, microbial infections and cancers. IFN-beta was found to be a potent inhibitor of influenza and SARS-CoV (severe acute respiratory syndrome associated with coronavirus). Interferon-beta is also used clinically for the treatment of multiple sclerosis. These results suggest that HKCC is a potent IFN-beta inducer in vivo.

Example 32: In Vivo Induction of GM-CSF in Lungs Upon Single i.n. Administration of HKCC in Mice

TABLE 8

|  | GM-CSF in lungs (pg/ml) |
| --- | --- |
| Saline | 0 |
| HKCC 50 × 10⁶ CFU/mouse i.n. | 59 |

The ability of HKCC to induce GM-CSF was assessed in vivo. C57bl/6 mice were administered once with HKCC ($50 \times 10^6$ cfu/ml) by i.n. route. Lung washes were collected at 5 hrs after HKCC administration and GM-CSF was determined by ELISA. The data are presented in Table 8. HKCC treated mice had significant amount of GM-CSF in lungs compared to PBS treated mice.

Example 33: In Vivo Induction of IL-17A in Lungs Upon Single i.n. Administration of HKCC in Mice

TABLE 9

|  | IL-17A in lungs (pg/ml) |
| --- | --- |
| Saline | 0 |
| HKCC 50 × 10⁶ CFU/mouse i.n. | 20 |

IL-17A producing T helper (TH17) cells are a distinct lineage of T cells. These cells play an important role in the host defense against various pathogens. TH17 memory cells are key players in mucosal immunity. TH17 cells play a crucial role in mounting the immunity for both intracellular and extracellular pathogens and their primary function is to clear various pathogens. Genetic deficiency in mounting an effective TH17 response in humans results in mucocutaneous and staphylococcal lung infections. The effector CD4+ T cells defined by their production of IL-17A, has been found to provide protection against bacterial, mycobacterial, fungal, and viral infections. The TH17 subsets are deleted in chronically-HIV infected patients. Memory CD4 T cells have a pivotal role in HIV/AIDS eradication and cure. IL-17A expression has also been detected in γδ T cells, NK cells, CD8+ T cells, T-follicular helper (Tfh) cells and neutrophils.

To determine whether HKCC can cause IL-17A stimulation in vivo, C57bl/6 mice were administered once with HKCC ($50 \times 10^6$ cfu/ml) by i.n. route. Lung washes were collected at 5 hrs after HKCC administration and IL-17A was determined by ELISA. The data are presented in Table 9. A marked induction of IL-17A as observed in lungs of HKCC treated mice. In contrast, there was no induction of IL-17A in mice treated with saline. These studies demonstrate that HKCC can induce IL-17A in an individual and therefore could be used as an immunotherapeutic to treat viral diseases (such as HIV, HCV, HBV etc.), fungal diseases (such as *C. albicans* etc.), mycobacterial diseases (such as Mtb etc.), bacterial infections (such as *K. pneumonia, P. carinii, S. aureus, H. pylori, S. pneumonia, B. anthacis* etc.), and parasitic diseases (such as Toxoplasmosis etc.).

Example 34: In Vitro Activation of Human DCs by HKCC

TABLE 10

|  | % positive cells | | | |
| --- | --- | --- | --- | --- |
|  | CD11c | CD80 | CD86 | DEC-205 |
| Saline | 65.5 | 0.3 | 63.7 | 7.8 |
| HKCC 5 × 10⁷ CFU/ml | 70.2 | 0.9 | 70 | 16.3 |

The effect of the HKCC on human DCs was investigated by analyzing the expression of co-stimulatory molecules following treatment of human DCs with HKCC for 24 hrs. The data are presented in Table 10. The results obtained showed that HKCC induces up-regulation of expression of CD11c, CD80, CD86 and DEC-205 on human DCs.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of modulating an antigen-specific immune response in an individual, the method comprising administering to the individual an effective amount of an immunomodulatory composition comprising:
   a) heat-killed *Caulobacter* spp.;
   b) a pathogen-derived antigen, or a tumor-associated antigen; and
   c) a pharmaceutically acceptable excipient;
wherein the *Caulobacter* spp. is selected from the group consisting of *Caulobacter vibroides*, *Caulobacter henricii*, *Caulobacter fusiformis*, *Caulobacter intermedius*, and *Caulobacter subvibroides*, and the composition is administered via an oral, nasal, subcutaneous, intramuscular, topical or mucosal route of administration.

2. The method of claim 1, wherein the immune response comprises a humoral immune response, a cellular immune response, an innate immune response, and/or production of one or more cytokines.

3. The method of claim 1, further comprising administering to the individual a cancer chemotherapeutic agent, an anti-bacterial agent, an anti-mycobacterial agent, an anti-viral agent, an anti-protozoan agent, an anti-malarial agent, an anti-helminth agent, or a therapeutic treatment for cancer selected from the group consisting of radiation therapy, laser therapy, photodynamic therapy, and surgery.

4. The method of claim 1, further comprising administering to the individual an antibody.

5. The method of claim 1, further comprising administering to the individual a cytokine, an adjuvant, or an immunomodulatory agent.

6. The method of claim 1, wherein the individual is a human, a non-human mammal, or a non-mammal animal.

7. A method of reducing tumor progression or an infection in an individual having a disease selected from the group consisting of cancer and an infectious disease, wherein the infectious disease is caused by a virus, a bacterium, or a fungus, the method comprising administering to the individual a composition comprising:
   a) heat-killed *Caulobacter* spp.; and
   b) a pharmaceutically acceptable excipient;
wherein the *Caulobacter* spp. is selected from the group consisting of *Caulobacter vibroides*, *Caulobacter henricii*, *Caulobacter fusiformis*, *Caulobacter intermedius*, and *Caulobacter subvibroides*, and the composition is administered via an oral, nasal, subcutaneous, intramuscular, topical or mucosal route of administration.

8. The method of claim 7, further comprising administering an anti-bacterial agent, an anti-mycobacterial agent, an anti-viral agent, an anti-protozoan agent, an anti-malarial agent, an anti-helminth agent, an immunomodulatory agent, an antibody, a cytokine, an adjuvant, a vaccine, a cancer chemotherapeutic agent, or a therapeutic treatment for cancer selected from the group consisting of radiation therapy, laser therapy, photodynamic therapy, and surgery.

9. The method of claim 7, wherein the individual is a human, a non-human mammal, or a non-mammal animal.

10. A method of enhancing the efficacy and/or reducing the toxicity of an anticancer therapeutic treatment in an individual, the method comprising administering to the individual an effective amount of an immunomodulatory composition comprising:
   a) heat-killed *Caulobacter* spp.; and
   b) a pharmaceutically acceptable excipient;
wherein the *Caulobacter* spp. is selected from the group consisting of *Caulobacter vibroides, Caulobacter henricii, Caulobacter fusiformis, Caulobacter intermedius*, and *Caulobacter subvibroides*, and the composition is administered via an oral, nasal, subcutaneous, intramuscular, topical or mucosal route of administration.

* * * * *

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
ctgtcttcac gcagaaagcg                                          20

<210> SEQ ID NO 2
<211> LENGTH: 20
<212> TYPE: DNA
<213> ORGANISM: Artificial Sequence
<220> FEATURE:
```

```
<223> OTHER INFORMATION: primer

<400> SEQUENCE: 2
cactcgcaag caccctatca                                            20

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
cgatgcagaa ggagatcact g                                          21

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
cgatccacac ggagtacttg                                            20

<210> SEQ ID NO 5
<211> LENGTH: 23
<212> TYPE: PRT
<213> ORGANISM: Artificial Sequence
<220> FEATURE:
<223> OTHER INFORMATION: Influenza M2e peptide

<400> SEQUENCE: 5

Ser Leu Leu Thr Glu Val Glu Thr Pro Ile Arg Asn Glu Trp Gly Cys
1               5                   10                  15

Arg Cys Asn Asp Ser Ser Asp
            20
```